US009359400B2

(12) United States Patent
Usera et al.

(10) Patent No.: US 9,359,400 B2
(45) Date of Patent: Jun. 7, 2016

(54) SITE-SPECIFIC CHEMOENZYMATIC PROTEIN MODIFICATIONS

(71) Applicants: Aimee Usera, Cambridge, MA (US); Zachary Robinson, Arlington, MA (US); Jennifer Cobb, Cambridge, MA (US)

(72) Inventors: Aimee Usera, Cambridge, MA (US); Zachary Robinson, Arlington, MA (US); Jennifer Cobb, Cambridge, MA (US)

(73) Assignee: NOVARTIS AG (CH)

( * ) Notice: Subject to any disclaimer, the term of this patent is extended or adjusted under 35 U.S.C. 154(b) by 0 days.

(21) Appl. No.: 14/329,758

(22) Filed: Jul. 11, 2014

(65) Prior Publication Data

US 2015/0017192 A1 Jan. 15, 2015

Related U.S. Application Data

(60) Provisional application No. 61/845,273, filed on Jul. 11, 2013, provisional application No. 62/016,044, filed on Jun. 23, 2014.

(51) Int. Cl.

| | |
|---|---|
| ***C07K 5/103*** | (2006.01) |
| ***A61K 49/00*** | (2006.01) |
| ***A61K 47/48*** | (2006.01) |
| ***C07K 5/083*** | (2006.01) |
| ***C07K 5/062*** | (2006.01) |
| ***C07K 1/13*** | (2006.01) |
| ***C07D 209/42*** | (2006.01) |
| ***C07K 7/02*** | (2006.01) |
| ***C07K 5/072*** | (2006.01) |
| ***C07C 271/22*** | (2006.01) |
| ***C07C 317/28*** | (2006.01) |
| *A61K 38/06* | (2006.01) |
| *A61K 38/05* | (2006.01) |
| *A61K 38/07* | (2006.01) |

(52) U.S. Cl.

CPC ........... *C07K 5/101* (2013.01); *A61K 47/48261* (2013.01); *A61K 49/0002* (2013.01); *C07C 271/22* (2013.01); *C07C 317/28* (2013.01); *C07D 209/42* (2013.01); *C07K 1/13* (2013.01); *C07K 5/06043* (2013.01); *C07K 5/06104* (2013.01); *C07K 5/0808* (2013.01); *C07K 7/02* (2013.01); *A61K 38/05* (2013.01); *A61K 38/06* (2013.01); *A61K 38/07* (2013.01); *C07C 2102/24* (2013.01)

(58) Field of Classification Search

None

See application file for complete search history.

(56) References Cited

U.S. PATENT DOCUMENTS

| | | | |
|---|---|---|---|
| 4,179,337 | A | 12/1979 | Davis et al. |
| 5,156,956 | A | 10/1992 | Motoki et al. |
| 5,252,469 | A | 10/1993 | Andou et al. |
| 5,306,492 | A | 4/1994 | Porro |
| 5,425,946 | A | 6/1995 | Tai et al. |
| 5,508,191 | A | 4/1996 | Kanegae et al. |
| 5,543,397 | A | 8/1996 | Drauz et al. |
| 5,731,183 | A | 3/1998 | Kobayashi et al. |
| 2004/0266854 | A1 | 12/2004 | Becker et al. |
| 2008/0019918 | A1 | 1/2008 | Aoki et al. |
| 2011/0020837 | A1 | 1/2011 | Haberkant et al. |
| 2011/0184147 | A1 | 7/2011 | Kamiya et al. |
| 2012/0225089 | A1 | 9/2012 | Bouchard et al. |

FOREIGN PATENT DOCUMENTS

| | | | |
|---|---|---|---|
| EP | 0 477 508 | A1 | 4/1992 |
| EP | 0 785 276 | A1 | 7/1997 |
| EP | 0 815 833 | A2 | 1/1998 |
| EP | 0 950 665 | A1 | 10/1999 |
| JP | 2003199569 | A | 7/2003 |
| WO | WO 94/05325 | A1 | 3/1994 |
| WO | WO 96/06931 | A1 | 3/1996 |
| WO | WO 96/22366 | A1 | 7/1996 |
| WO | WO 96/40795 | A1 | 12/1996 |
| WO | WO 98/42721 | A1 | 10/1998 |
| WO | WO 00/56357 | A2 | 9/2000 |
| WO | WO 02/058737 | A2 | 8/2002 |
| WO | WO 03/080678 | A1 | 10/2003 |
| WO | WO 03/097091 | A2 | 11/2003 |
| WO | WO 2005/033148 | A1 | 4/2005 |
| WO | WO 2006/050341 | A2 | 5/2006 |
| WO | WO 2006/082527 | A2 | 8/2006 |
| WO | WO 2008/084411 | A2 | 7/2008 |
| WO | WO 2009/027369 | A1 | 3/2009 |
| WO | WO 2009/081276 | A2 | 7/2009 |
| WO | WO 2011/002852 | A2 | 1/2011 |
| WO | WO 2011/079315 | A1 | 6/2011 |
| WO | WO 2012/004419 | A2 | 1/2012 |
| WO | WO 2012/006475 | A1 | 1/2012 |
| WO | WO 2012/058635 | A1 | 5/2012 |
| WO | WO 2012/078559 | A2 | 6/2012 |
| WO | WO 2012/082618 | A2 | 6/2012 |
| WO | WO 2012/142659 | A1 | 10/2012 |

OTHER PUBLICATIONS

Pasternack et al., Analytical Biochemistry (1997) 249, 54-60.*
Macédo et al., Analytical Biochemistry (2000) 285, 16-20.*
Van Geel et al., Amino Acids (2012) 43, 1251-1263.*
Dommerholt et al., Angewandte Chemie Int Ed (2010) 49, 9422-9425.*
Albalat, Rosa, et al., "Langmuir Monolayers of Diacyl Glycerol Amino Acid-Surfactants. Effect of the Substitution Pattern of the Glycerol Backbone," *Langmuir* 19(26):10878-10884 (2003).
Crotti, Stefano et al., "Defined Conjugation of Glycans to the Lysines of CRM Guided by their Reactivity Mapping." *Chembiochem*, pp. 836-843 (2013).

(Continued)

*Primary Examiner* — Marcela M Cordero Garcia
*Assistant Examiner* — Catherine Mader
(74) *Attorney, Agent, or Firm* — Brinks Gilson & Lione; Ryan L. Marshall

(57) ABSTRACT

The present invention relates to methods and reagents for use in site-selective modification of proteins having lysine residues with functionalized peptides using a chemoenzymatic microbial transglutaminase-mediated reaction. The functionalized proteins may be used for study or therapeutic uses.

9 Claims, 6 Drawing Sheets

(56) References Cited

OTHER PUBLICATIONS

Lang, Kathrin, et al., "Genetic Encoding of Bicyclononynes and *trans*-Cyclooctenes for Site-Specific Protein Labeling in Vitro and in Live Mammalian Cells via Rapid Fluorogenic Diels—Alder Reactions," *J. Am. Chem. Soc.* 134(25):10317-10320 (2012).
Mindt, Thomas L., et al., "Modification of Different IgG1 Antibodies via Glutamine and Lysine using Bacterial and Human Tissue Transglutaminase," *Bioconjugate Chem.* 19(1):271-278 (2008).
Morán, Carmen, et al., "Synthesis of glycerol amino acid-based surfactants. Part 2. Lipase-catalysed synthesis of 1-*O*-lauroyl-*rac*-glycero-3-*O*-($N^{\alpha}$-acetyl-L-amino acid) and 1,2-di*O*-lauroyl-*rac*-glycero-3-*O*-($N^{\alpha}$-acetyl-L-amino acid) derivatives," *J. Chem. Soc., Perkin Trans.* 1, 1124-1134 (2002).
Moreau, Monique et al., "Structure of the type 5 capsular polysaccharide of *Staphylococcus aureus." Carbohydrate Research*, 201 pp. 285-297 (1990).
Satwekar, Abhijeet, et al., "Site-Specific Modification of Proteins Mediated by Transglutaminase," *Nature Precedings*, 1 page (2011).
Zlatopolskiy, Boris D., et al., "Beyond azide-alkyne click reaction: easy access to F-labelled compounds via nitrile oxide cycloadditions," *Chem. Commun.* 48(57):7134-7136 (2012).
Ahmad & Chapnick, "Conjugated polysaccharide vaccines," *Infect. Dis. Clin. North Am.* 13:113-33, vii (1999).
Amaya et al., *Tetrahedron Letters* 42:9191-9194 (2001).
Bardotti et al., *Vaccine* 26:2284-96 (2008).
Barsanti et al., *J App. Phycology* 13:59-65 (2001).
Berkin et al., *Chemistry* 8:4424-4433 (2002).
Broadhead et al., *Drug Devel. Ind. Phann.* 18:1169-1206 (1992).
Buttery & Moxon, *J R Coll Physicians Lond* 34:163-168 (2000).
Canalle, Luiz A., et al., "Clickable Enzyme-Linked Immunosorbent Assay," *Biomacromolecules* 12:3692-3697 (2011).
Costantino et al., *Vaccine* 17:125-1263 (1999).
Dommerholt, Jan, et al., "Readily Accessible Bicyclononynes for Bioorthogonal Labeling and Three-Dimensional Imaging of Living Cells," *Angew. Chem. Int. Ed.* 49:9422-9425 (2010).
Du et al., *Tetrahedron* 60:6345-6351 (2004).
Fattom et al., *Infect Immun.* 58(7):2367-74 (1990).
Fattom et al., *Infect Immun.* 66(10):4588-92 (1998).
Fournier et al., *Infect. Immun.* 45(1):87-93 (1984).
Frash, *Advances in Biotechnological Processes* (eds. Mizrahi & Van Wezel), 13:123-145 (1990).
Geurtsen et al., *Journal of Organic Chemistry* 64(21):7828-7835 (1999).
Gilbert et al., *J. Microb. Meth.* 20:39-46 (1994).
Glode et al., *J Infect Pis* 139:52-56 (1979).
Goldblatt, *J. Med. Microbiol.* 47:563-567 (1998).
Guttormsen et al., *Proc Natl Aced Sci U S A*, 105(15):5903-8 (2008) Epub Mar. 31, 2008.
Hestrin, *J. Biol. Chem.* 180:249-261 (1949).
Hoog et al., *Carbohydr Res.* 337(21-23):2023-36 (2002).
Huang et al., *Carbohydr Res.* 340:603-608 (2005).
Inzana, *Infect. Immun.* 55:1573-1579 (1987).
Jamois et al., *Glycobiology* 15(4): 393-407 (2005).
Jones and Lemercinier, *J Pharm BiomedAnal.* 30(4):1233-47 (2002).
Jones, *An. Acad. Bras. Cienc* 77(2):293-324 (2005).
Jones, *Carbohydrate Res.* 340(6):1097-106 (2005).
Jones, *J Pharm Biomed Anal* 38:840-850 (2005).
Kaempfer, *J.Gen.Microbiol.* 137:1831-1892 (1991).
Kamiya, Noriho, et al., "Fluorescent substrates for covalent protein labeling catalyzed by microbial transglutaminase," *Org. Biomol. Chem.* 7:3407-3412 (2009).
Kamiya, Noriho, et al., "New Fluorescent Substrates of Microbial Transglutaminase and Its Application to Peptide Tag-Directed Covalent Protein Labeling," *Bioconjugation Protocols: Strategies and Methods*, Methods in Molecular Biology, vol. 751, Chapter 7, Sonny S. Mark (ed.), pp. 81-94 (2011).
Kandil et al., *Glvcoconi J* 14:13-17. (1997).
Kim et al., *Biochemical Engineering Journal* 16:163-8 (2003).
Konadu et al., *Infect. Immun.* 62:5048-5054 (1994).
Kreis et al., *Int J Biol Macromol.* 17(3-4):117-30 (1995).
Lefeber et al., *C em. Eur. J.* 7(20):4411-4421 (2001).
Lemercinier and Jones, *Carbohydrate Res.* 296:83-96 (1996).
Lewis et al., *PNAS USA* 101:11123-8 (2004).
Lindberg, *Vaccine* 17 Suppl 2:S28-36 (1999).
Mei et al., *Carbohvdr Res.* 340:2345-2351 (2005).
Michon et al., *Clin Vaccine Immunol.* 13(8):936-43 (2006).
Mumenthaler et al., *Phann. Res.* 11:12-20 (1994).
Nicolaou et al., *J. Am. Chem. Soc.* 119:449-450 (1997).
Nilsson & Svensson, *Carbohydrate Research* 69:292-296 (1979).
Ning et al., *Tetrahedron Letters* 43:5545-5549 (2002).
Ohno et al., *Carbohydrate Research* 316:161-172 (1999).
Pang et al., *Biosci Biotechnol Biochem* 69:553-8 (2005).
Ramsay et al., *Lancet* 357(9251):195-196 (2001).
Ravenscroft et al., *Vaccine* 17:2802-2816 (1999).
Read et al., *Carbohydr Res.* 281:187-201 (1996).
Roser, *Biopharm.* 4:47-53 (1991).
Sato, *Adv. Drug Delivery Rev.* 54:487-504 (2002).
Takeo and Tei, *Carbohvdr Res.* 145:293-306 (1986).
Takeo et al., *Carbohydr Res.* 245:81-96 (1993).
Tanaka et al., *Tetrahedron Letters* 44:3053-3057 (2003).
Wada, *Biotech. Lett.* 23:1367-1372 (2001).
Wessels et al., *Infect Immun* 57:1089-94 (1989).
Williams and Polli, *J. Parenteral Sci. Technol.* 38:48-59 (1984).
Wu et al., *Carbohvdr Res.* 338:2203-12 (2003).
Yamada et al., *Tetrahedron Letters* 40:4581-4584 (1999).
Yamago et al., *Org. Lett.* 3(24):3867-3870 (2001).
Yin, Zhaojun, et al., "Boosting Immunity to Small Tumor-Associated Carbohydrates with Bacteriophage Q# Capsids," ACS Chemical Biology, downloaded from http://pubs.acs.org, 8(6):1253-1262 (Mar. 2013).

* cited by examiner 1 2 3 4 5

SEQUENCE LISTING

```
<160> NUMBER OF SEQ ID NOS: 2

<210> SEQ ID NO 1
<211> LENGTH: 535
<212> TYPE: PRT
<213> ORGANISM: Corynebacterium diphtheriae

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365
```

-continued

Gln Val Val His Asn Ser Tyr Asn Arg Pro Ala Tyr Ser Pro Gly His
370 375 380

Lys Thr Gln Pro Phe Leu His Asp Gly Tyr Ala Val Ser Trp Asn Thr
385 390 395 400

Val Glu Asp Ser Ile Ile Arg Thr Gly Phe Gln Gly Glu Ser Gly His
405 410 415

Asp Ile Lys Ile Thr Ala Glu Asn Thr Pro Leu Pro Ile Ala Gly Val
420 425 430

Leu Leu Pro Thr Ile Pro Gly Lys Leu Asp Val Asn Lys Ser Lys Thr
435 440 445

His Ile Ser Val Asn Gly Arg Lys Ile Arg Met Arg Cys Arg Ala Ile
450 455 460

Asp Gly Asp Val Thr Phe Cys Arg Pro Lys Ser Pro Val Tyr Val Gly
465 470 475 480

Asn Gly Val His Ala Asn Leu His Val Ala Phe His Arg Ser Ser Ser
485 490 495

Glu Lys Ile His Ser Asn Glu Ile Ser Ser Asp Ser Ile Gly Val Leu
500 505 510

Gly Tyr Gln Lys Thr Val Asp His Thr Lys Val Asn Ser Lys Leu Ser
515 520 525

Leu Phe Phe Glu Ile Lys Ser
530 535

<210> SEQ ID NO 2
<211> LENGTH: 535
<212> TYPE: PRT
<213> ORGANISM: Corynebacterium diphtheriae

<400> SEQUENCE: 2

Gly Ala Asp Asp Val Val Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Glu Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly

-continued

```
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535
```

SITE-SPECIFIC CHEMOENZYMATIC PROTEIN MODIFICATIONS

FIELD OF THE INVENTION

The present invention relates generally to a novel method of introducing modifying groups to a protein. In particular, the present invention relates to the selective derivation of lysine residues in proteins using a chemoenzymatic microbial transglutaminase-mediated reaction for modifying proteins and methods for their preparation and use.

BACKGROUND

It is well-known that the properties and characteristics of proteins may be modified by conjugating groups to the protein. For example, U.S. Pat. No. 4,179,337 disclosed proteins conjugated to polyethylene or polypropylene glycols. Generally, such conjugation generally requires some functional group in the protein to react with another functional group in a conjugating group. Amino groups, such as the N-terminal amino group or the ε-amino group in lysine residues have been used in combination with suitable acylating reagents for this purpose. It is often desired or necessary to control the conjugation reaction, such as where the conjugating compounds are attached to the protein and to control how many conjugating groups are attached. This is often referred to as specificity or selectivity.

Site-specific modification of proteins is a longstanding challenge in the pharmaceutical and biotechnology arts. The classic methods oftentimes lead to non-specific labeling (e.g. NHS Lys labeling) or require engineering (e.g. maleimide Cys labeling or unnatural amino acids). In addition, the repertoire of selective chemical reactions, however, is very limited. One alternative is, by recombinant methods, to introduce special unnatural amino acids having a unique reactivity and then exploit this reactivity in the further derivatization. Another alternative is the use of enzymes which recognize structural and functional features of the protein to be modified. An example of this is the use of microbial transglutaminase (mTGase) to selectively modify Gln residues in growth hormone. Other documents disclose the use of transglutaminase to alter the properties of physiologically active proteins. See e.g. EP 950 665, EP 785 276 and Sato, Adv. Drug Delivery Rev., 54, 487-504 (2002), which disclose the direct reaction between proteins comprising at least one Gln and amine-functionalized PEG or similar ligands in the presence of transglutaminase; see also Wada in Biotech. Lett., 23, 1367-1372 (2001), which discloses the direct conjugation of P-lactoglobulin with fatty acids by means of transglutaminase. The reaction catalyzed by the transglutaminase is a transamidation reaction in which the primary amide of the glutamine residue is converted to a secondary amide from a primary amine present in the reaction mixture.

The selective derivatization of proteins remains a very difficult task; the derivatization of lysines in a protein by acylation is an even more inherently non-selective process. Thus, there is at present no efficient method for the selective derivatization of lysine residues. Accordingly, there is a need in the art for methods of selectively derivatizing amino acid residues such as lysine in proteins or polypeptides.

SUMMARY

In one aspect, a method for modifying a protein is disclosed. The method permits site selective modifications. The method includes providing a target protein having at least one lysine residue; contacting the target protein with a modifying compound having the formula $R^1$-(Leu)$_x$-Gln-(Gly)$_y$-(A-W—B—$R^2$)$_z$ in the presence of a microbial transglutaminase to form a modified protein;

wherein x is 0 or 1; y is 0 or 1; z is 0 or 1;

$R^1$ is selected from the group consisting of: acetyl,

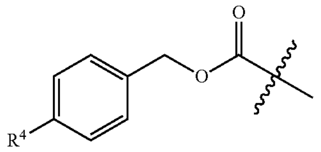

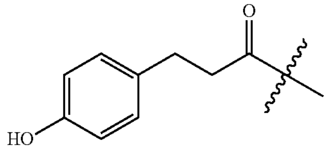

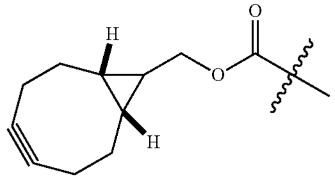

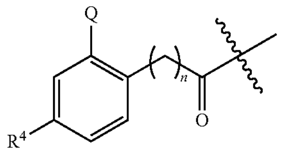

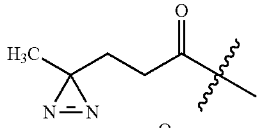

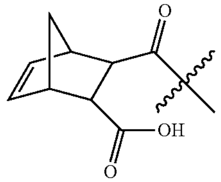

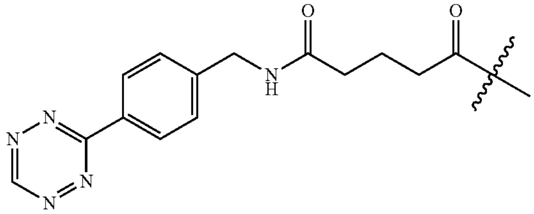

and

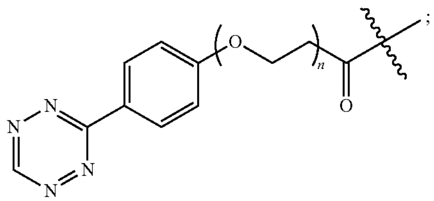

wherein each $R^4$ is selected from —H, —$N_3$, and

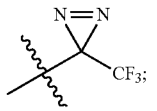 [SMILES: *C1(C(F)(F)F)N=N1]

W is selected from: $C_1$-$C_6$ linear or branched alkyl or polyethylene glycol having a molecular weight of between about 40 and about 80,000 amu;

A is absent or selected from —O—, —NH—, and —S—;

B is absent or selected from —O—, —C(O)—, —NH—, —C(O)NH—, —NHC(O)—, —NHC(O)O—, —OC(O)NH—, —OC(O)O—, —C═N(OH)—, —$S(O_2)$—, —$NHS(O_2)$—, —$S(O_2)NH$—, —S(O)—, —NHS(O)—, —S(O)NH—; —C(O)O—, —OC(O)—, —S—, ═NH—O—, ═NH—NH— and ═NH—N($C_1$-$C_{20}$alkyl)-;

$R^2$ is selected from the group consisting of: a fatty acid, linear or branched $C_1$-$C_3$ alkyl-$N_3$, cyclooctynyl, fluorophore, polysaccharide, —$CH(OCH_3)_2$,

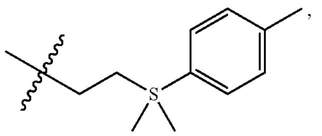

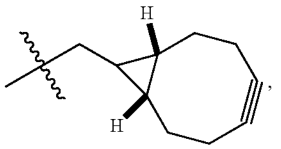

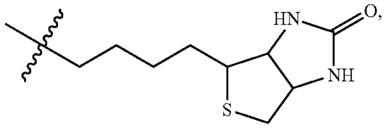

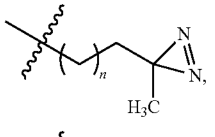

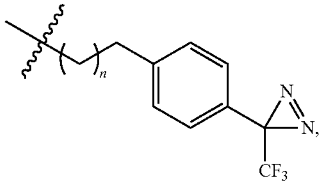

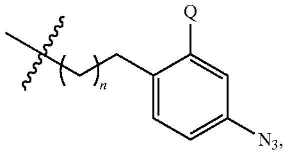

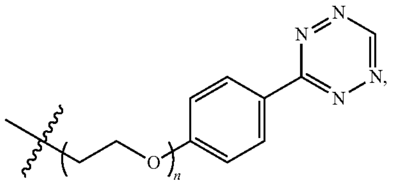

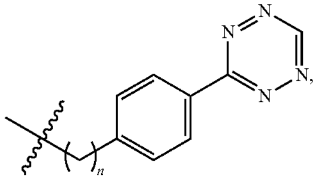

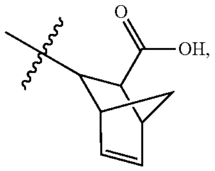 and

-continued

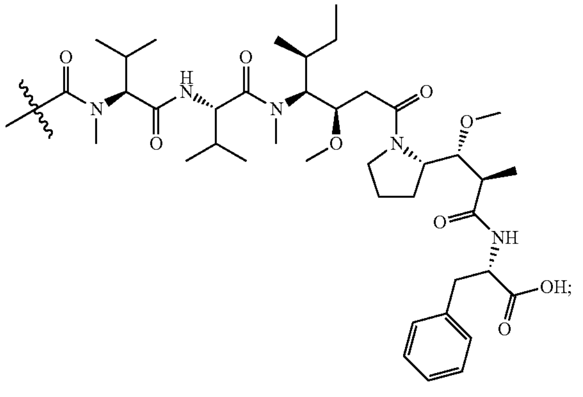 [SMILES: *C(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

each n is an integer independently selected from 0 to 6;

each Q is selected from H and —$NO_2$.

In some embodiments, the method also includes controlling the pH environment of the target protein to a pH greater than 7; and contacting the modified protein with a molecule having a cysteine residue.

In some embodiments, the molecule having cysteine residue is $N^5$—((R)-1-((carboxymethyl)amino)-3-mercapto-1-oxopropan-2-yl)-L-glutamine.

In some embodiments, microbial transglutaminase is Ajinomoto microbial transgluaminase TI. In some embodiments, the protein is a carrier protein. In some embodiments, the protein is $CRM_{197}$. In some embodiments, the protein is selected from: bacterial toxin, bacterial toxin fragments, detoxified bacterial toxins, antibodies, and antibody fragments.

In some embodiments, the method includes reacting the $R_1$ group with a biointeractive agent or an analytical agent.

In some embodiments, the method includes reacting the $R^2$ group with a biointeractive agent or an analytical agent. In some embodiments, the analytical agent is a label. In some embodiments, the method includes detecting the label.

In another aspect, conjugate prepared by the disclosed processes are also disclosed. In another aspect, therapeutic proteins are disclosed prepared by the disclosed processes. In another aspect, imaging agents are disclosed prepared by the disclosed processes. In another aspect, labelling tools are disclosed prepared by the disclosed processes.

In another aspect, compounds of the formula $R^1$-$(Leu)_x$-Gln-$(Gly)_y$-$(A\text{-}W—B—R^2)_z$ are disclosed where $R^1$, x, y, A, W, B, $R^2$ and z have the meanings described herein.

In one aspect, a method for modifying a protein is disclosed. The method includes providing a target protein having at least one lysine residue; contacting the target protein with a modifying compound having the formula $R^1$-$(Leu)_x$-Gln-$(Gly)_y$-$(NH—W—R^2)_z$ in the presence of a microbial transglutaminase, wherein x is 0 or 1; y is 0 or 1; z is 0 or 1; $R^1$ is selected from the group consisting of: acetyl,

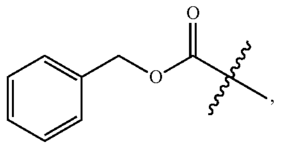

-continued

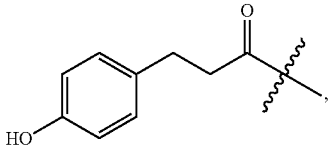

, and

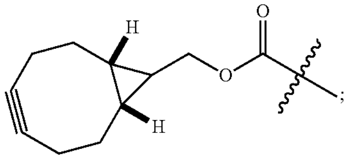

W is selected from $C_1$-$C_6$ linear or branched alkyl or polyethylene glycol having a molecular weight of between about 40 and about 80,000 amu;

$R^2$ is selected from the group consisting of: linear or branched $C_1$-$C_3$ alkyl-$N_3$, cyclooctynyl, fluorophore, polysaccharide,

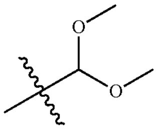

,

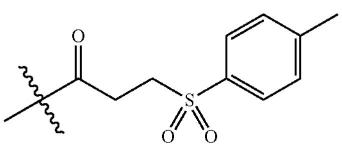

,

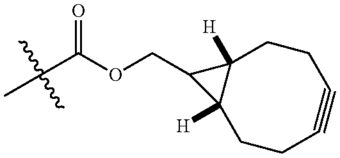

, and

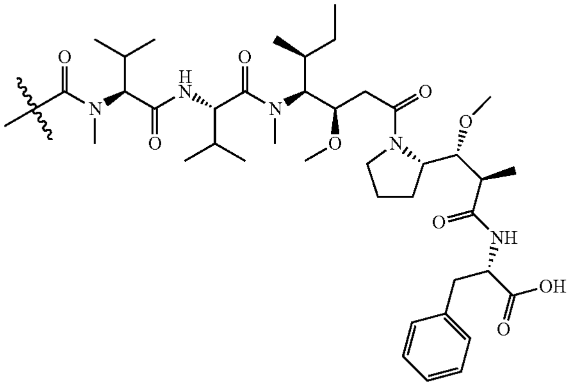

to form a modified protein.

In some embodiments, x is 1. In some embodiments, $R^1$ is selected from acetyl,

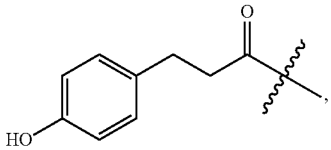

, and

-continued

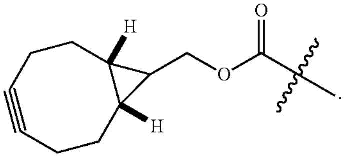

In some embodiments, $R^1$ is acetyl. In some embodiments, $R^1$ is

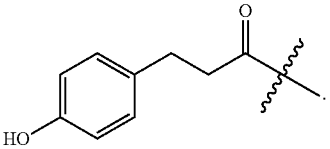 [SMILES: *C(=O)CCc1ccc(O)cc1]

In some embodiments, $R^1$ is

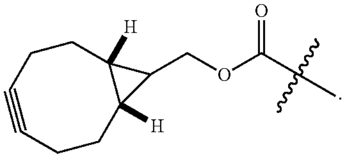 [SMILES: *C(=O)OCC1[C@H]2CCC#CCC[C@@H]12]

In some embodiments, y is 1 and z is 0. In some embodiments, wherein y is 1 and z is 1.

In some embodiments, W is selected from $C_1$-$C_6$ linear or branched alkyl. In some embodiments, W is $C_2$ linear alkyl. In some embodiments, $R^2$ is

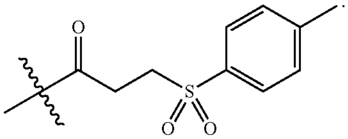 [SMILES: *C(=O)CCS(=O)(=O)c1ccc(C)cc1]

In some embodiments, x is 0, y is 1, and $R^1$ is

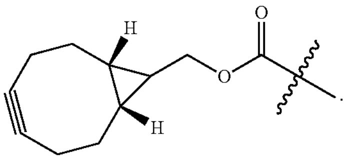 [SMILES: *C(=O)OCC1[C@H]2CCC#CCC[C@@H]12]

In some embodiments, wherein x is 0 and $R^1$ is

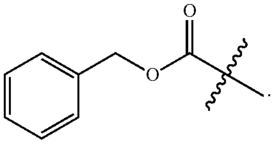 [SMILES: *C(=O)OCc1ccccc1]

In some embodiments, y is 0 and z is 1. In some embodiments, y is 1 and z is 1.

In some embodiments, W is $C_1$-$C_6$ linear or branched alkyl. In some embodiments, W is $C_2$ linear alkyl. In some embodiments, W is $C_5$ linear alkyl. In some embodiments, W is linear or branched polyethylene glycol having a molecular weight of between about 40 and about 3000 amu. In some embodiments, W is linear polyethylene glycol having a molecular weight of between about 40 and about 80 amu.

In some embodiments, $R^2$ is linear or branched $C_1$-$C_3$ alkyl-$N_3$. In some embodiments, $R^2$ is $C_2$-alkyl-$N_3$. In some embodiments, $R^2$ is cyclooctynyl. In some embodiments, $R^2$ is

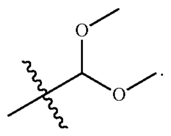 [SMILES: *C(OC)OC]

In some embodiments, $R^2$ is

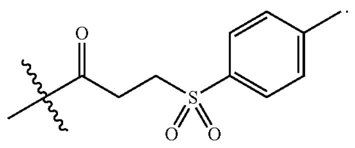 [SMILES: *C(=O)CCS(=O)(=O)c1ccc(C)cc1]

In some embodiments, $R^2$ is a fluorophore. In some embodiments, the flurophore is selected from: alexa 647, alexa 750, alexa 488, Cy5, Cy7, rhodamine, and fluorescein. In some embodiments the fluorophore is of the formula

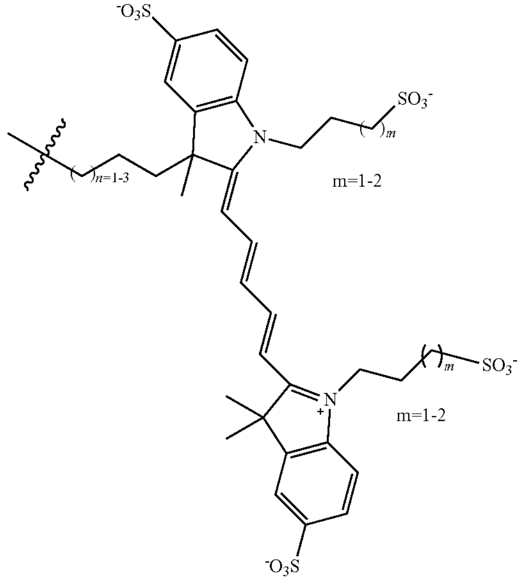

where n is from 1 to 3 and each m is from 1 to 2. In some embodiments, n is 1. In some embodiments, n is 2. In some embodiments, n is 3. In some embodiments, one m is 1 and the other m is 2. In some embodiments, both m's are 1. In some embodiments, both m's are 2. In some embodiments, $R^2$ is

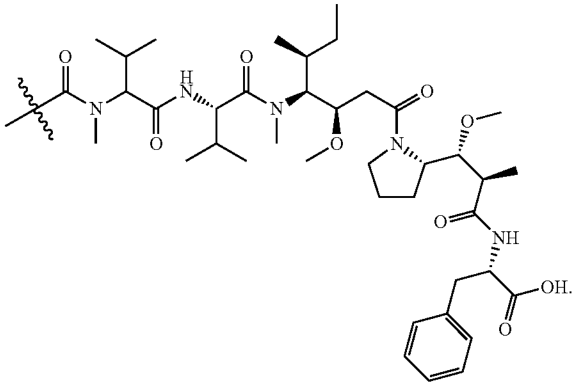

In some embodiments, $R^2$ is a polysaccharide. In some embodiments, the polysaccharide is selected from GBSII, GBSV, and MenA. In some embodiments, $R^2$ is GBSII. In some embodiments, $R^2$ is GBSV. In some embodiments, $R^2$ is MenA.

In some embodiments, the method includes controlling the pH environment of the target protein to a pH greater than 7; and contacting the modified protein with a molecule having a cysteine residue. In some embodiments, the molecule having a cysteine residue is $N^5$—((R)-1-((carboxymethyl)amino)-3-mercapto-1-oxopropan-2-yl)-L-glutamine.

In some embodiments, the microbial transglutaminase is Ajinomoto microbial transgluaminase TI.

In some embodiments, the protein is a carrier protein. In some embodiments, the protein is $CRM_{197}$. In some embodiments, the protein is selected from: bacterial toxin, bacterial toxin fragments, detoxified bacterial toxins, antibodies, and antibody fragments.

In some embodiments, the method also includes reacting the $R_1$ group with a biointeractive agent or an analytical agent. In some embodiments, the method includes reacting the $R^2$ group with a biointeractive agent or an analytical agent. In some embodiments, the analytical agent is a label. In some embodiments, the method also includes detecting the label.

In another aspect, a conjugate is disclosed that is prepared from the methods disclosed herein. In another aspect, a vaccine is disclosed that is prepared with a conjugate or a modified protein disclosed herein. In another aspect, a therapeutic protein is disclosed having a modified protein disclosed herein. In another aspect, an imaging agent is disclosed having a modified protein disclosed herein. In another aspect, a labeling tool is disclosed having modified protein disclosed herein.

In another aspect, compound of the formula $R^1$-$(Leu)_x$-Gln-$(Gly)_y$-$(NH—W—R^2)_z$ are disclosed wherein x is 0 or 1; y is 0 or 1; z is 0 or 1; $R^1$ is selected from the group consisting of: acetyl,

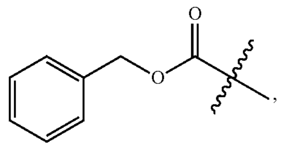

-continued
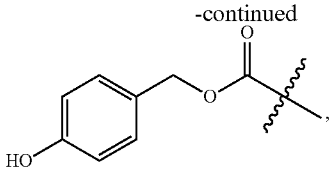
, and
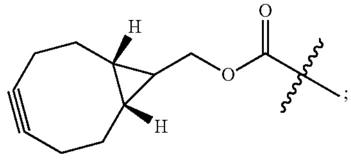
;
W is selected from $C_1$-$C_6$ linear or branched alkyl or polyethylene glycol having a molecular weight of between about 40 and about 80,000 amu; $R^2$ is selected from the group consisting of: linear or branched $C_1$-$C_3$ alkyl-$N_3$, cyclooctynyl, fluorphore, polysaccharide,
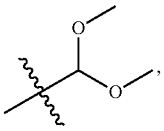
,
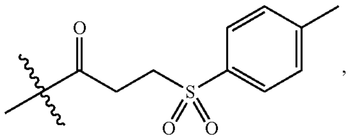
,
-continued
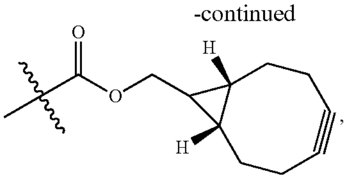
, and
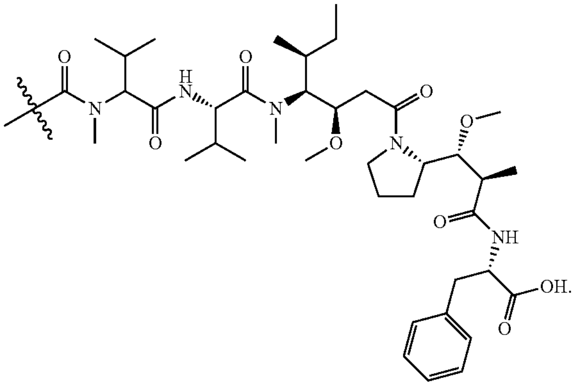 [SMILES: *C(=O)N(C)C(C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]
In some embodiments, the compound is selected from the group consisting of:
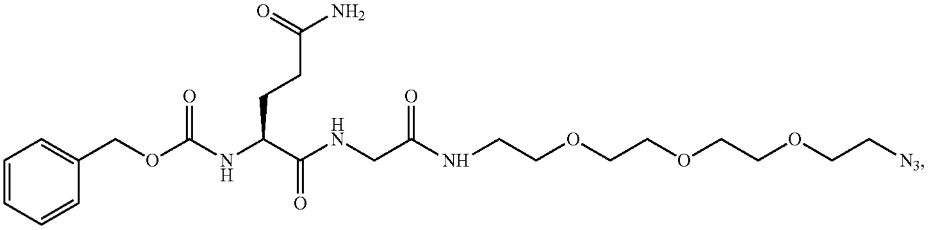
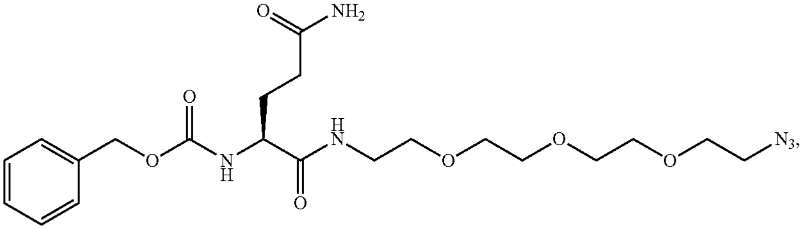
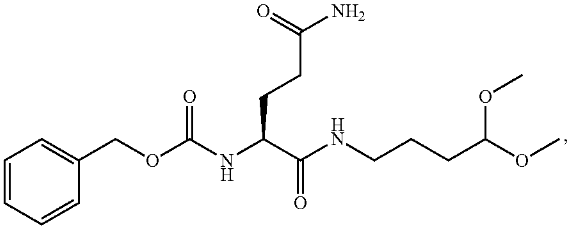
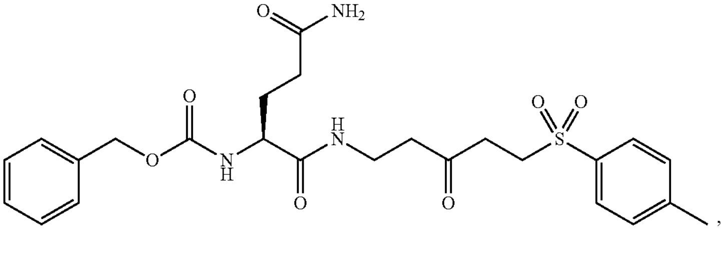

-continued
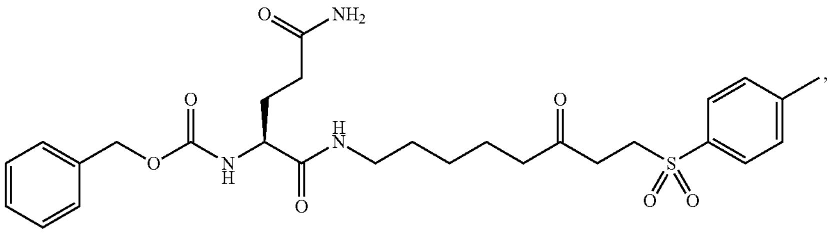
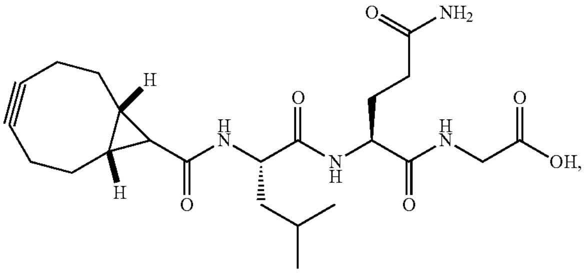
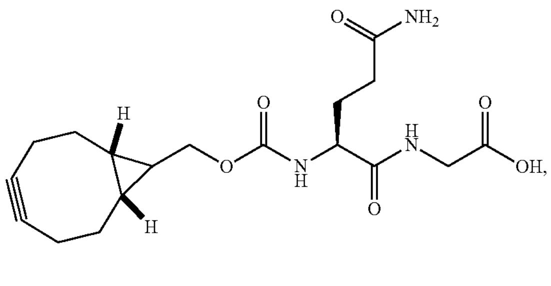
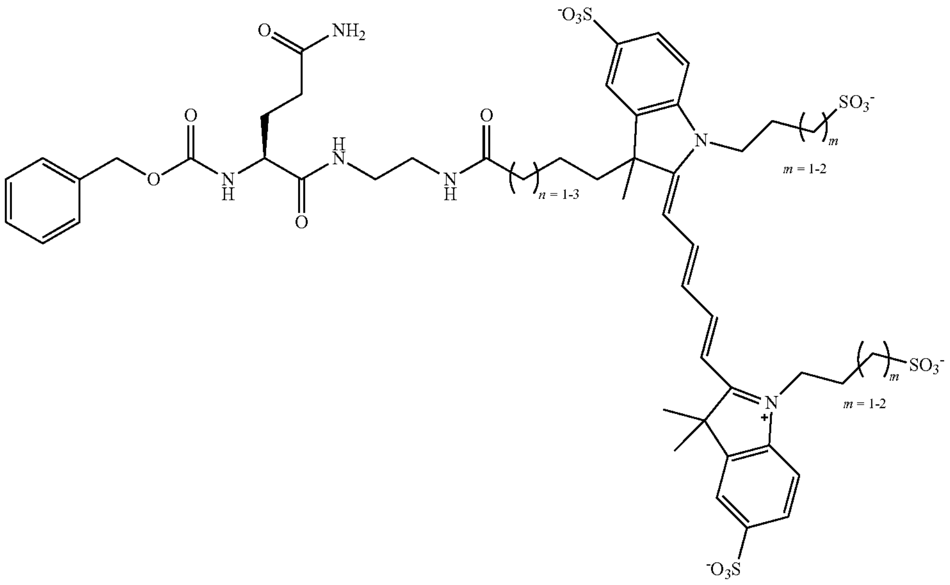
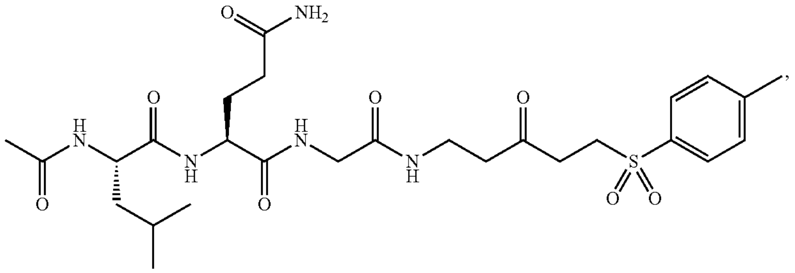
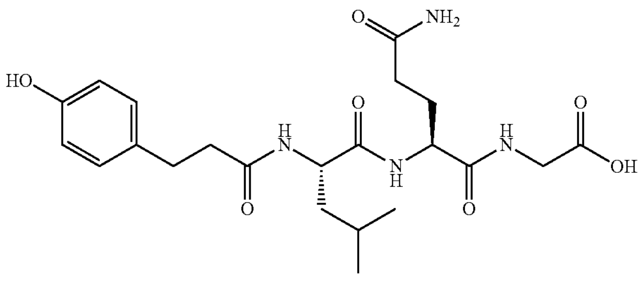

-continued
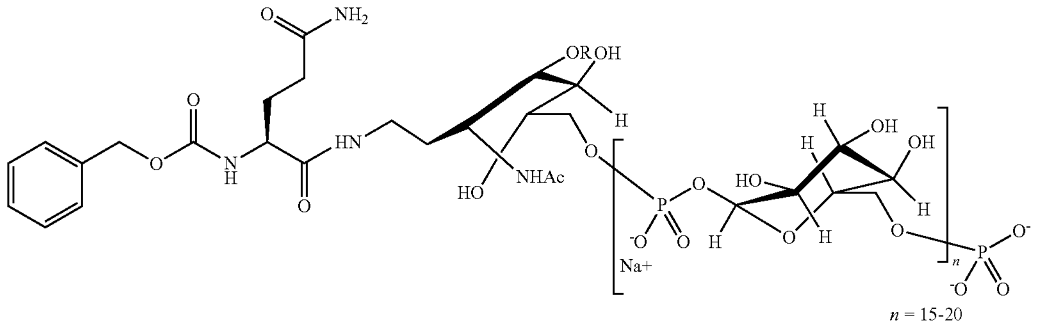
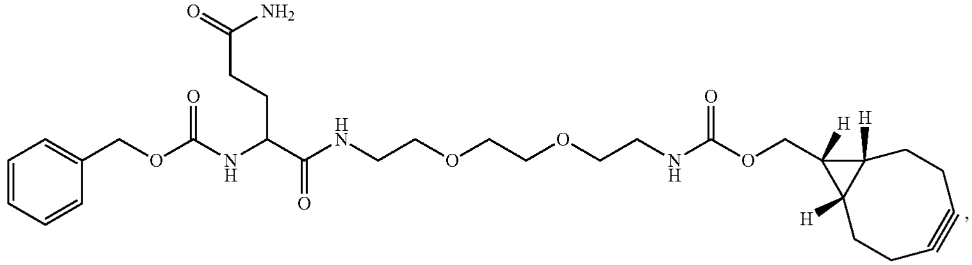
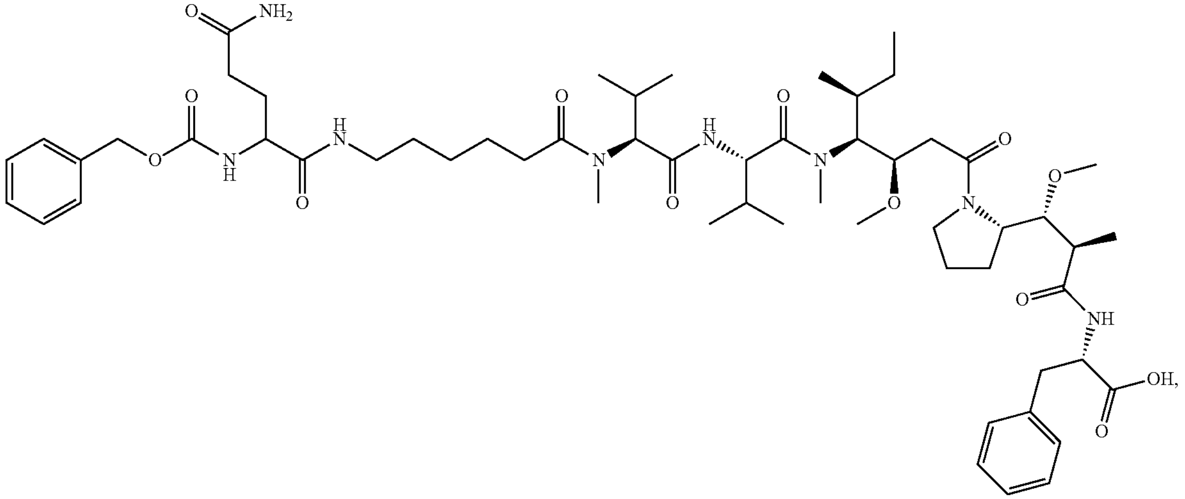
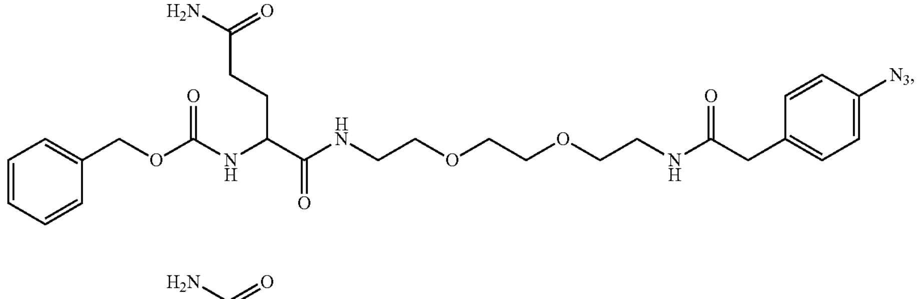
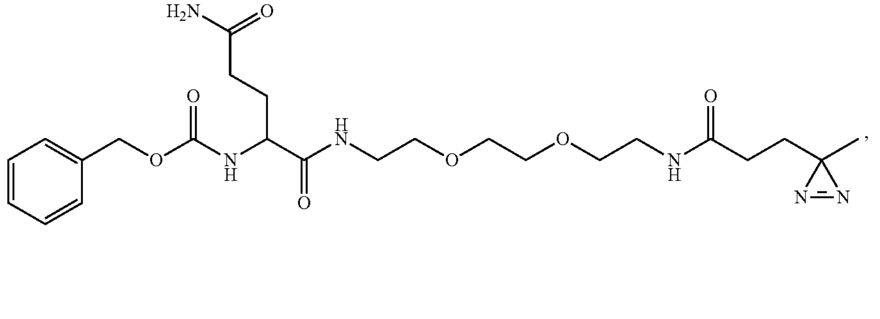

-continued

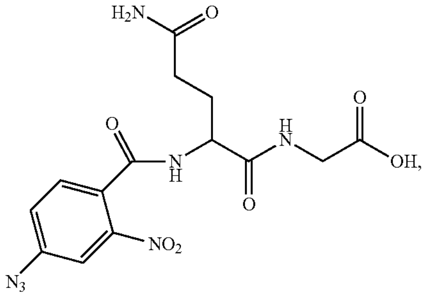

,

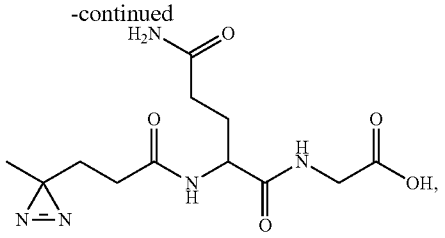

,

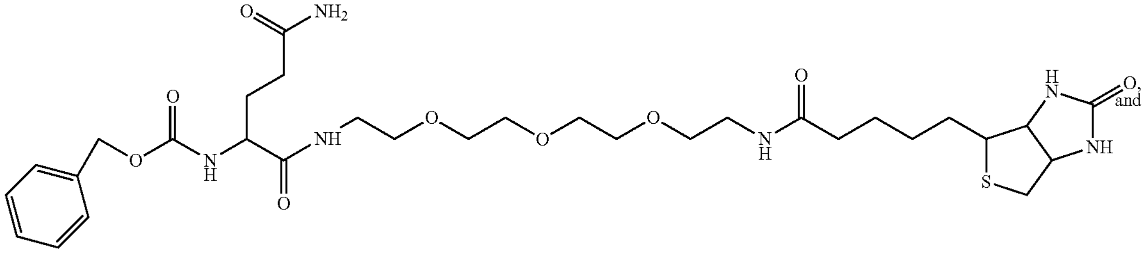

and

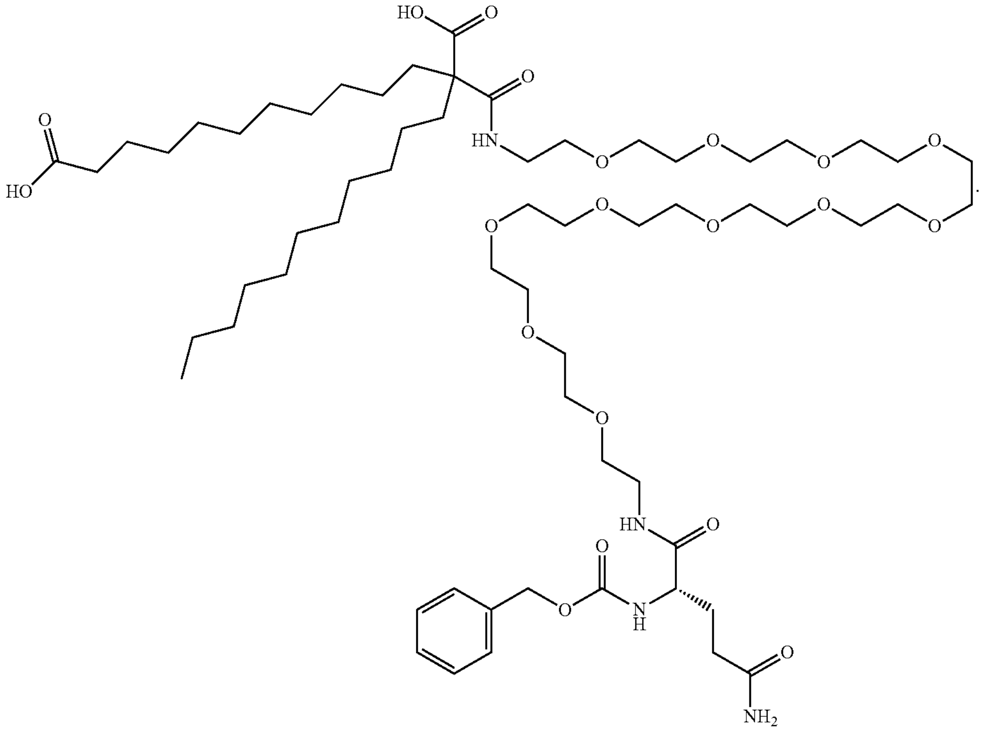

.

In some embodiments, a conjugate of a compound is disclosed wherein the conjugate includes a conjugate protein and a compound disclosed herein. In some embodiments, the conjugate protein is $CRM_{197}$. In some embodiments, the conjugate protein is $GBS_{80}$.

In some embodiments, a vaccine is disclosed comprising a conjugate disclosed herein.

DETAILED DESCRIPTION

All references made to patents, patent publications, and other literature are made for their incorporation into this disclosure to the extent permissible by law.

Figure 1:
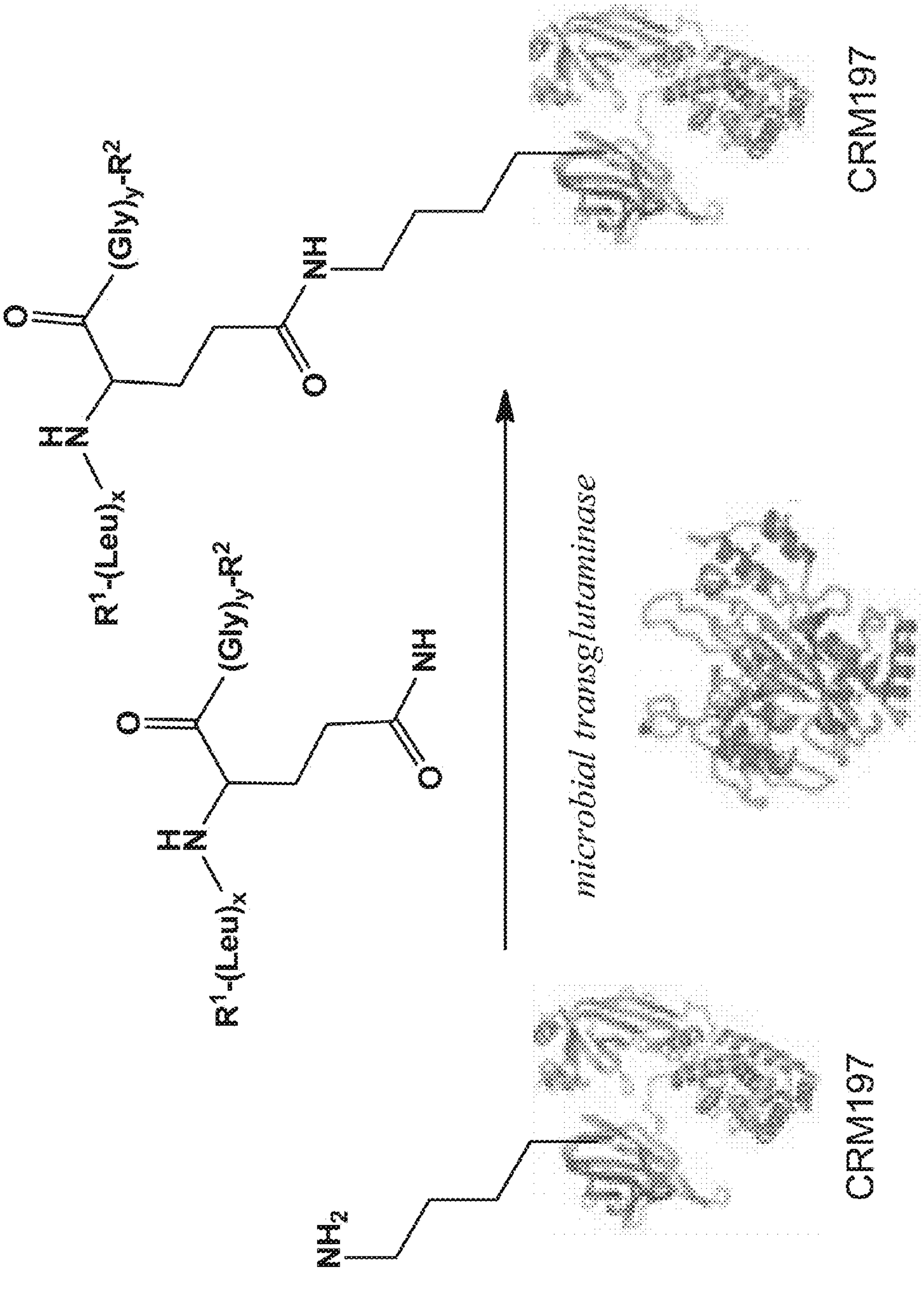
FIG. 1 is a synthetic scheme depicts the addition of a protein modifying group reacting with a protein (CRM197) catalyzed by microbial transglutaminase.

The present invention addresses the aforementioned needs by providing a method of introducing modifying compounds to a target protein in a selective manner via reaction with a modifying compound, while using conventional chemical methods. The method is generally depicted in FIG. 1. A lysine residue from a target protein (for example $CRM_{197}$) reacts with a glutamine residue (Gln) from a modifying compound of formula (I): $R^1$-(Leu)$_x$-Gln-(Gly)$_y$-(A-W—B—$R^2$)$_z$ or of formula (II): $R^1$-(Leu)$_x$-Gln-(Gly)$_y$-(NH—W—$R^2$)$_z$. The resulting product is a protein having one or more groups capable of further chemical functionalization.

In one aspect, a process for modifying a protein includes: (a) forming an activated complex between an auxiliary protein and a modifying compound by catalytic action of microbial transglutaminase; (b) transferring the modifying compound from the activated complex to a target protein thereby creating a modified protein. As such, a "modified protein" as used herein, refers to a protein or polypeptide that has been selectively modified by addition of a modifying compound using microbial transglutaminase.

In some embodiments, the method includes a transglutaminase catalyzed reaction of a target protein having at least two lysines residues with a modifying compound. The modifying compound is a glutamine-containing protein of the formula (I): $R^1$-(Leu)$_x$-Gln-(Gly)$_y$-(A-W—B—$R^2$)$_z$ or of formula (II): $R^1$-(Leu)$_x$-Gln-(Gly)$_y$-(NH—W—$R^2$)$_z$.

In this process, an activated acyl complex is formed by reacting the glutamine residue in the modifying compound with microbial transglutaminase in order to attach the modifying compound. In one embodiment, the modifying compound is transferred by acylation to a lysine residue in the target protein. In one embodiment, $R^1$ and $R^2$ are desired substituents, where at least one of them has a chemical group that is suitable for further modification. Thus, the process involves a microbial transglutaminase reaction in order to selectively modify a lysine residue in a target protein.

As used herein, the term "amu" is an abbreviation for atomic mass units also frequently referred to as Dalton units.

As used herein, the term "polypeptide" refers to a polymer of amino acid residues joined by peptide bonds, whether produced naturally or synthetically. Polypeptides of less than about 10 amino acid residues are commonly referred to as "peptides." The term "peptide" is intended to indicate a sequence of two or more amino acids joined by peptide bonds, wherein said amino acids may be natural or unnatural. The term encompasses the terms polypeptides and proteins, which may consist of two or more peptides held together by covalent interactions, such as for instance cysteine bridges, or non-covalent interactions.

A "protein" is a macromolecule comprising one or more polypeptide chains. A protein may also comprise non-peptidic components, such as carbohydrate groups. Carbohydrates and other nonpeptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless. A protein or polypeptide encoded by a non-host DNA molecule is a "heterologous" protein or polypeptide.

An "isolated polypeptide" is a polypeptide that is essentially free from cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "biointeractive agent" as used herein refers to an organic moiety or compound that invokes a biological response when introduced into a living tissue or cell. Example of biointeractive agents include antigens, toxins, therapeutic proteins and the like. Biointeractive agents may be small molecules and macro molecules.

An "analytical agent" as used herein refers to an organic moiety or compound that can be detected by instrumental methods for qualitatively or quantitatively characterizing the material to which the analytical agent is bound or otherwise associated. Examples of such analytical agents include labels for example fluorophores or radio labels.

As used herein, the term "alkyl" is a $C_1$-$C_{45}$ alkyl group which is linear or branched. In some embodiments, alkyl is from $C_1$-$C_{20}$. In some embodiments, alkyl is from $C_1$-$C_{12}$. In some embodiments, alkyl is from $C_1$-$C_6$. Where alkyl is defined as a group, such as W in formulas I and II discussed herein, it should be understood that the group may also be known as alkylene such that there is one substitution with an adjoining group or two substitutions between two adjoining groups.

As used herein, the term "polyethylene glycol" or "PEG" refers to a polyether compound with a repeating (O—$CH_2$—$CH_2$)$_n$ subunit having a molecular weight of between about 40 and about 80,000 amu where n is an integer representing the number of repeated ether subunits. Where polyethylene glycol is defined as a group, such as W in formulas I and II discussed herein, it should be understood that there is one substitution with an adjoining group in which case there may be a free alcohol group at a terminus or two substitutions between two adjoining groups.

Transglutaminase

As mentioned above, a catalyst must be used for covalently linking the modifying compound to the target protein. The catalyst must be a microbial transglutaminase (also interchangeably referred to herein as "mTGase"). The catalyst is also known as protein-glutamine-γ-glutamyltransferase from microbial sources and catalyzes the acyl transfer reaction between the γ-carboxyamido group of a glutamine (Gln) residue in protein or a protein chain and the ϵ-amino group of a lysine (Lys) residue or various alkylamines.

The transglutaminase to be used in the methods of the present invention can be obtained from various microbial origins with no particular limitation. Examples of useful microbial transglutaminases include transglutaminases, such as from *Streptomyces mobaraense, Streptomyces cinnamoneum*, and *Streptomyces griseocarneum* (all disclosed in U.S. Pat. No. 5,156,956, which is incorporated herein by reference), and *Streptomyces lavendulae* (disclosed in U.S. Pat. No. 5,252,469, which is incorporated herein by reference) and *Streptomyces ladakanum* (JP2003199569, which is incorporated herein by reference). It should be noted that members of the former genus *Streptoverticillium* are now included in the genus *Streptomyces* [Kaempfer, J. Gen. Microbiol., 137, 1831-1892, 1991]. Other useful microbial transglutaminases have been isolated from *Bacillus subtilis* (disclosed in U.S. Pat. No. 5,731,183, which is incorporated herein by reference) and from various *Myxomycetes*. Other examples of useful microbial transglutaminases are those disclosed in WO 96/06931 (e.g. transglutaminase from *Bacilus lydicus*) and WO 96/22366, both of which are incorporated herein by reference.

Modifying Compounds

Modifying compounds that may be used in the disclosed methods are glutamine-containing proteins of the general formulas: (I): $R^1$-(Leu)$_x$-Gln-(Gly)$_y$-(A-W—B—$R^2$)$_z$ or of formula (II): $R^1$-(Leu)$_x$-Gln-(Gly)$_y$-(NH—W—$R^2$)$_z$ where Leu refers to the amino acid leucine (for example L-leucine) that is either present or absent (i.e. when x is 1 or 0, respectively); Gln refers to the amino acid glutamine (for example L-glutamine); Gly refers to the amino acid residue glycine (for example L-glycine) that is either present or absent (i.e. when y is 1 or 0, respectively).

In some embodiments, x is 0. In some embodiments, x is 1. In some embodiments, y is 0. In some embodiments y is 1. In some embodiments, z is 0. In some embodiments, z is 1.

In some embodiments, $R^1$ is acetyl. In some embodiments, $R^1$ is

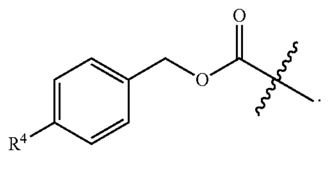

In some embodiments, $R^1$ is

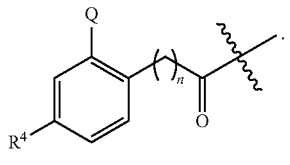

In some embodiments, Q is H. In some embodiments, Q is —$NO_2$. In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, $R^4$ is H. In some embodiments, $R^4$ is —$N_3$. In some embodiments, $R^4$ is

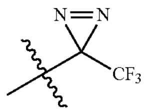 [SMILES: *C1(C(F)(F)F)N=N1]

In some embodiments, $R^1$ is

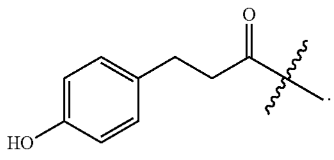 [SMILES: *C(=O)CCc1ccc(O)cc1]

In some embodiments, $R^1$ is

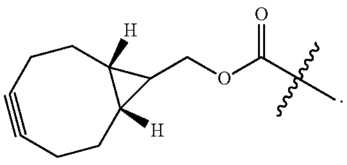 [SMILES: *C(=O)OCC1[C@H]2CCC#CCC[C@@H]12]

In some embodiments, $R^1$ is

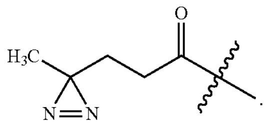 [SMILES: *C(=O)CCC1(C)N=N1]

In some embodiments, $R^1$ is

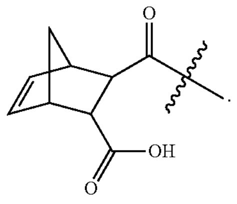 [SMILES: *C(=O)C1C2C=CC(C2)C1C(=O)O]

In some embodiments, $R^1$ is

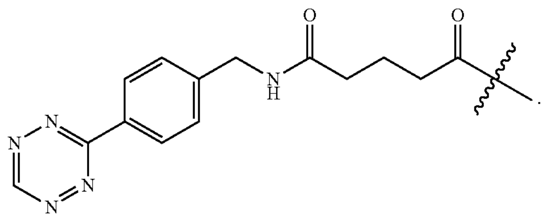 [SMILES: *C(=O)CCCC(=O)NCc1ccc(-c2nncnn2)cc1]

In some embodiments, $R^1$ is

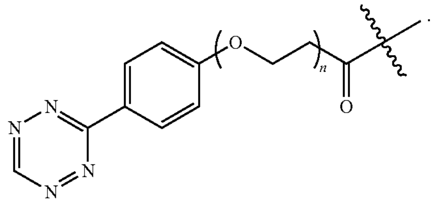

In some embodiments, W is $C_1$-$C_6$ linear or branched alkyl. In some embodiments, W is polyethylene glycol having a molecular weight of between about 40 and about 80,000 amu.

In some embodiments, A is absent. In some embodiments, A is —O—. In some embodiments, A is —NH—. In some embodiments, A is —S—.

In some embodiments, B is absent. In some embodiments, B is —O—. In some embodiments, B is —C(O)—. In some embodiments, B is —NH—. In some embodiments, B is —C(O)NH—. In some embodiments, B is —NHC(O)—. In some embodiments, B is, —NHC(O)O—. In some embodiments, B is —OC(O)NH—. In some embodiments, B is —OC(O)O—. In some embodiments, B is —C═N(OH)—. In some embodiments, B is —$S(O_2)$—. In some embodiments, B is —$NHS(O_2)$—. In some embodiments, B is —$S(O_2)NH$—. In some embodiments, B is —S(O)—. In some embodiments, B is —NHS(O)—. In some embodiments, B is —S(O)NH—. In some embodiments, B is —C(O)O—. In some embodiments, B is —OC(O)—. In some embodiments, B is —S—. In some embodiments, B is ═NH—O—. In some embodiments, B is ═NH—NH—. In some embodiments, B is ═NH—N($C_1$-$C_{20}$ alkyl)-.

In some embodiments, $R^2$ is a fatty acid. In some embodiments, the fatty acid may be of the following Formulae A1, A2 or A3:

A1

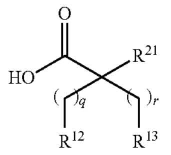

A2

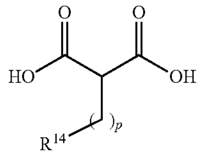

or

A3

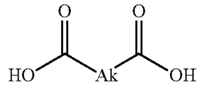

where $R^{11}$ is $CO_2H$ or H;

$R^{12}$, $R^{13}$ and $R^{14}$ are independently of each other H, OH, $CO_2H$, —CH═$CH_2$ or —C≡CH;

Ak is a branched $C_6$-$C_{30}$ alkylene;

p, q, and r are independently of each other an integer between 6 and 30;

or an amide, an ester or a pharmaceutically acceptable salt thereof.

In some embodiments, $R^2$ is linear or branched $C_1$-$C_3$ alkyl-$N_3$. In some embodiments, $R^2$ is cyclooctynyl. In some embodiments, $R^2$ is a fluorophore. In some embodiments the fluorophore is of the formula

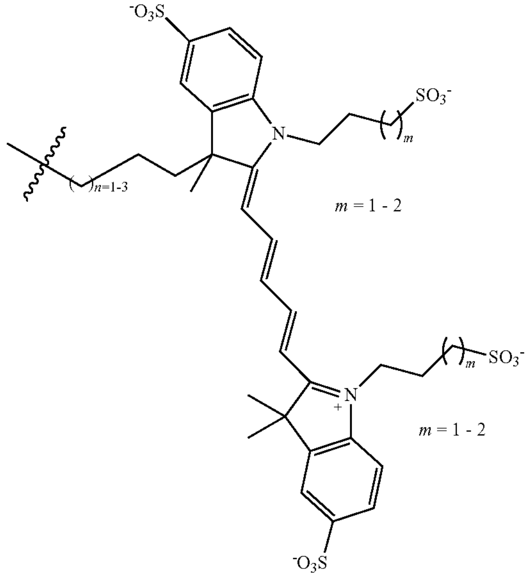

where n is from 1 to 3 and each m is from 1 to 2. In some embodiments, n is 1. In some embodiments, n is 2. In some embodiments, n is 3. In some embodiments, one m is 1 and the other m is 2. In some embodiments, both m's are 1. In some embodiments, both m's are 2. In some embodiments, $R^2$ is a polysaccharide. In some embodiments, $R^2$ is —$CH(OCH_3)_2$. In some embodiments, $R^2$ is

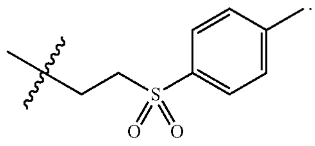 [SMILES: *CCS(=O)(=O)c1ccc(C)cc1]

In some embodiments, $R^2$ is

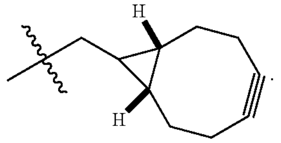 [SMILES: *CC1[C@H]2CCC#CCC[C@@H]12]

In some embodiments, $R^2$ is,

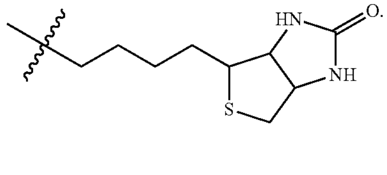 [SMILES: *CCCCC1SCC2NC(=O)NC21]

In some embodiments, $R^2$ is

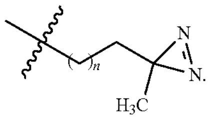

In some embodiments, $R^2$ is

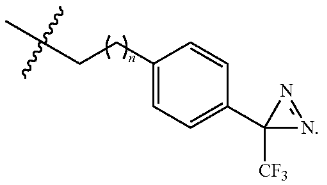

In some embodiments, $R^2$ is

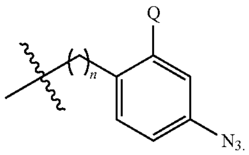

In some embodiments, Q is H. In some embodiments, Q is —$NO_2$. In some embodiments, n is 0. In some embodiments, n is from 1 to 6. In some embodiments, n is 1. In some embodiments, n is 2. In some embodiments, n is 3. In some embodiments, n is 4. In some embodiments, n is 5. In some embodiments, n is 6.

In some embodiments, $R^2$ is

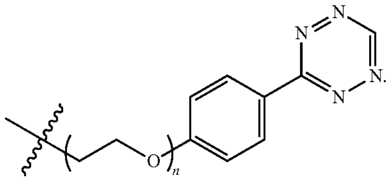

In some embodiments, n is 0. In some embodiments, n is from 1 to 6. In some embodiments, n is 1. In some embodiments, n is 2. In some embodiments, n is 3. In some embodiments, n is 4. In some embodiments, n is 5. In some embodiments, n is 6.

In some embodiments, $R^2$ is

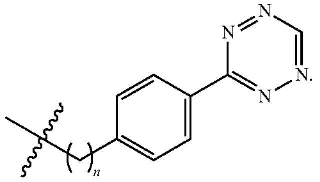

In some embodiments, n is 0. In some embodiments, n is from 1 to 6. In some embodiments, n is 1. In some embodiments, n is 2. In some embodiments, n is 3. In some embodiments, n is 4. In some embodiments, n is 5. In some embodiments, n is 6.

In some embodiments, $R^2$ is

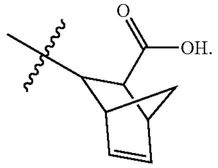 [SMILES: *C1C2C=CC(C2)C1C(=O)O]

In some embodiments, $R^2$ is

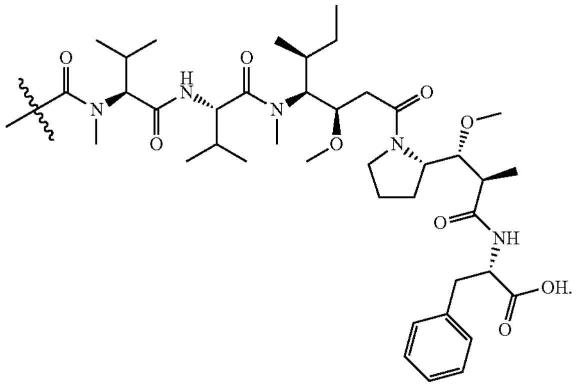 [SMILES: *C(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

In compounds of formula II, the R2 groups shown below already include some embodiments incorporating B in formula I above.

In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, $R^1$ is selected from acetyl,

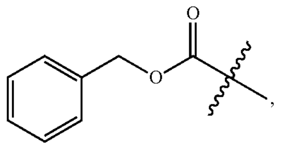

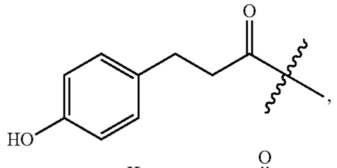

and

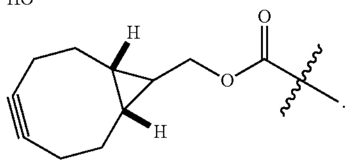

In some embodiments, $R^1$ is selected from acetyl,

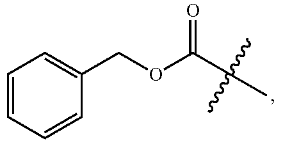

and

-continued

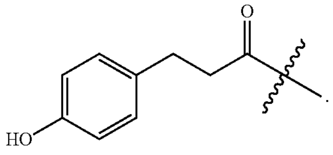

In some embodiments, $R^1$ is selected from acetyl,

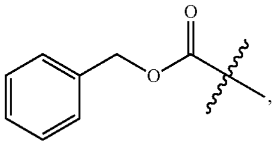

, and

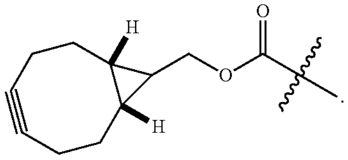

In some embodiments, $R^1$ is selected from acetyl,

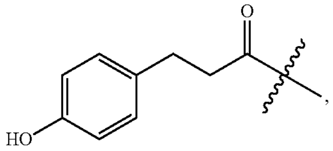

, and

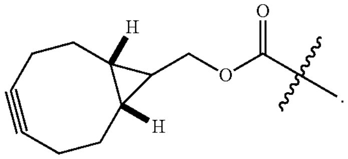

In some embodiments, $R^1$ is selected from

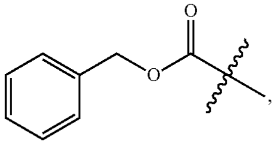

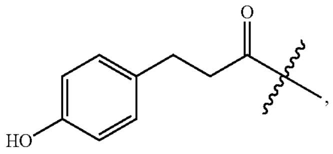

, and

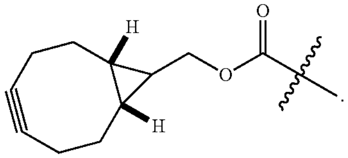

In some embodiments, $R^1$ is selected from acetyl and

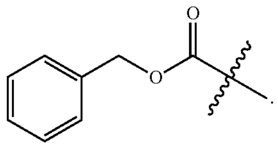 [SMILES: *C(=O)OCc1ccccc1]

In some embodiments, $R^1$ is selected from acetyl and

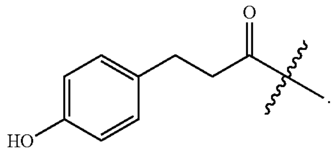 [SMILES: *C(=O)CCc1ccc(O)cc1]

In some embodiments, $R^1$ is selected from acetyl and

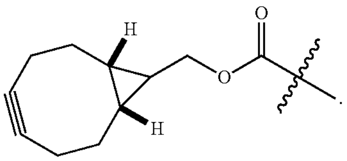 [SMILES: *C(=O)OCC1[C@H]2CCC#CCC[C@@H]12]

In some embodiments, $R^1$ is selected from

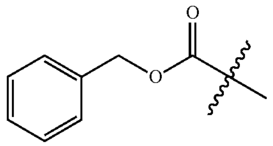

and

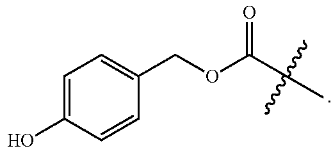

In some embodiments, $R^1$ is selected from acetyl,

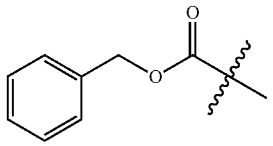

and

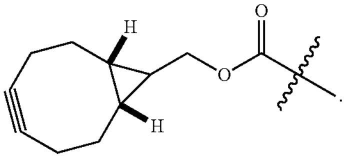

In some embodiments, $R^1$ is selected from

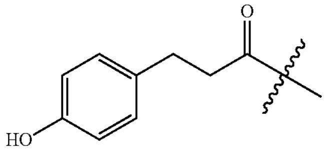

and

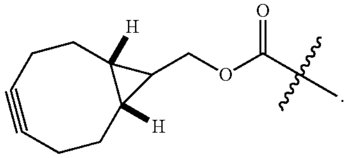

.

In some embodiments, $R^1$ is acetyl. In some embodiments, $R^1$ is

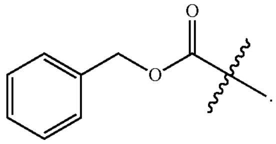 [SMILES: *C(=O)OCc1ccccc1]

.

In some embodiments, $R^1$ is,

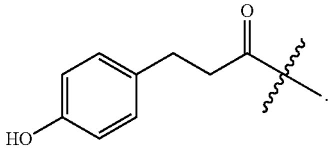 [SMILES: *C(=O)CCc1ccc(O)cc1]

.

In some embodiments, $R^1$ is

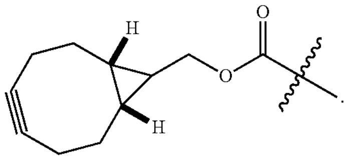 [SMILES: *C(=O)OCC1[C@H]2CCC#CCC[C@@H]12]

.

In addition, a multifunctional group A-W—B—$R^2$ or NH—W—$R^2$ may be present or absent (i.e. when z is 1 or 0, respectively). In embodiments having NH—W—$R^2$, W is selected from $C_1$-$C_6$ linear or branched alkyl or linear or branched polyethylene glycol having a molecular weight of between about 40 and about 80,000 amu. In some embodiments, W is selected from $C_1$-$C_6$ linear alkyl. In some embodiments, W is selected from $C_1$-$C_6$ branched alkyl. In some embodiments, W is selected from linear polyethylene glycol having a molecular weight of between about 40 and about 10,000 amu. In some embodiments, W is selected from linear polyethylene glycol having a molecular weight of between about 40 and about 3,000 amu. In some embodiments, W is selected from linear polyethylene glycol having a molecular weight of between about 40 and about 80 amu. In some embodiments, W is selected from linear or branched polyethylene glycol having a molecular weight of between about 2,000 and about 80,000 amu. In some embodiments, the polyethylene glycol is functionalized with a heteroatom (such as oxygen, nitrogen, or sulfur) capable reacting with a reagent to form a bond with another heteroatom, carbon, carbonyhl, sulfonyl, thionyl, and the like.

In embodiments having A-W—B—$R^2$, W is selected from $C_1$-$C_6$ linear or branched alkyl or linear or branched polyethylene glycol having a molecular weight of between about 40 and about 80,000 amu. In some embodiments, W is selected from $C_1$-$C_6$ linear alkyl. In some embodiments, W is selected from $C_1$-$C_6$ branched alkyl. In some embodiments, W is selected from linear polyethylene glycol having a molecular weight of between about 40 and about 10,000 amu. In some embodiments, W is selected from linear polyethylene glycol having a molecular weight of between about 40 and about 3,000 amu. In some embodiments, W is selected from linear polyethylene glycol having a molecular weight of between about 40 and about 80 amu. In some embodiments, W is selected from linear or branched polyethylene glycol having a molecular weight of between about 2,000 and about 80,000 amu.

In some embodiments, A is absent. In some embodiments, A is —O—. In some embodiments, A is —NH—. In some embodiments, A is —S—.

In some embodiments, B is absent. In some embodiments, B is —O—. In some embodiments, B is —C(O)—. In some embodiments, B is —NH—. In some embodiments, B is —C(O)NH—. In some embodiments, B is —NHC(O)—. In some embodiments, B is, —NHC(O)O—. In some embodiments, B is —OC(O)NH—. In some embodiments, B is —OC(O)O—. In some embodiments, B is —C═N(OH)—. In some embodiments, B is —$S(O_2)$—. In some embodiments, B is —$NHS(O_2)$—. In some embodiments, B is —$S(O_2)NH$—. In some embodiments, B is —S(O)—. In some embodiments, B is —NHS(O)—. In some embodiments, B is —S(O)NH—. In some embodiments, B is —C(O)O—. In some embodiments, B is —OC(O)—. In some embodiments, B is —S—. In some embodiments, B is ═NH—O—. In some embodiments, B is ═NH—NH—. In some embodiments, B is ═NH—N($C_1$-$C_{20}$ alkyl)-.

In some embodiments, $R^2$ is selected from $C_1$-$C_3$ linear or branched alkyl-$N_3$, cyclooctynyl, fluorophore,

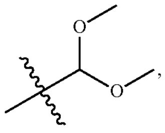

,

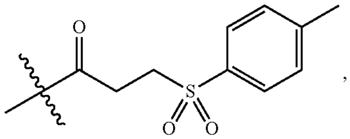

, and a polysaccharide.

In some embodiments, $R^2$ is branched or linear $C_1$-$C_3$ alkyl-$N_3$. In some embodiments, $R^2$ is branched $C_3$ alkyl-$N_3$. In some embodiments, $R^2$ is linear $C_1$-$C_3$ alkyl-$N_3$. In some embodiments, $R^2$ is $C_1$ alkyl-$N_3$. In some embodiments, $R^2$ is $C_2$ alkyl-$N_3$. In some embodiments, $R^2$ is branched $C_3$ alkyl-$N_3$.

In some embodiments, $R^2$ is cyclooctynyl. The point of attachment relative to the alkyne functionality group may be at any position so long as the alkyne can be subsequently reacted or functionalized. For example, $R^2$ can be connected to W or B at the third position, i.e.

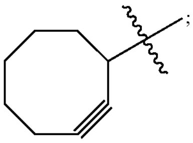 [SMILES: *C1C#CCCCCC1]

;

the fourth position, i.e.

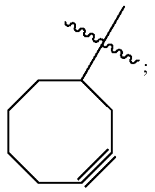 [SMILES: *C1CC#CCCCC1]

or the fifth position, i.e.

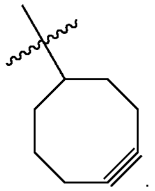 [SMILES: *C1CCC#CCCC1]

In some embodiments, $R^2$ is fluorophore. Suitable fluorophores include those that can re-emit light upon light excitation. Typically, the fluorophore contains several conjugated pi-bonds, such as are present in aromatic groups. Examples include fluorescein, rhodamine, Cy dyes such as Cy5 and Cy7, Alexa dies such as Alexa 750, Alexa 647, and Alexa 488, coumarins, and the like.

In some embodiments, $R^2$ is,

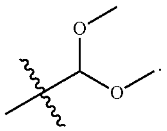 [SMILES: *C(OC)OC]

In some embodiments, $R^2$ is

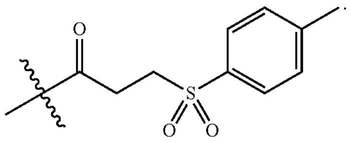 [SMILES: *C(=O)CCS(=O)(=O)c1ccc(C)cc1]

In some embodiments, $R^2$ is

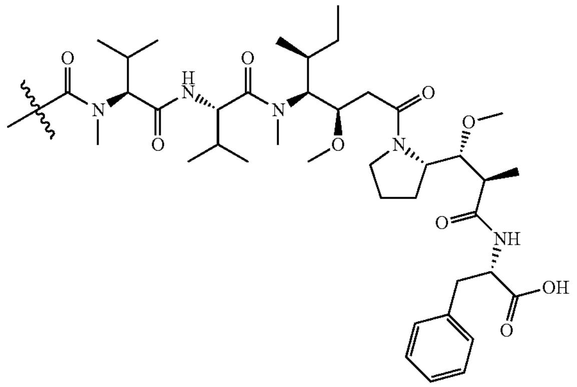 [SMILES: *C(=O)N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

which corresponds to cytotoxic MMAF connected through a carbonyl to W in NH—W—$R^2$.

When the multifunctional group A-W—B—$R^2$ or NH—W—$R^2$ is absent, then the adjacent amino acid residue whether glutamine or glycine terminates with the carboxylic acid of the residue (the C-terminus of the peptide backbone of the modifying compound).

Polysaccharides

In some embodiments, $R^2$ is polysaccharide. The polysaccharide may be any antigenic polysaccharide, particularly a polysaccharide from a pathogenic organism. Conjugates of these polysaccharides may be useful for immunizing a subject against infection caused by the pathogenic organism. Exemplary polysaccharides are described below. In particular, the polysaccharide may be a bacterial polysaccharide, e.g. a bacterial capsular polysaccharide. Representative bacterial polysaccharides are described in Table 1.

TABLE I

| Polysaccharide | Repeat Unit |
| --- | --- |
| *Haemophilus influenzae* Type b ('PRP') | →3)-β-D-Ribf-(I→1)-D-Ribitol-(5→$OPO_3$→ |
| *Neisseria meningitides* | |
| Group A | →6)-α-D-ManpNAc(3OAc)-(I→$OPO_3$→ |
| Group C | →9)-α-D-Neu5Ac(7/8OAc)-(2→ |
| Group W135 | →6)-α-D-Galp-(I→4)-α-D-Neu5Ac(9OAc)-2→ |
| Group Y | →6)-α-D-Glcp-(I→4)-α-D-Neu5Ac(9OAc)-2→ |
| *Salmonella enterica Typhi* Vi | →-α-D-GalpNacA(3OAc)-(I→ |
| *Streptococcus pneumoniae* | |
| Type 1 | →3)-D-AAT-α-Galp-(I→4)-α-D-GalpA(2/3OAc)-(I→3)-α-D-GalpA-(I→ |
| Type 2 | →4-β-D-Glcp-(I→3)-[α-D-GlcpA-(I→6)-α-D-Glcp-(I→2)]-α-L-Rhap-(I→3)-α-L-Rhap-(I→3)-β-L-Rhap-(I→ |
| Type 3 | →3)-β-D-GlcA-(I→4)-β-D-Glcp-(I→ |
| Type 4 | →3β-D-ManpNAc-(I→3)-α-L-FucpNAc-(I→3)-α-D-GalpNAc-(I→4)-α- |

The polysaccharides may be used in the form of oligosaccharides. These are conveniently formed by fragmentation of purified polysaccharide (e.g. by hydrolysis), which will usually be followed by purification of the fragments of the desired size.

Polysaccharides may be purified from natural sources. As an alternative to purification, polysaccharides may be obtained by total or partial synthesis.

*N. meningitidis* Capsular Polysaccharides

The polysaccharide may be a bacterial capsular polysaccharide. Exemplary bacterial capsular polysaccharides include those from *N. meningitidis*. Based on the organism's capsular polysaccharide, various serogroups of *N. meningitidis* have been identified, including A, B, C, H, I, K, L, 29E, W135, X, Y, and Z. The polysaccharide may be from any of these serogroups. Typically, the polysaccharide is from one of the following meningococcal serogroups: A, C, W135 and Y.

The capsular polysaccharides will generally be used in the form of oligosaccharides. These are conveniently formed by fragmentation of purified capsular polysaccharide (e.g. by hydrolysis), which will usually be followed by purification of the fragments of the desired size. Fragmentation of polysaccharides is typically performed to give a final average degree of polymerization (DP) in the oligosaccharide of less than 30 (e.g. between 10 and 20, for example around 10 for serogroup A; between 15 and 25 for serogroups W135 and Y, for example between 15 and 20; between 12 and 22 for serogroup C; etc.). DP can conveniently be measured by ion exchange chromatography or by colorimetric assays (Ravenscroft et al. Vaccine 17, 2802-2816 (1999)).

If hydrolysis is performed, the hydrolysate will generally be sized in order to remove short-length oligosaccharides (Costantino et al. Vaccine 17, 1251-1263 (1999)). This can be achieved in various ways, such as ultrafiltration followed by ion-exchange chromatography. Oligosaccharides with a degree of polymerization of less than or equal to about 6 can be removed for serogroup A, and those less than around 4 can be removed for serogroups W135 and Y.

Chemical hydrolysis of saccharides generally involves treatment with either acid or base under conditions that are standard in the art. Conditions for depolymerization of capsular polysaccharides to their constituent monosaccharides are known in the art. One depolymerization method involves the use of hydrogen peroxide (see WO02/058737 which is incorporated herein by reference).

Hydrogen peroxide is added to a saccharide (e.g. to give a final $H_2O_2$ concentration of 1%), and the mixture is then incubated (e.g. at around 55° C.) until a desired chain length reduction has been achieved. The reduction over time can be followed by removing samples from the mixture and then measuring the (average) molecular size of saccharide in the sample. Depolymerization can then be stopped by rapid cooling once a desired chain length has been reached Serogroups C, W135 and Y Techniques for preparing capsular polysaccharides from meningococci have been known for many years, and typically involve a process comprising the steps of polysaccharide precipitation (e.g. using a cationic detergent), ethanol fractionation, cold phenol extraction (to remove protein) and ultracentrifugation (to remove LPS) (for example, see Frash, Advances in Biotechnological Processes 13, 123-145 (1990) (eds. Mizrahi & Van Wezel).

One such process involves polysaccharide precipitation followed by solubilization of the precipitated polysaccharide using a lower alcohol (see WO03/007985 which is incorporated herein by reference).

Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred (Inzana, Infect. Immun. 55, 1573-1579 (1987). Solubilization of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilizing CTAB-polysaccharide complexes. Ethanol may be added to the precipitated polysaccharide to give a final ethanol concentration (based on total content of ethanol and water) of between 50% and 95%.

After re-solubilization, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration. Once filtered to remove contaminants, the polysaccharide may be precipitated for further treatment and/or processing. This can be conveniently achieved by exchanging cations (e.g. by the addition of calcium or sodium salts).

As an alternative to purification, capsular polysaccharides of the present invention may be obtained by total or partial synthesis e.g. Hib synthesis is disclosed in Kandil et al. Glvcoconi J 14, 13-17. (1997), and MenA synthesis in Berkin et al. Chemistry 8, 4424-4433 (2002).

The polysaccharide may be chemically modified, that is it may be O-acetylated or de-O-acetylated. Any such de-O-acetylation or hyper-acetylation may be at specific positions in the polysaccharide. For instance, most serogroup C strains have O-acetyl groups at position C-7 and/or C-8 of the sialic acid residues, but about 15% of clinical isolates lack these O-acetyl groups (Glode et al. J Infect Pis 139, 52-56 (1979); see also WO94/05325 and U.S. Pat. No. 5,425,946 that are incorporated herein by reference). The acetylation does not seem to affect protective efficacy (e.g. unlike the Menjugate™ product, the NeisVac-C™ product uses a de-O-acetylated polysaccharide, but both vaccines are effective). The serogroup W135 polysaccharide is a polymer of sialic acid-galactose disaccharide units. The serogroup Y polysaccharide is similar to the serogroup W135 polysaccharide, except that the disaccharide repeating unit includes glucose instead of galactose. Like the serogroup C polysaccharides, the MenW135 and MenY polysaccharides have variable 0-acetylation, but at sialic acid 7 and 9 positions (see WO2005/033148 which is incorporated herein by reference). Any such chemical modifications preferably take place before conjugation, but may alternatively or additionally take place during conjugation.

Polysaccharides from different serogroups can be purified separately, and may then be combined either before or after conjugation.

Serogroup A

The polysaccharide may be from a serogroup A. The polysaccharide can be purified in the same way as for serogroups C, W135 and Y (see above), although it is structurally different, whereas the capsules of serogroups C, W135 and Y are based around sialic acid (N-acetyl-neuraminic acid, NeuAc), the capsule of serogroup A is based on N-acetyl-mannosamine, which is the natural precursor of sialic acid. The serogroup A polysaccharide is particularly susceptible to hydrolysis, and its instability in aqueous media means that (a) the immunogenicity of liquid vaccines against serogroup A declines over time, and (b) quality control is more difficult, due to release of saccharide hydrolysis products into the vaccine.

Native MenA capsular polysaccharide is a homopolymer of (a1→6)-linked N-acetyl-D-mannosamine-1-phosphate, with partial O-acetylation at C3 and C4. The principal glycosidic bond is a 1-6 phosphodiester bond involving the hemi-acetal group of C1 and the alcohol group of C6 of the D-mannosamine. The average chain length is 93 monomers. It has the following formula:

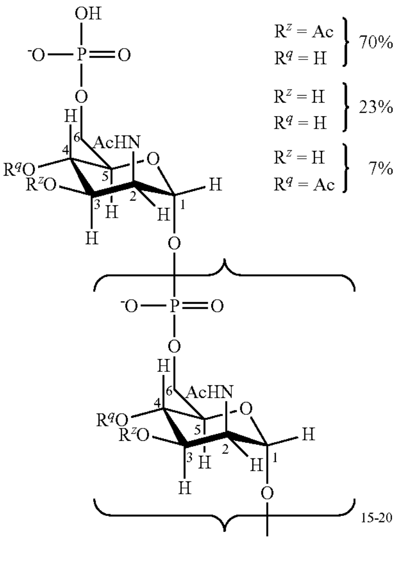

15-20

-continued

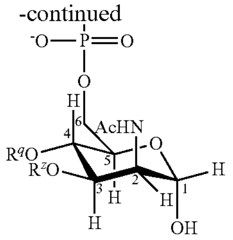

A modified polysaccharide has been prepared which retains the immunogenic activity of the native serogroup A polysaccharide but which is much more stable in water. Hydroxyl groups attached at carbons 3 and 4 of the monosaccharide units are replaced by a blocking group (see WO03/080678 & WO2008/084411).

The number of monosaccharide units having blocking groups in place of hydroxyls can vary. For example, all or substantially all the monosaccharide units may have blocking groups. Alternatively, at least 10%, 20%, 30%, 40%, 50%, 60%, 70%, 80% or 90% of the monosaccharide units may have blocking groups. At least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 monosaccharide units may have blocking groups.

Likewise, the number of blocking groups on a monosaccharide unit may vary. For example, the number of blocking groups on any particular monosaccharide unit may be 1 or 2.

The terminal monosaccharide unit may or may not have a blocking group instead of its native hydroxyl. It is preferred to retain a free anomeric hydroxyl group on a terminal monosaccharide unit in order to provide a handle for further reactions (e.g. conjugation). Anomeric hydroxyl groups can be converted to amino groups (—$NH_2$ or —NH-E, where E is a nitrogen protecting group) by reductive amination (using, for example, $NaBH_3CN/NH_4Cl$), and can then be regenerated after other hydroxyl groups have been converted to blocking groups.

Blocking groups to replace hydroxyl groups may be directly accessible via a derivatizing reaction of the hydroxyl group i.e. by replacing the hydrogen atom of the hydroxyl group with another group. Suitable derivatives of hydroxyl groups which act as blocking groups are, for example, carbamates, sulfonates, carbonates, esters, ethers (e.g. silyl ethers or alkyl ethers) and acetals. Some specific examples of such blocking groups are allyl, Aloc, benzyl, BOM, t-butyl, trityl, TBS, TBDPS, TES, TMS, TIPS, PMB, MEM, MOM, MTM, THP, etc. Other blocking groups that are not directly accessible and which completely replace the hydroxyl group include $C_{1-12}$ alkyl, $C_{3-12}$ alkyl, $C_{5-12}$ aryl, $C_{5-12}$ aryl $C_{1-6}$ alkyl, $NR^{21}R^{22}$ ($R^{21}$ and $R^{22}$ are defined in the following paragraph), H, F, C, Br, $CO_2H$, $CO_2(C_{1-6}$ alkyl), CN, $CF_3$, $CCl_3$, etc.

Typical blocking groups are of the formula: —O—X'—Y' and —$OR^{23}$ wherein: X' is C(O), S(O) or $SO_2$; Y is $C_{1-12}$ alkyl, $C_{1-12}$ alkoxy, $C_{3-12}$ cycloalkyl, $C_{5-12}$ aryl or $C_{5-12}$ aryl-$C_{1-6}$ alkyl, each of which may optionally be substituted with 1, 2 or 3 groups independently selected from F, C, Br, $CO_2H$, $CO_2(C_{1-6}$ alkyl), CN, $CF_3$ or $CCl_3$; or Y' is $NR^{21}R^{22}$; $R^{21}$ and $R^{22}$ are independently selected from H, $C_{1-12}$ alkyl, $C_{3-12}$ cycloalkyl, $C_{5-12}$ aryl, $C_{5-12}$ aryl-$C_{1-6}$ alkyl; or $R^{21}$ and $R^{22}$ may be joined to form a $C_{3-12}$ saturated heterocyclic group; $R^{23}$ is $C_{1-12}$ alkyl or $C_{3-12}$ cycloalkyl, each of which may optionally be substituted with 1, 2 or 3 groups independently selected from F, Cl, Br, $CO_2(C_{1-6}$ alkyl), CN, $CF_3$ or $CCl_3$; or $R^{23}$ is $C_{5-12}$ aryl or $C_{5-12}$ aryl-$C_{1-6}$ alkyl, each of which may optionally be substituted with 1, 2, 3, 4 or 5 groups selected from F, Cl, Br, $CO_2H$, $CO_2(C_{1-6}$ alkyl), CN, $CF_3$ or $CCl_3$. When $R^{23}$ is $C_{1-12}$ alkyl or $C_{3-12}$ cycloalkyl, it is typically substituted with 1, 2, or 3 groups as defined above. When $R^{21}$ and $R^{22}$ are joined to form a $C_{3-12}$ saturated heterocyclic group, it is meant that $R^{21}$ and $R^{22}$ together with the nitrogen atom form a saturated heterocyclic group containing any number of carbon atoms between 3 and 12 (e.g. $C_3$, $C_4$, $C_5$, $C_6$, $C_7$, $C_8$, $C_9$, $C_{10}$, $C_{11}$, $C_{12}$). The heterocyclic group may contain 1 or 2 heteroatoms (such as N, O, or S) other than the nitrogen atom. Examples of $C_{3-12}$ saturated heterocyclic groups are pyrrolidinyl, piperidinyl, morpholinyl, piperazinyl, imidazolidinyl, azetidinyl and aziridinyl.

Blocking groups —O—X—Y and —$OR^{23}$ can be prepared from —OH groups by standard derivatizing procedures, such as reaction of the hydroxyl group with an acyl halide, alkyl halide, sulfonyl halide, etc. Hence, the oxygen atom in —O—X'—Y' is usually the oxygen atom of the hydroxyl group, while the —X'—Y' group in —O—X'—Y' usually replaces the hydrogen atom of the hydroxyl group.

Alternatively, the blocking groups may be accessible via a substitution reaction, such as a Mitsonobu-type substitution. These and other methods of preparing blocking groups from hydroxyl groups are well known.

Specific blocking groups for use in the invention are —OC(O)$CF_3$ (Nilsson & Svensson Carbohydrate Research 69, 292-296 (1979)) and a carbamate group $OC(O)NR^{21}R^{22}$, where $R^{21}$ and $R^{22}$ are independently selected from $C_{1-6}$ alkyl. Typically, $R^{21}$ and $R^{22}$ are both methyl i.e. the blocking group is —$OC(O)NMe_2$. Carbamate blocking groups have a stabilizing effect on the glycosidic bond and may be prepared under mild conditions.

A particularly preferred blocking group is —$OC(O)CH_3$ (see WO2008/084411). The proportion of 4- and/or 3-positions in the modified *Neisseria meningitidis* serogroup A polysaccharide that have this blocking group may vary. For example, the proportion of 4-positions that have blocking groups may be about 0%, at least 10%, 20%, 30%, 40%, 50%, 60%, 70%, 80%, 90%, 95% or about 100%, with at least 80% and about 100% being preferred. Similarly, the proportion of 3-positions that have blocking groups may be about 0%, at least 10%, 20%, 30%, 40%, 50%, 60%, 70%, 80%, 90%, 95% or about 100%, with at least 80% and about 100% being preferred. Typically, the proportion of 4- and 3-positions that have blocking groups is about the same at each position. In other words, the ratio of 4-positions that have blocking groups to 3-positions that have blocking groups is about 1:1. However, in some embodiments, the proportion of 4-positions that have blocking groups may vary relative to the proportion of 3-positions that have blocking groups. For example, the ratio of 4-positions that have blocking groups to 3-positions that have blocking groups may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2. Similarly, the ratio of 3-positions that have blocking groups to 4-positions that have blocking groups may be 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2.

Typical modified MenA polysaccharides contain n monosaccharide units, where at least h % of the monosaccharide units do not have —OH groups at both of positions 3 and 4. The value of h is 24 or more (e.g. 25, 26, 27, 28, 29, 30, 35, 40, 45, 50, 55, 60, 65, 70, 75, 80, 85, 90, 95, 98, 99 or 100) and is usually 50 or more. The absent —OH groups are blocking groups as defined above.

Other typical modified MenA polysaccharides comprise monosaccharide units, wherein at least s of the monosaccharide units do not have —OH at the 3 position and do not have —OH at the 4 position. The value of s is at least 1 (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90). The absent —OH groups are blocking groups as defined above.

Suitable modified MenA polysaccharides have the formula:

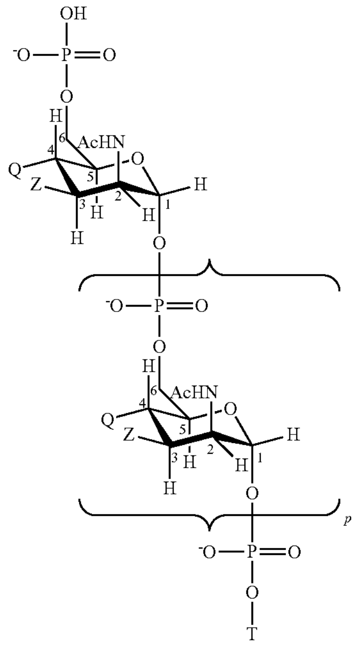

wherein p is an integer from 1 to 100 (particularly an integer from 5 to 25, usually 15-25); T is of the formula (A) or (B):

(A)

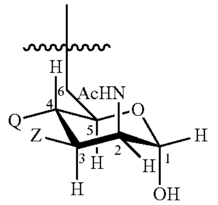

(B)

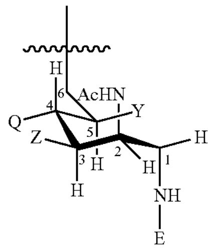

each Z group is independently selected from OH or a blocking group as defined above; and each Q group is independently selected from OH or a blocking group as defined above;

Y is selected from OH or a blocking group as defined above;

E is H or a nitrogen protecting group; and wherein more than about 7% (e.g. 8%, 9%, 10% or more) of the Q groups are blocking groups. In some embodiments, the hydroxyl group attached at carbon 1 in formula (A) is replaced by a blocking group as defined above. In some embodiments, E in formula (B) is a linker or a carrier molecule as discussed below. When E is a linker, the linker may be covalently bonded to a carrier molecule.

Each of the p+2 Z groups may be the same or different from each other. Likewise, each of the n+2 Q groups may be the same or different from each other. All the Z groups may be OH. Alternatively, at least 10%, 20, 30%, 40%, 50% or 60% of the Z groups may be OAc. Typically, about 70% of the Z groups are OAc, with the remainder of the Z groups being OH or blocking groups as defined above. At least about 7% of Q groups are blocking groups. Typically, at least 10%, 20%, 30%, 40%, 50%, 60%, 70%, 80%, 90% or even 100% of the Q groups are blocking groups.

Glucans

The polysaccharide may be a glucan. Glucans are glucose-containing polysaccharides found inter alia in fungal cell walls. The oglucans include one or more a-linkages between glucose subunits, whereas β-glucans include one or more β-linkages between glucose subunits. The glucan used in accordance with the invention includes β linkages, and may contain only β linkages (i.e. no a linkages).

The glucan may comprise one or more β-1,3-linkages and/or one or more β-1,6-linkages. It may also comprise one or more β-1,2-linkages and/or (β-1,4-linkages, but normally its only β linkages will be β-1,3-linkages and/or β-1 6-linkages. The glucan may be branched or linear. Full-length native β-glucans are insoluble and have a weight average molecular weight in the megadalton range. Thus, it is better to use soluble glucans in conjugates. Solubilization may be achieved by fragmenting long insoluble glucans. This may be achieved by hydrolysis or, more conveniently, by digestion with a glucanase (e.g. with a β-1,3-glucanase or a (β-1,6-glucanase). As an alternative, short glucans can be prepared synthetically by joining monosaccharide building blocks.

Low molecular weight glucans are preferred, particularly those with a weight average molecular weight of less than 100 kDa (e.g. less than 80, 70, 60, 50, 40, 30, 25, 20, or 15 kDa). It is also possible to use oligosaccharides e.g. containing 60 or fewer (e.g. 59, 58, 57, 56, 55, 54, 53, 52, 51, 50, 49, 48, 47, 46, 45, 44, 43, 42, 41, 4039, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4) glucose monosaccharide units. Within this range, oligosaccharides with between 10 and 50 or between 20 and 40 monosaccharide units. The glucan may be a fungal glucan. A fungal glucan will generally be obtained from a fungus but, where a particular glucan structure is found in both fungi and non-fungi (e.g. in bacteria, lower plants or algae) then the non-fungal organism may be used as an alternative source. Thus the glucan may be derived from the cell wall of a *Candida*, such as *C. albicans*, or from *Coccidioides immitis, Trichophyton verrucosum, Blastomyces dermatidis, Cryptococcus neoformans, Histoplasma capsulatum, Saccharomyces cerevisiae, Paracoccidioides brasiliensis*, or *Pythiumn insidiosum.*

There are various sources of fungal β-glucans. For instance, pure β-glucans are commercially available e.g. pustulan (Calbiochem) is a β-1,6-glucan purified from *Umbilicaria papullosa*. β-glucans can be purified from fungal cell walls in various ways. Tokunaka et al. Carbohydrate Research 316, 161-172. (1999), for instance, discloses a two-step procedure for preparing a water-soluble β-glucan extract from *Candida*, free from cell-wall mannan, involving NaClO oxidation and DMSO extraction. The resulting product ('*Candida* soluble β-D-glucan' or 'CSBG') is mainly composed of a linear β-1,3-glucan with a linear β-1,6-glucan moiety. Similarly, WO03/097091 discloses the production of GG-zym from Calbicans. Such glucans from *C. albicans*, include (a) β-1,6-glucans with β-1,3-glucan lateral chains and an average degree of polymerization of about 30, and (b) β-1,3-glucans with (β-1,6-glucan lateral chains and an average degree of polymerization of about 4.

In some embodiments, the glucan is a β-1,3 glucan with some β-1,6 branching, as seen in e.g. laminarins. Laminarins are found in brown algae and seaweeds. The β(1-3):β(1-6) ratios of laminarins vary between different sources e.g. it is as low as 3:2 in *Eisenia bicyclis laminarin*, but as high as 7:1 in *Laminaria digititata laminarin* (Pang et al. Biosci Biotechnol Biochem 69, 553-8 (2005)). Thus the glucan may have a β(1-3):β(1-6) ratio of between 1.5:1 and 7.5:1 e.g. about 2:1, 3:1, 4:1, 5:1, 6:1 or 7:1. Optionally, the glucan may have a terminal mannitol subunit, e.g. a 1,1-O-linked mannitol residue (Read et al. Carbohydr Res. 281, 187-201 (1996). The glucan may also comprise mannose subunits.

In other embodiments, the glucan has exclusively or mainly β-1,3 linkages, as seen in curdlan. These glucans may elicit better protection than glucans comprising other linkages, particularly glucans comprising β-1,3 linkages and a greater proportion of β-1,6 linkages. Thus the glucan may be made solely of β-1,3-linked glucose residues (e.g. linear β-D-glucopyranoses with exclusively 1,3 linkages). Optionally, though, the glucan may include monosaccharide residues that are not β-1,3-linked glucose residues e.g. it may include β-1,6-linked glucose residues. The ratio of β-1,3-linked glucose residues to these other residues should be at least 8:1 (e.g. >9:1, >10:1, >11:1, >12:1, >13:1, >14:1, >15:1, >16:1, >17:1, >18:1, >19:1, >20:1, >25:1, >30:1, >35:1, >40:1, >45:1, >50:1, >75:1, >100:1, etc.) and/or there are one or more (e.g. >1, >2, >3, >4, >5, >6, >7, >8, >9, >10, >11, >12, etc.) sequences of at least five (e.g. >5, >6, >7, >8, >9, >10, >11, >12, >13, >14, >15, >16, >17, >18, >19, >20, >30, >40, >50, >60, etc.) adjacent non-terminal residues linked to other residues only by β-1,3 linkages. By "non-terminal" it is meant that the residue is not present at a free end of the glucan. In some embodiments, the adjacent non-terminal residues may not include any residues coupled to a carrier molecule or linker. The presence of five adjacent non-terminal residues linked to other residues only by β-1,3 linkages may provide a protective antibody response, e.g. against *C. albicans*.

In further embodiments, a conjugate may include two different glucans e.g. a first glucan having a β(1-3):β(1-6) ratio of between 1.5:1 and 7.5:1, and a second glucan having exclusively or mainly β-1,3 linkages. For instance a conjugate may include both a laminarin glucan and a curdlan glucan. Where a β-glucan includes both β-1,3 and β-1,6 linkages at a desired ratio and/or sequence then this glucan may be found in nature (e.g. a laminarin), or it may be made artificially. For instance, it may be made by chemical synthesis, in whole or in part.

Methods for the chemical synthesis of β-1,3/3-1,6 glucans are known, for example from Takeo and Tei Carbohvdr Res. 145, 293-306 (1986), Tanaka et al. Tetrahedron Letters 44, 3053-3057 (2003), Ning et al. Tetrahedron Letters 43, 5545-5549 (2002), Geurtsen et al. Journal of Organic Chemistry 64 (21):7828-7835 (1999), Wu et al. Carbohvdr Res. 338, 2203-12 (2003), Nicolaou et al. J. Am. Chem. Soc. 119, 449-450 (1997), Yamada et al. Tetrahedron Letters 40, 4581-4584 (1999), Yamago et al. Org. Lett. 24, 3867-3870 (2001), Yuguo et al. Tetrahedron 60, 6345-6351 (2004), Amaya et al. Tetrahedron Letters 42:9191-9194 (2001), Mei et al. Carbohvdr Res. 340. 2345-2351 (2005).

β-glucan including both β-1,3 and β-1,6 linkages at a desired ratio may also be made starting from an available glucan and treating it with a β-1,6-glucanase (also known as glucan endo-1,6-β-glucosidase, 1,6-β-D-glucan glucanohydrolase, etc.; EC 3.2.1.75) or a β-1,3-glucanase (such as an exo-1,3-glucanase (EC 3.2.1.58) or an endo-1,3-glucanase (EC 3.2.1.39) until a desired ratio and/or sequence is reached.

When a glucan containing solely β-1,3-linked glucose is desired then 3-1,6-glucanase treatment may be pursued to completion, as β-1,6-glucanase will eventually yield pure β-1,3 glucan. More conveniently, however, a pure β-1,3-glucan may be used. These may be made synthetically, by chemical and/or enzymatic synthesis e.g. using a (1→3)-β-D-glucan synthase, of which several are known from many organisms (including bacteria, yeasts, plants and fungi). Methods for the chemical synthesis of β-1,3 glucans are known, for example from Takeo et al. Carbohydr Res. 245, 81-96 (1993), Jamois et al. Glycobiology 15(4), 393-407 (2005), Lefeber et al. C em. Eur. J. 7(20):441 1-4421 (2001) and Huang et al. Carbohydr Res. 340, 603-608 (2005). As a useful alternative to synthesis, a natural β-1,3-glucan may be used, such as a curdlan (linear (β-1,3-glucan from an *Agrobacterium* previously known as *Alcaligenes faecalis* var. myxogenes; commercially available e.g. from Sigma-Aldrich catalog C7821) or paramylon (β-1,3-glucan from *Euglena*). Organisms producing high levels of β-1,3-glucans are known in the art e.g. the *Agrobacterium* of U.S. Pat. No. 5,508,191 or MiKyoung et al. Biochemical Engineering Journal. 16, 163-8 (2003), or the *Euglena gracilis* of Barsanti et al. J App. Phycology, 13, 59-65 (2001).

Laminarin and curdlan are typically found in nature as high molecular weight polymers e.g. with a weight average molecular weight of at least 100 kDa. They are often insoluble in aqueous media. In their natural forms, therefore, they are not well suited to immunization. Thus, in some embodiments, a shorter glucan e.g. those containing 60 or fewer glucose monosaccharide units (e.g. 59, 58, 57, 56, 55, 54, 53, 52, 51, 50, 49, 48, 47, 46, 45, 44, 43, 42, 41, 40 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4). A glucan having a number of glucose residues in the range of 2-60 may be used e.g. between about 10-50 or between about 20-40 glucose units. A glucan with 25-30 glucose residues is particularly useful. Suitable glucans may be formed e.g. by acid hydrolysis of a natural glucan, or by enzymatic digestion e.g. with a glucanase, such as a β-1,3-glucanase. A glucan with 11-19, e.g. 13-19 and particularly 15 or 17, glucose monosaccharide units is also useful. In particular, glucans with the following structures (A) or (B) are specifically envisaged for use: (A)

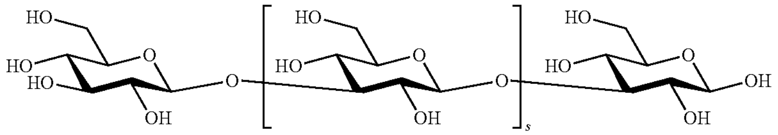

wherein s+2 is in the range of 2-60, e.g. between 10-50 or between 2-40.

In some embodiments, s+2 is in the range of 25-30 or 1 1-19, e.g. 13-17. In particular, s+2=15 is suitable. In addition, s+2=6 is suitable.

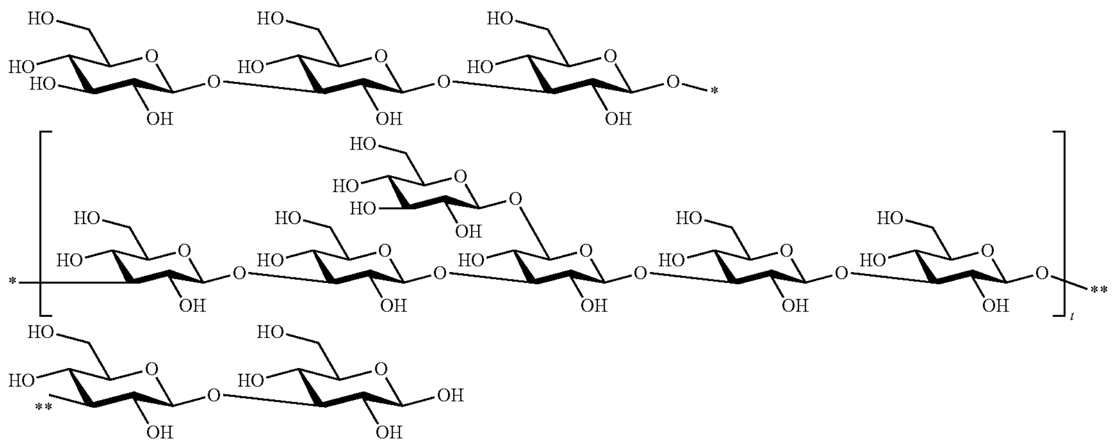

wherein t is in the range of 0-9, e.g. between 1-7 or between 2-6. Preferably, t is in the range of 3-4 or 1-3. In particular, t=2 is suitable. The * and ** indicate the respective attachment points of the polysaccharide units.

In some embodiments, the glucan contains between 5 to 7 glucose monosaccharide units (i.e. 5, 6 or 7). In particular, a glucan having 6 glucose monosaccharide units may be preferred. For example, the glucan may be a curdlan having 6 glucose monosaccharide units.

In some embodiments, the glucan is a single molecular species. In these embodiments, all of the glucan molecules are identical in terms of sequence.

Accordingly, all of the glucan molecules are identical in terms of their structural properties, including molecular weight etc. Typically, this form of glucan is obtained by chemical synthesis, e.g. using the methods described above. Alternatively, in other embodiments, the glucan may be obtained from a natural glucan, e.g. a glucan from *L. digitata*, *Agrobacterium* or *Euglena* as described above, with the glucan being purified until the required single molecular species is obtained. Natural glucans that have been purified in this way are commercially available. A glucan that is a single molecular species may be identified by measuring the polydispersity (Mw/Mn) of the glucan sample. This parameter can conveniently be measured by SEC-MALLS, for example as described in Bardotti et al. Vaccine 26, 2284-96 (2008). Suitable glucans for use in this embodiment of the invention have a polydispersity of about 1, e.g. 1.01 or less.

Solubility of natural glucans, such as curdlan, can be increased by introducing ionic groups (e.g. by sulfation, particularly at 0-6 in curdlan). Such modifications may be used with the invention, but are ideally avoided as they may alter the glucan's antigenicity.

When the polysaccharide is a glucan, it is typically a laminarin.

*S. pneumoniae* Capsular Polysaccharides

As discussed above, the polysaccharide may also be a bacterial capsular polysaccharide. Further exemplary bacterial capsular polysaccharides include those from *S. pneumoniae*. When the polysaccharide is a capsular polysaccharide from *S. pneumoniae*, it is typically from one of the following pneumococcal serotypes: 1, 2, 3, 4, 5, 6A, 6B, 7F, 8, 9N, 9V, 10A, 11A, 12F, 14, 15B, 17F, 18C, 19A, 19F, 20, 22F, 23F, and 33F. In some embodiments, it is from 1, 5, 6B, 14, 19F, and 23F. Capsular polysaccharides from *S. pneumoniae* comprise repeating oligosaccharide units which may contain up to 8 sugar residues. The oligosaccharide units for the main *S. pneumoniae* serotypes are described in the table above, Jones An. Acad. Bras. Cienc, 77(2), 293-324 (2005) and Jones, J Pharm Biomed Anal 38, 840-850 (2005).

*S. agalactiae* Capsular Polysaccharides

Further exemplary bacterial capsular polysaccharides include those from *Streptococcus agalactiae* ("GBS"). The capsular polysaccharide is covalently linked to the peptidoglycan backbone of GBS, and is distinct from the group B antigen, which is another polysaccharide that is attached to the peptidoglycan backbone.

The GBS capsular polysaccharides are chemically related, but are antigenically very different. All GBS capsular polysaccharides share the following trisaccharide core: β-D-GlcpNAc(1→3)β-D-Galp(1→4)β-D-Glcp The various GBS serotypes differ by the way in which this core is modified. The difference between serotypes 1a and III, for instance, arises from the use of either the GlcNAc (1a) or the Gal (III) in this core for linking consecutive trisaccharide cores.

Serotypes 1a and 1b both have a [a-D-NeupNAc(2→3)β-D-Galp-(1→] disaccharide linked to the GlcNAc in the core, but the linkage is either 1→4 (1a) or 1→3 (1b).

GBS-related disease arises primarily from serotypes Ia, Ib, II, III, IV, V, VI, VII, and VIII, with over 85% being caused by five serotypes: Ia, Ib, III & V. A polysaccharide from one of these four serotypes may be used. The capsular polysaccharides of each of these four serotypes include: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core.

All four polysaccharides include galactose residues within the trisaccharide core, but serotypes Ia, Ib, II & III also contain additional galactose residues in each repeating unit.

Polysaccharides used may be in their native form, or may have been modified. For example, the polysaccharide may be shorter than the native capsular polysaccharide, or may be chemically modified. In particular, the serotype V capsular polysaccharide used in the invention may be modified as described in WO2006/050341 and Guttormsen et al. Proc Natl Acad Sci USA. 105(15), 5903-8 (2008) Epub 2008 Mar. 31. For example, a serotype V capsular polysaccharide that has been substantially desialylated. Desialylated GBS serotype V capsular polysaccharide may be prepared by treating purified GBS serotype V capsular polysaccharide under mildly acidic conditions (e.g. 0.1 M sulphuric acid at 80° C. for 60 minutes) or by treatment with neuraminidase. Thus the polysaccharide used according to the invention may be a substantially full-length capsular polysaccharide, as found in nature, or it may be shorter than the natural length. Full-length polysaccharides may be depolymerized to give shorter fragments for use with the invention e.g. by hydrolysis in mild acid, by heating, by sizing chromatography, etc. In particular, the serotype II and/or III capsular polysaccharides used in the invention may be depolymerized as described in WO96/40795 and Michon et al. Clin Vaccine Immunol. (2006) 13(8), 936-43.

The polysaccharide may be chemically modified relative to the capsular polysaccharide as found in nature. For example, the polysaccharide may be de-O-acetylated (partially or fully), de-N-acetylated (partially or fully), N-propionated (partially or fully), etc. De-acetylation may occur before, during or after conjugation, but preferably occurs before conjugation. Depending on the particular polysaccharide, deacetylation may or may not affect immunogenicity. The relevance of O-acetylation on GBS polysaccharides in various serotypes is discussed in Lewis et al. PNAS USA 101, 11123-8 (2004), and in some embodiments O-acetylation of sialic acid residues at positions 7, 8 and/or 9 is retained before, during and after conjugation e.g. by protection/deprotection, by re-acetylation, etc. However, typically the GBS polysaccharide used in the present invention has substantially no O-acetylation of sialic acid residues at positions 7, 8 and/or 9. In particular, when the GBS polysaccharide has been purified by base extraction as described below, then 0-acetylation is typically lost. The effect of de-acetylation etc. can be assessed by routine assays.

Capsular polysaccharides can be purified by known techniques, as described in Wessels et al. Infect Immun 57, 1089-94 (1989). A typical process involves base extraction, centrifugation, filtration, RNase/DNase treatment, protease treatment, concentration, size exclusion chromatography, ultrafiltration, anion exchange chromatography, and further ultrafiltration. Treatment of GBS cells with the enzyme mutanolysin, which cleaves the bacterial cell wall to free the cell wall components, is also useful.

As an alternative, the purification process described in WO2006/082527 can be used. This involves base extraction, ethanol/CaCl2 treatment, CTAB precipitation, and re-solubilisation. A further alternative process is described in WO2009/081276.

*S. aureus* Capsular Polysaccharides

Further exemplary bacterial capsular polysaccharides include those from *S. aureus*, particularly the capsular polysaccharides of *S. aureus* type 5 and type 8. The structures of type 5 and type 8 capsular polysaccharides were described in Moreau et al. Carbohydrate Res. 339(5), 285-91 (1990) and Fournier et al. Infect. Immun. 45(1), 87-93 (1984) as:

Type 5

→4)-β-D-ManNAcA(30Ac)-(1→4)-a-L-FucNAc(1→3)-β-D-FucNAc-(1

Type 8

→3)-β-D-ManNAcA(40Ac)-(1→3)-a-L-FucNAc(1→3)-β-D-FucNAc-(1 Recent NMR spectroscopy data (Jones Carbohydrate Res. 340(6), 1097-106 (2005)) has led to a revision of these structures to:

Type 5

→4)-β-D-ManNAcA-(1→4)-a-L-FucNAc(30Ac)-(1→3)-β-D-FucNAc-(1

Type 8

→3)-β-D-ManNAcA(40Ac)-(1→3)-a-L-FucNAc(1→3)-a-D-FucNAc(1→The polysaccharide may be chemically modified relative to the capsular polysaccharide as found in nature.

For example, the polysaccharide may be de-O-acetylated (partially or fully), de-N-acetylated (partially or fully), N-propionated (partially or fully), etc. De-acetylation may occur before, during or after conjugation, but typically occurs before conjugation. The effect of de-acetylation etc. can be assessed by routine assays. For example, the relevance of O-acetylation on *S. aureus* type 5 or type 8 capsular polysaccharides is discussed in Fattom et al. Infect Immun. 66(10): 4588-92 (1998). The native polysaccharides are said in this document to have 75% O-acetylation. These polysaccharides induced antibodies to both the polysaccharide backbone and O-acetyl groups. Polysaccharides with 0% O-acetylation still elicited antibodies to the polysaccharide backbone. Both types of antibody were opsonic against *S. aureus* strains that varied in their O-acetyl content. Accordingly, the type 5 or type 8 capsular polysaccharides used in the present invention may have between 0 and 100% 0-acetylation.

The degree of O-acetylation of the polysaccharide can be determined by any method known in the art, for example, by proton NMR (e.g. as described in Lemercinier and Jones Carbohydrate Res. 296, 83-96 (1996), Jones and Lemercinier, J Pharm BiomedAnal. 30(4), 1233-47 (2002), WO05/033148 or WO 00/56357. A further method is described in Hestrin J. Biol. Chem. 180, 249-261 (1949). Similar methods may be used to determine the degree of N-acetylation of the polysaccharide. O-acetyl groups may be removed by hydrolysis, for example by treatment with a base such as anhydrous hydrazine (Konadu et al. Infect. Immun. 62, 5048-5054 (1994)) or NaOH (Fattom et al. Infect Immun. 66(10):4588-92 (1998)). Similar methods may be used to remove N-acetyl groups. To maintain high levels of O-acetylation on type 5 and/or 8 capsular polysaccharides, treatments that lead to hydrolysis of the O-acetyl groups are minimized, e.g. treatments at extremes of pH.

Capsular polysaccharides can be purified by known techniques, as described in the references herein. A typical process involves phenol-ethanol inactivation of *S. aureus* cells, centrifugation, lysostaphin treatment, RNase/DNase treatment, centrifugation, dialysis, protease treatment, further dialysis, filtration, precipitation with ethanol/CaCl2, dialysis, freeze-drying, anion exchange chromatography, dialysis, freeze-drying, size exclusion chromatography, dialysis and freeze-drying (Fattom et al. Infect Immun. 58(7), 2367-74 (1990)). An alternative process involves autoclaving *S. aureus* cells, ultrafiltration of the polysaccharide-containing supernatant, concentration, lyophilisation, treatment with sodium metaperiodate to remove teichoic acid, further ultrafiltration, diafiltration, high performance size exclusion liquid chromatography, dialysis and freeze-drying (Gilbert et al. J. Microb. Meth. 20, 39-46 (1994)). The invention is not limited to polysaccharides purified from natural sources, however, and the polysaccharides may be obtained by other methods, such as total or partial synthesis.

Other Bacterial Capsular Polysaccharides

Further exemplary bacterial capsular polysaccharides include those from *Haemophilus influenzae* Type b, *Salmonella enterica Typhi Vi* and *Clostridium difficile.*

*S. agalactiae* carbohydrate: Non-capsular bacterial polysaccharides may also be used. An exemplary non-capsular bacterial polysaccharides is the *S. pyogenes* GAS carbohydrate (also known as the GAS cell wall polysaccharide, or GASP). This polysaccharide features a branched structure with an L-rhamnopyranose (Rhap) backbone consisting of alternating alpha-(1→2) and alpha-(1→3) links and D-N-acetylglucosamine (GlcpNAc) residues beta-(1→3)-connected to alternating rhamnose rings (Kreis et al. Int J Biol Macromol. 17(3-4), 117-30 (1995)).

The GAS carbohydrate will generally be in its native form, but it may have been modified. For example, the polysaccharide may be shorter than the native GAS carbohydrate, or may be chemically modified.

Thus the polysaccharide used according to the invention may be a substantially full-length GAS carbohydrate, as found in nature, or it may be shorter than the natural length. Full-length polysaccharides may be depolymerized to give shorter fragments for use with the invention e.g. by hydrolysis in mild acid, by heating, by sizing chromatography, etc. A short fragment thought to correspond to the terminal unit on the GAS carbohydrate has been proposed for use in a vaccine (Hoog et al., Carbohydr Res. 337(21-23), 2023-36 (2002)). Accordingly, short fragments are envisaged in the present invention. However, it is preferred to use polysaccharides of substantially full-length. The GAS carbohydrate typically has a weight average molecular weight of about 10 kDa, in particular about 7.5-8.5 kDa. Molecular masses can be measured by HPLC, for example SEC-HPLC using a TSK Gel G3000SW column (Sigma) relative to pullulan standards, such as those available from Polymer Standard Service (www.Polymer.de).

The polysaccharide may be chemically modified relative to the GAS carbohydrate as found in nature. For example, the polysaccharide may be de-N-acetylated (partially or fully), N-propionated (partially or fully), etc. The effect of de-acetylation etc., for example on immunogenicity, can be assessed by routine assays.

In some embodiments, the polysaccharide is GBSII antigenic polysaccharide having the structure shown below:

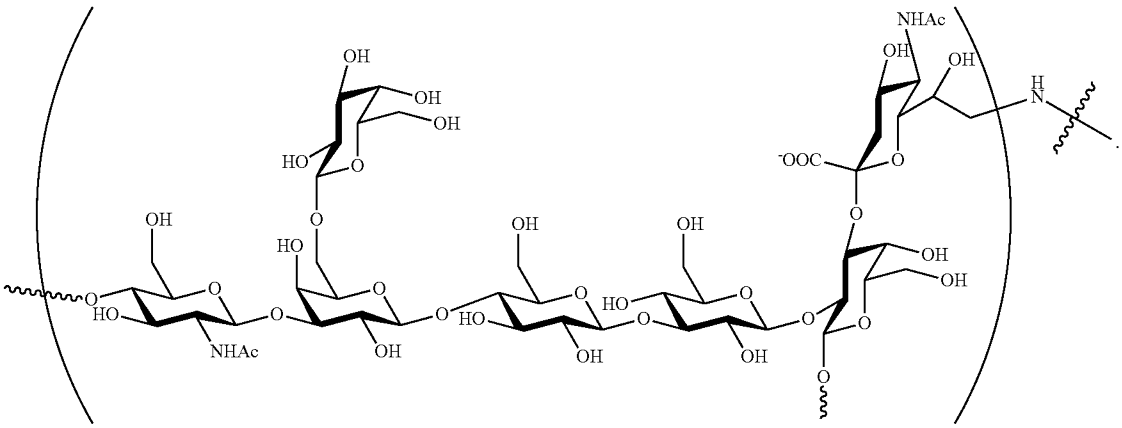

In some embodiments, the polysaccharide is GBSV antigenic polysaccharide having the structure shown below:

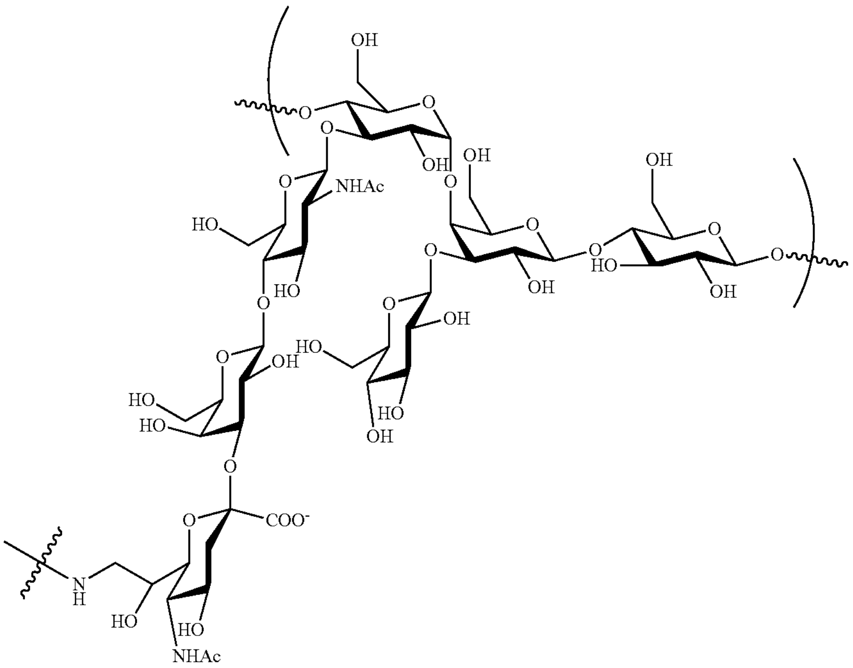

In some embodiments, the polysaccharide is MenA antigenic polysaccharide having the structure shown below:
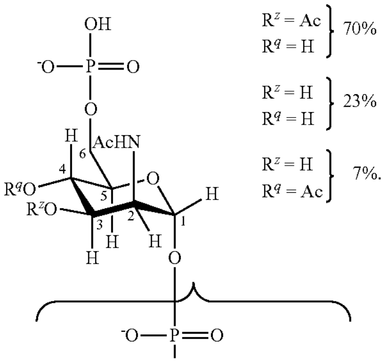
-continued
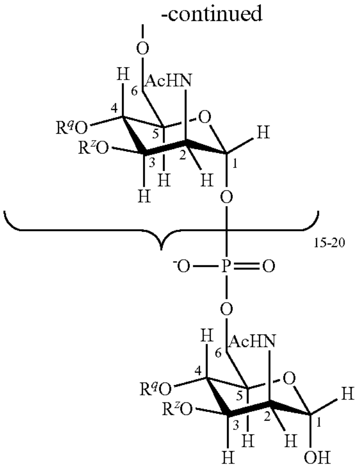
In another aspect, compounds of the formula (I) $R^1$-$(Leu)_x$-Gln-$(Gly)_y$-(A-W—B—$R^2$)$_z$ or (II) $R^1$-$(Leu)_x$-Gln-$(Gly)_y$-(NH—W—$R^2$)$_z$ are disclosed where x, y, z, $R^1$, $R^2$, A, B, and W are defined above. In some embodiments, the compounds are any one of:
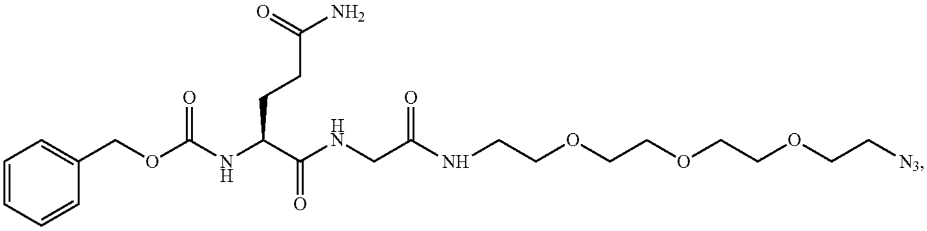
,
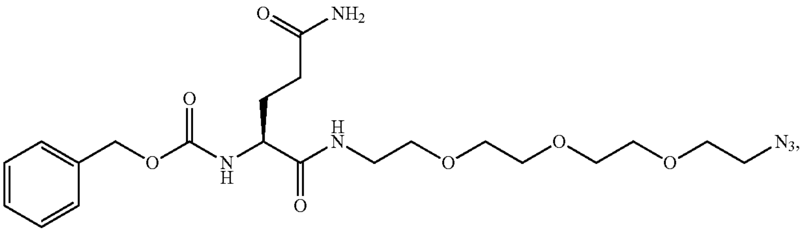
,
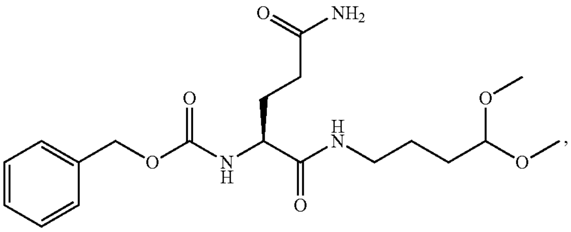
,
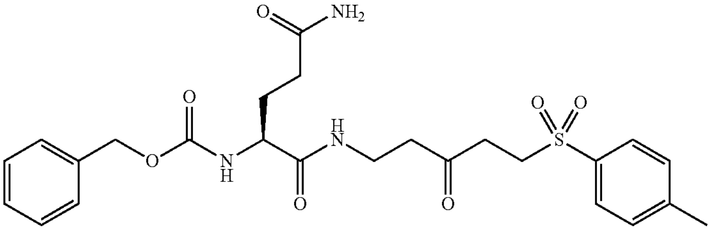
, -continued
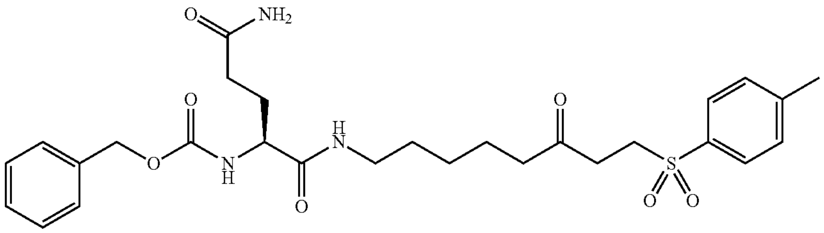
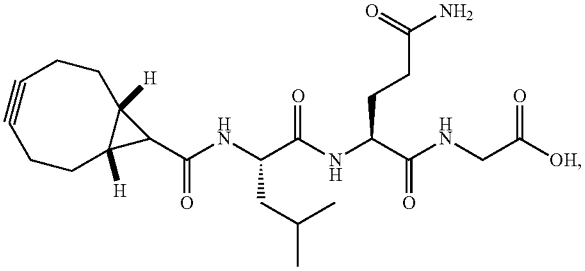
,
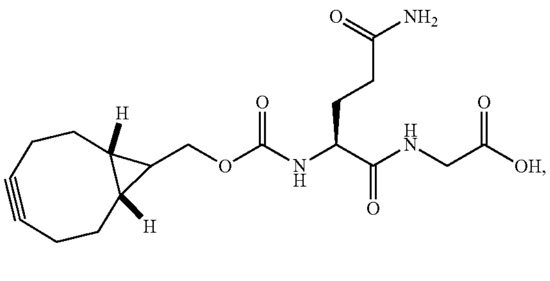
,
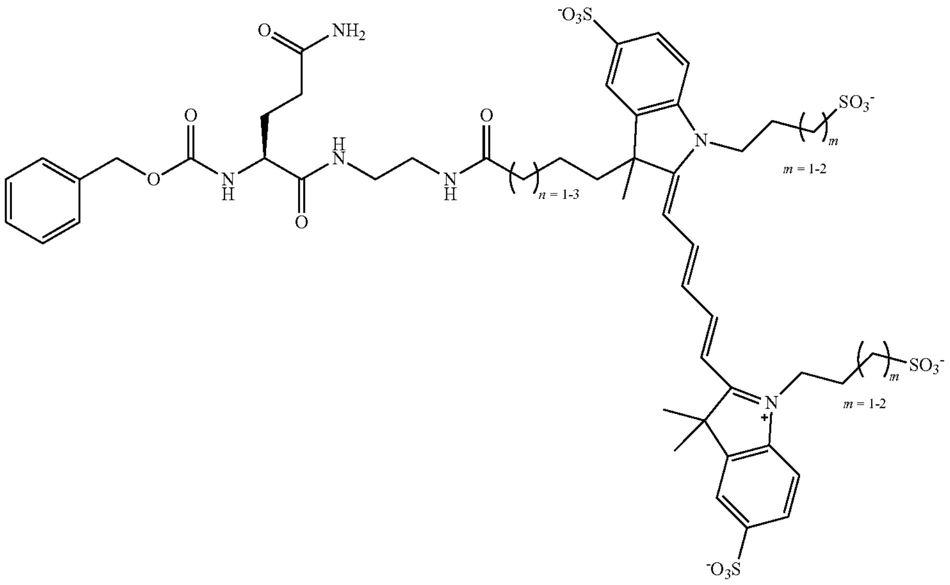
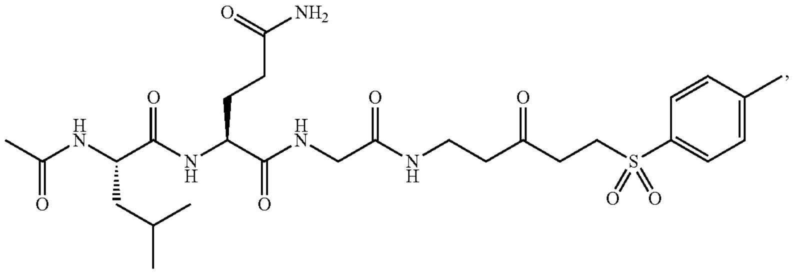
,
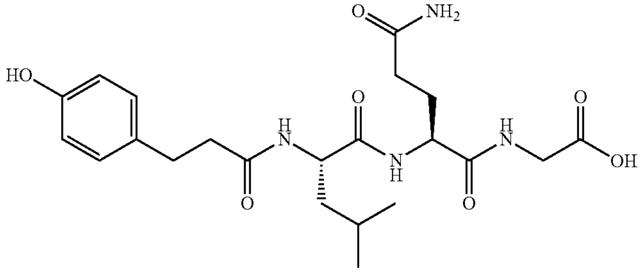

-continued
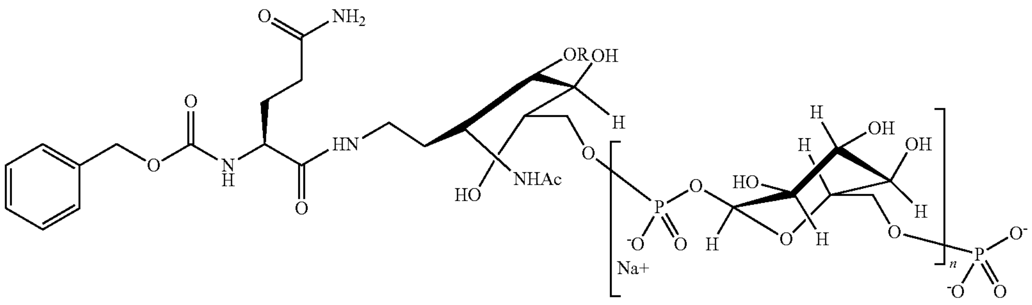
$n$ = 15-20
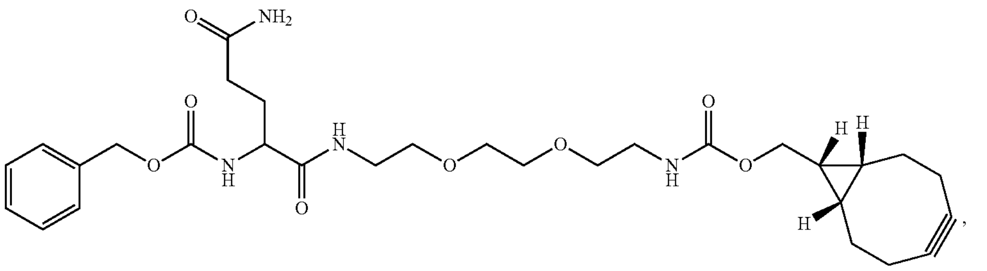
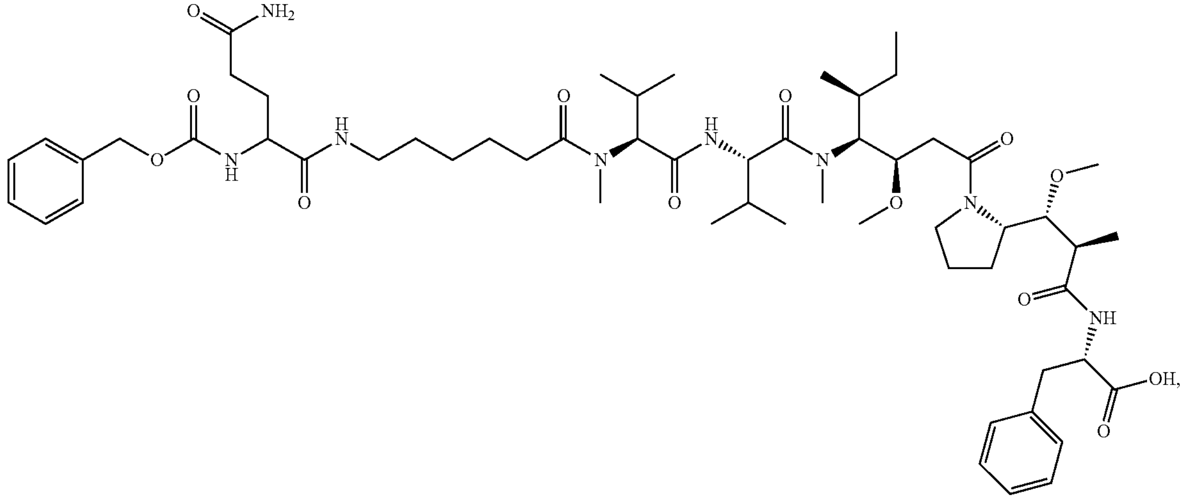
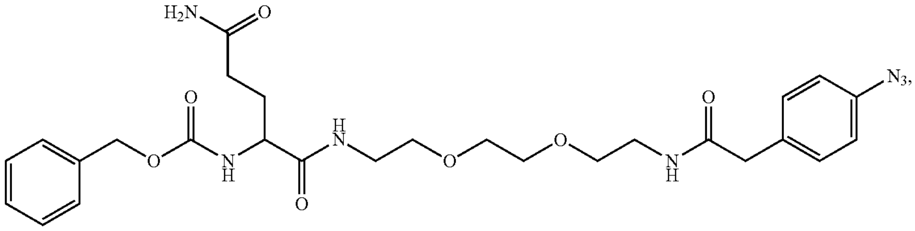
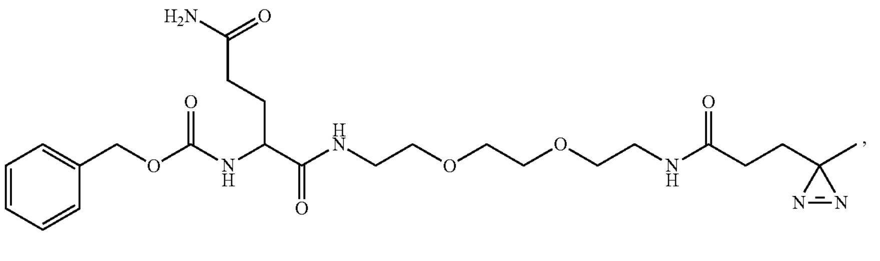

-continued

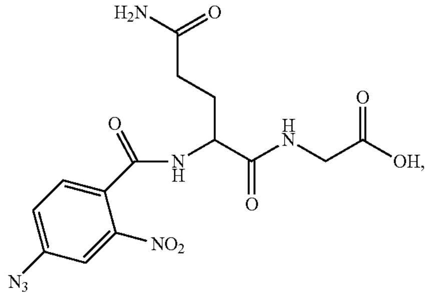

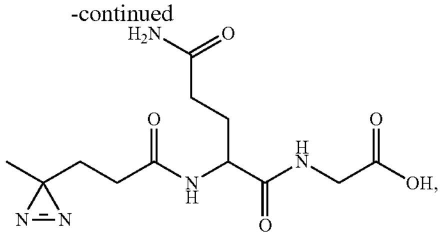

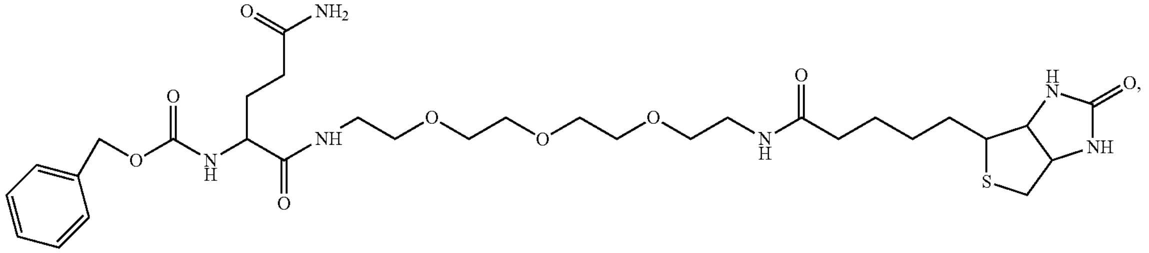

and

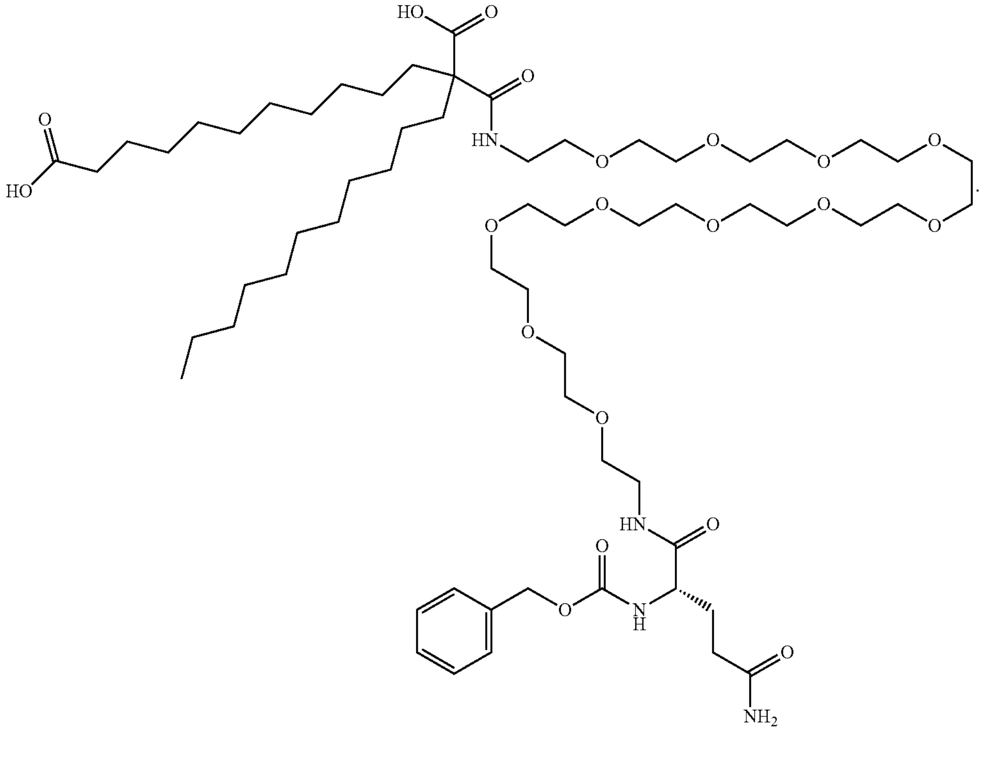

In embodiments having an eight-membered cycloalkyne group, that group can be attached to the modifying group by covalent linkage. Typically, the eight-membered cycloalkyne group is attached via a spacer and at a terminus of the spacer. The other terminus of the spacer has a functional group for attachment to the modifying group through the amino or carboxylic acid terminus of the peptide, but not at the ϵ-amino group of the glutamine. For example, if attachment will be at the amine portion of the modifying group, then spacer can include any functional group that allows attachment to an amine (e.g. a succinimidyl ester). Similarly, if the attachment will be at the carboxylic acid portion of the modifying group, then the spacer can include any functional group that allows attachment to a carboxylic acid (e.g. an amine).

In some embodiments, the eight-membered cycloalkyne group includes one or more nitrogen atoms, such as 1, 2 or 3 nitrogen atoms. In some embodiments, the eight-membered cycloalkyne group is fused to one or more other ring systems, such as cyclopropane or benzene. In one preferred embodiment, the eight-membered cycloalkyne group is fused to a cyclopropane group. In another preferred embodiment, the eight-membered cycloalkyne group is fused to two benzene groups. In most preferred embodiments, the eight-membered cycloalkyne group is a cyclooctyne group.

In one embodiment, the attachment is carried out using a compound having the formula $X^1$-L-$X^2$, where $X^1$ is the eight-membered cycloalkyne group and $X^2$-L is the spacer. In these embodiments, $X^2$ may be any group that can react with a functional group on the amine group on the peptide, and L is a linking moiety in the spacer.

In one embodiment, $X^2$ is N-oxysuccinimide. This group is suitable for attachment to an amine on a peptide. L may be a straight chain alkyl with 1 to 10 carbon atoms (e.g. $C_1$, $C_2$, $C_3$, $C_4$, $C_5$, $C_6$, $C_7$, $C_8$, $C_9$, $C_{10}$) e.g. $(CH_2)_4$ or $(CH_2)_3$. L typically has formula $-L^3-L^2-L^1$, in which $L^1$ is carbonyl, $L^2$ is a straight chain alkyl with 1 to 10 carbon atoms (e.g. $C_1$, $C_2$, $C_3$, $C_4$, $C_5$, $C_6$, $C_7$, $C_8$, $C_9$, $C_{10}$) e.g. $(CH_2)_4$ or $(CH_2)_5$ or $L^2$ is absent, and $L^3$ is —NHC(O)—, carbonyl or —O($CH_3$)—.

In one embodiment, $L^1$ is carbonyl, $L^2$ is $(CH_2)_5$ and $L^3$ is —NHC(O)—. In another embodiment, $L^1$ is carbonyl, $L^2$ is $(CH_2)_4$ and $L^3$ is carbonyl. In another embodiment, $L^1$ is carbonyl, $L^2$ is absent and $L^3$ is —O(CH3)-.

In one embodiment, $X^1$ is

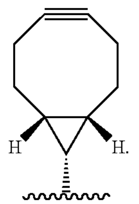

In another embodiment, $X^1$ is:

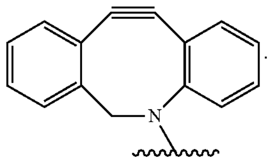 [SMILES: *N1Cc2ccccc2C#Cc2ccccc21]

In another embodiment, $X^1$ is

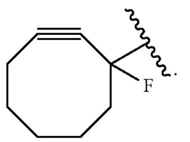

In one embodiment, a compound having the formula $X^1$-L-$X^2$ is

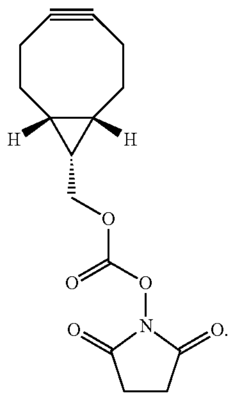 [SMILES: O=C(OC[C@@H]1[C@@H]2CCC#CCC[C@@H]21)ON1C(=O)CCC1=O]

In one embodiment, a compound having the formula $X^1$-L-$X^2$ is

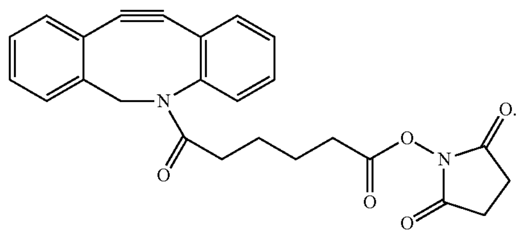 [SMILES: O=C(CCCCC(=O)N1Cc2ccccc2C#Cc2ccccc21)ON1C(=O)CCC1=O]

In one embodiment, a compound having the formula $X^1$-L-$X^2$ is:

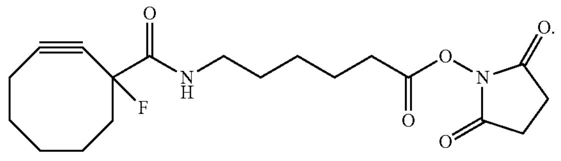 [SMILES: O=C(CCCCCNC(=O)C1(F)C#CCCCCC1)ON1C(=O)CCC1=O]

When the $R^2$ group includes a fluorophore, suitable fluorophore groups may be prepared according to techniques well known in the art. For example as shown in Scheme I, a general protocol is exemplified for preparing a fluorophore functionalized modifying group.

Scheme I.

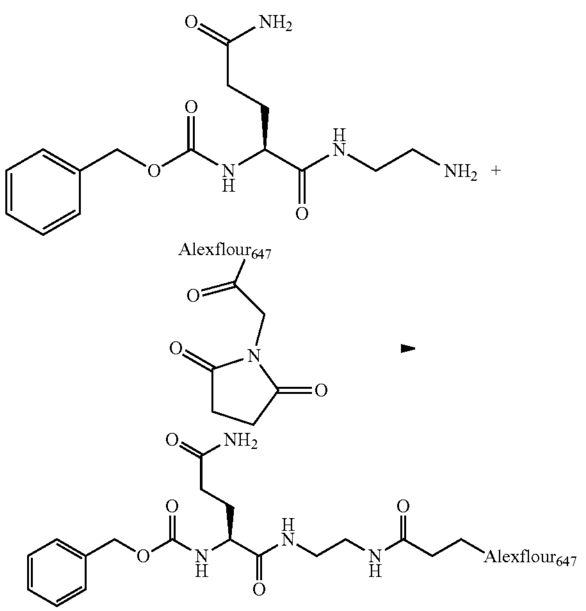

Target Proteins

A target compound can be one that is a substrate for microbial transglutaminase, for example proteins that are substrates for microbial transglutaminase. In one aspect, the target compound contains at least one Lys residue, and in some embodiments at least two Lys residues. If a target compound is not a transglutaminase substrate, per se, it is possible to insert one or more Gln or Lys residues, and in particular Lys residues in the protein to make the protein a substrate for transglutaminase. Alternatively, a peptide sequence containing a lysine residue (a peptidic tag) may be inserted. In principle, such Gln or Lys residue may be inserted at any position in the sequence. Typically, the insertion should be at an accessible portion of the protein or in a flexible loop. It can also be inserted at a position where the physiological, such as the therapeutic activity of the protein is not affected to a degree where the protein is not useful anymore, e.g. in a therapeutic intervention. Insertions of amino acid residues in proteins can be brought about by standard techniques known to persons skilled in the art, such as post-translational chemical modification or transgenetic techniques.

Any target compound or protein that is a substrate to transglutaminase can be modified by the methods disclosed herein, such as e.g. enzymes, protein hormones, growth factors, antibodies and antibody fragments, cytokines, receptors, lymphokines and vaccine antigens. In some embodiments, the polypeptide is an antigenic peptide.

In some embodiments, particularly when R is a polysaccharide, the polypeptide is a carrier molecule. In general, covalent conjugation of polysaccharides to carriers enhances the immunogenicity of polysaccharides as it converts them from T-independent antigens to T-dependent antigens, thus allowing priming for immunological memory. Conjugation is particularly useful for pediatric vaccines, (see for example Ramsay et al. Lancet 357(9251): 195-196 (2001)) and is a well-known technique (see reviews in Lindberg Vaccine 17 Suppl 2:S28-36 (1999), Buttery & Moxon, J R Coll Physicians Lond 34, 163-168 (2000), Ahmad & Chapnick, Infect Dis Clin North Am 13:113-33, vii (1999), Goldblatt J. Med. Microbiol. 47, 563-567 (1998), European Patent 477 508, U.S. Pat. No. 5,306,492, WO98/42721, Dick et al. Conjugate Vaccines (eds. Cruse et al.) Karger, Basel, 10, 48-114 (1989) and Hermanson Bioconjugate Techniques, Academic Press, San Diego (1996) ISBN: 0123423368.

The carrier protein may be a bacterial toxin toxoid. Useful carrier proteins include bacterial toxins or toxoids, such as diphtheria toxoid or tetanus toxoid, diphtheria and cholera toxins and their subunits such as fragment C of tetanus toxoid and CRM197 mutant of diphtheria toxin. Other suitable carrier proteins include the *N. meningitidis* outer membrane protein, synthetic peptides, heat shock proteins, pertussis proteins, cytokines, lymphokines, hormones, growth factors, human serum albumin (including recombinant), artificial proteins comprising multiple human CD4+ T cell epitopes from various pathogen-derived antigens, such as N19, protein D from *H. influenzae*, pneumococcal surface protein PspA, pneumolysin, iron-uptake proteins, toxin A or B from *C. difficile*, recombinant *Pseudomonas aeruginosa* exoprotein A (rEPA), a GBS protein, etc. In some embodiments, the target protein is a pilus protein such as a GBS protein, for example GBS67 and GBS80.

Further Derivitization

A need for modifying the target proteins of the present invention (i.e. proteins of interest) may arise for any number of reasons, and this is also reflected in the kinds of compounds that may be selectively modified according to the methods of the present invention.

Generally, the methods of the invention comprise a microbial transglutaminase catalyzed reaction of a protein containing at least two lysines with a glutamine containing peptide of the formula (I) $R^1$-(Leu)$_x$-Gln-(Gly)$_y$-(A-W—B—$R^2$)$_z$ or (II) $R^1$-(Leu)$_x$-Gln-(Gly)$_y$-(NH—W—$R^2$)$_z$.

In one embodiment, the method consists of the following steps: (a) preparation by peptide synthesis of a compound of the formula (I) $R^1$-(Leu)$_x$-Gln-(Gly)$_y$-(A-W—B—$R^2$)$_z$, and purification as known in the art; (b) mixing excess of this compound $R^1$-(Leu)$_x$-Gln-(Gly)$_y$-(A-W—B—$R^2$)$_z$ with a target protein containing at least one lysine, and in some embodiments, more than one lysines in an aqueous buffer, optionally containing an organic solvent, detergent or other modifier; (c) addition to this mixture of a catalytic amount of microbial transglutaminase; (d) a mTGase inhibitor can optionally be added to the mixture; (e) the mixture is subjected to a purification process, typically comprising unit operation such as ultra- or dia-filtration and/or chromatography (ion exchange, size exclusion, hydrophobic interaction, etc.). Selectively modified protein is thereby obtained. The protein is characterized by standard protein analytical methods, including chromatography, electrophoresis, peptide mapping and mass spectroscopy.

In one embodiment, the method consists of the following steps: (a) preparation by peptide synthesis of a compound of the formula (II) $R^1$-(Leu)$_x$-Gln-(Gly)$_y$-(NH—W—$R^2$)$_z$, and purification as known in the art; (b) mixing excess of this compound $R^1$-(Leu)$_x$-Gln-(Gly)$_y$-(NH—W—$R^2$)$_z$ with a target protein containing at least one lysine, and in some embodiments, more than one lysines in an aqueous buffer, optionally containing an organic solvent, detergent or other modifier; (c) addition to this mixture of a catalytic amount of microbial transglutaminase; (d) a mTGase inhibitor can optionally be added to the mixture; (e) the mixture is subjected to a purification process, typically comprising unit operation such as ultra- or dia-filtration and/or chromatography (ion exchange, size exclusion, hydrophobic interaction, etc.). Selectively modified protein is thereby obtained. The protein is characterized by standard protein analytical methods, including chromatography, electrophoresis, peptide mapping and mass spectroscopy.

Optionally, following steps (b) or (c), the modified protein can be further modified via the functional groups of $R^1$ or $R^2$ or both, if present, for example with a fluorophore label (unless one is already present). If a label is added, the modified protein may be detected using a variety of techniques depending on the nature of the label such fluorescence or radiolabelling.

In some embodiments, the functional groups of $R^1$ or $R^2$ or both can be radiolabelled. For example, iodine radio labeling can be added to a linker as shown in Scheme II.

Scheme II.

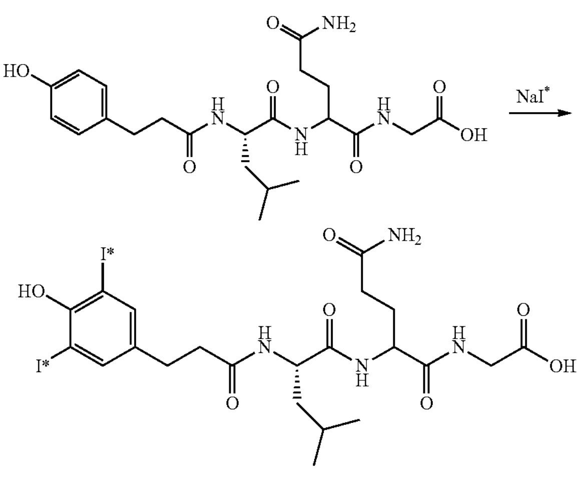

As part of the mechanism of the mTGase-mediated transamidation, an intermolecular thioester is formed by reaction between a Cys in the active site of the MTGase and the Gln substrate. The term "transamidation" is intended to indicate a reaction where nitrogen in the side chain of glutamine is exchanged with nitrogen from another compound, in particular nitrogen from another nitrogen containing nucleophile. This intermediate may be regarded as an activated Gln-residue, the active species being a mTGase-thioester, which reacts with amines, e.g. a protein lysine residue. The selectivity of the reaction is a consequence of 1) the shear steric bulk of the mTGase-thioester while interacting with the Lys-bearing protein substrate, and 2) more defined non-covalent interactions between the mTGase-thioester and the Lys-bearing protein substrate. An immediate consequence of this is that proteins carrying activated acyl groups, Acyl-X-protein, where is X is an atom or group that activates the acyl group towards nucleophilic attack by a protein-lysine amine, is included in the invention.

Thus, it may be desirable to modify proteins to alter the physico-chemical properties of the protein, such as e.g. to increase (or to decrease) solubility to modify the bioavailability of therapeutic proteins. In another embodiment, it may be desirable to modify the clearance rate in the body by conjugating compounds to the protein which binds to plasma proteins, such as e.g. albumin, or which increase the size of the protein to prevent or delay discharge through the kidneys. Conjugation may also alter and in particular decrease the susceptibility of a protein to hydrolysis, such as e.g. in vivo proteolysis.

In another embodiment, it may be desirable to conjugate a label to facilitate analysis of the protein. Examples of such labels include radioactive isotopes, fluorescent markers such as the fluorophores already described and enzyme substrates.

In still another embodiment, a compound is conjugated to a protein to facilitate isolation of the protein. For example, a compound with a specific affinity to a particular column material may be conjugated to the protein. It may also be desirable to modify the immunogenicity of a protein, e.g. by conjugating a protein so as to hide, mask or eclipse one or more immunogenic epitopes at the protein. The term "conjugate" as a noun is intended to indicate a modified peptide, i.e. a peptide with a moiety bonded to it to modify the properties of said peptide. As a verb, the term is intended to indicate the process of bonding a moiety to a peptide to modify the properties of said peptide.

In one embodiment, the invention provides a method of improving pharmacological properties of target proteins. The improvement is with respect to the corresponding unmodified protein. Examples of such pharmacological properties include functional in vivo half-life, immunogenicity, renal filtration, protease protection and albumin binding of any specific protein.

In one aspect, modified proteins of the invention may be further modified thru further derivatization of $R^1$, (A-W—B—$R^2$)$_z$, and/or NH—W—$R^2$. Specifically, $R^1$ and/or $R^2$ may comprise a chemical group suitable for further modification. Examples of such further functionalization include azide-alkyne Huisgen cycloaddition, more commonly known as click chemistry, if $R^1$ or $R^2$ includes an azide or cyclooctyne group. If $R^2$ includes the tosyl sulfone which eliminates to an α,β-unsaturated ketone, conjugate addition could be applied for further modification using a nucleophile such as a thiol.

In some embodiments already described above, W may be selected from: dendrimer, polyalkylene oxide, polyalkylene glycol (PAG), polyethylene glycol (PEG\ polypropylene glycol (PPG), branched PEGs, polyvinyl alcohol (PVA, polycarboxylate, poly-vinylpyrolidone, polydhykne-co-maleic acid anhydride, polystyrene-c-makic acid anhydride, dextrin, carboxymethyl-dextran; serum protein binding-ligands, such as compounds which bind to albumin, such as fatty acids, $C_5$-$C_{24}$ fatty acid, aliphatic diacid (e.g. $C_5$-$C_{24}$), a structure (e.g. sialic acid derivatives or mimetics) which inhibit the glycams from binding to receptors (e.g. asialoglyco-protein receptor and mannose receptor) a small organic molecule containing moieties that alters physiological conditions, alters charge properties, such as carboxylic acids or amines, or neutral substituents that prevent glycan specific recognition such as smaller alkyl substituents (e.g. $C_1$-$C_5$ alkyl), a low molecular organic charged radical (e.g. $C_1$-$C_{25}$), which may contain one or more carboxylic acids, amines, sulfonic, phosphonic acids, or combination thereof; a low molecular neutral hydrophilic molecule (e.g. $C_1$-$C_{25}$), such as cyclodextrin, or a polyethylene chain which may optionally branched; polyethyleneglycol with an average molecular weight of 2-40 KDa; a well-defined precision polymer such as a dendrimer with an exact molecular mass ranging from 700 to 20,000 Da, or more preferably between 700-10.000 Da; and a substantially non-imunogenic polypeptide such as albumin or an antibody or part of an antibody optionally containing a Fc-domain.

In one embodiment, W is a linear or branched polyethylene glycol having a molecular weight of between about 40 and about 10,000 amu, also referred to as a "PEG." The term "PEG" is intended to indicate polyethylene glycol including analogues thereof, for example where a branching terminal OH-group has been replaced by an alkoxy group, such as methoxy group, an ethoxy group, or a propoxy group.

Due to the process for producing mPEG these molecules often have a distribution of molecular weights. This distribution is described by the polydispersity index. The term "polydispersity index" as used herein means the ratio between the weight average molecular weight and the number average molecular weight, as known in the art of polymer chemistry (see e.g. "Polymer Synthesis and Characterization", J. A. Nairn, University of Utah, 2003). The polydispersity index is a number which is greater than or equal to one, and it may be estimated from Gel Permeation Chromatographic data. When the polydispersity index is 1, the product is monodisperse and is thus made up of compounds with a single molecular weight. When the polydispersity index is greater than 1 it is a measure of the polydispersity of that polymer, i.e. the breadth of the distribution of polymers with different molecular weights.

The use of for example "mPEG2000" in formulas, compound names or in molecular structures indicates an mPEG residue wherein mPEG is polydisperse and has a molecular weight of approximately 2,000 Da.

The polydispersity index typically increases with the molecular weight of the PEG or mPEG. When reference is made to 2,000 Da PEG and in particular 2,000 Da mPEG it is intended to indicate a compound (or in fact a mixture of compounds) with a polydisperisty index below 1.06, such as below 1.05, such as below 1.04, such as below 1.03, such as between 1.02 and 1.03. When reference is made to 3,000 Da PEG and in particular 3,000 Da mPEG it is intended to indicate a compound (or in fact a mixture of compounds) with a polydispersity index below 1.06, such as below 1.05, such as below 1.04, such as below 1.03, such as between 1.02 and 1.03.

In some embodiments, the above methods also include a step of controlling the pH environment of the protein to a pH greater than 7 and contacting the site selective labeled protein with a peptide having a cysteine residue. In some embodiments, the peptide having a cysteine residue is $N^5$—((R)-1-

((carboxymethyl)amino)-3-mercapto-1-oxopropan-2-yl)-L-glutamine. In some embodiments, the peptide having a cysteine reside can be substituted with any thiol containing molecule such as polysaccharides with thiols, cytotoxics with thiols, thiol-functionalized PEGs, and the like.

Pharmaceutical Compositions

In another aspect, pharmaceutical compositions comprising a protein modified by any of the methods disclosed herein. In one aspect, such a pharmaceutical composition comprises a modified protein such as growth hormone (GH), which is present in a concentration from 10-15 mg/ml to 200 mg/ml, such as e.g. 10-10 mg/ml to 5 mg/ml and wherein the composition has a pH from 2.0 to 10.0. The composition may further comprise a buffer system, preservative(s), tonicity agent(s), chelating agent(s), stabilizers and surfactants. In one embodiment, the pharmaceutical composition is an aqueous composition. Such compositions typically exist as a solution or a suspension. In a further embodiment, the pharmaceutical composition is an aqueous solution. The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical composition is a freeze-dried composition, to which a physician, patient, or pharmacist adds solvents and/or diluents prior to use. In another embodiment the pharmaceutical composition is a dried composition (e.g. freeze-dried or spray-dried) ready for use without any prior dissolution.

In a further aspect, a pharmaceutical composition comprising an aqueous solution of a modified protein, such as e.g. a Modified GH protein, and a buffer, wherein the modified protein, such as e.g. Modified GH protein is present in a concentration from 0.1-100 mg/ml or above, and wherein said composition has a pH from about 2.0 to about 10.0.

In a another embodiment, the pH of the composition is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment, the buffer is selected from ammonium bicarbonate, sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)aminomethane, bicine, tricine, malic acid, succinate, maleic acid, fumaric acid, tartaric acid, aspartic acid, TRIS, or mixtures thereof.

In a further embodiment, the composition may also include a pharmaceutically acceptable preservative. For example, the preservative may be phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), or mixtures thereof. The preservative may be present in a concentration from 0.1 mg/ml to 20 mg/m or 0.1 mg/ml to 5 mg/ml. In a further embodiment, the preservative is present in a concentration from 5 mg/ml to 10 mg/ml or from 10 mg/ml to 20 mg/ml.

In a further embodiment, the composition may include an isotonic agent. In a further embodiment, the isotonic agent is selected from a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a $C_4$-$C_8$ hydrocarbon having at least one —OH group and includes, for example, mannitol, sorbitol, inositol, galactitol, dulcitol, xylitol, arabitol, and mixtures of the same. In one embodiment, the sugar alcohol additive is mannitol. In one embodiment, the sugar or sugar alcohol concentration is between about 1 mg/ml and about 150 mg/ml, or from 1 mg/ml to 50 mg/ml. The isotonic agent is present in a concentration from 1 mg/ml to 7 mg/ml or from 8 mg/ml to 24 mg/ml, or from 25 mg/ml to 50 mg/ml. The use of an isotonic agent in pharmaceutical compositions is well-known to the skilled person. For convenience, reference is made to Remington: The Science and Practice of Pharmacy, 201h edition, 2000.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenes-ulfonic acids and the like. Further examples of pharmaceutically acceptable inorganic or organic acid addition salts include the pharmaceutically acceptable salts listed in J. Phann. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

In a further embodiment, the composition includes a chelating agent. The chelating agent is selected from salts of ethylenediaminetetraacetic acid (EDTA), citric acid, and aspartic acid, and mixtures thereof. The chelating agent is present in a concentration from 0.1 mg/ml to 5 mg/ml, from 0.1 mg/ml to 2 mg/ml, or from 2 mg/ml to 5 mg/ml. The use of a chelating agent in pharmaceutical compositions is well-known to the skilled person. For convenience, reference is made to Remington: The Science and Practice of Pharmacy, $20^{th}$ edition, 2000.

In a further embodiment, the composition includes a stabilizer. The use of a stabilizer in pharmaceutical compositions is well-known to the skilled person. For convenience, reference is made to Remington: The Science and Practice of Pharmacy, 20th edition, 2000. More particularly, compositions of the invention are stabilized liquid pharmaceutical compositions whose therapeutically active components include a protein that possibly exhibits aggregate formation during storage in liquid pharmaceutical compositions. By "aggregate formation" is intended a physical interaction between the protein molecules that results in formation of oligomers, which may remain soluble, or large visible aggregates that precipitate from the solution. By "during storage" is intended a liquid pharmaceutical composition or composition once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or composition is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Phann. 18:1169-1206; and Mumenthaler et al. (1994) Phann. Res. 11:12-20), or air drying (Carpenter and Crowe (1988) Cryobiology 25:459-470; and Roser (1991) Biopharm. 4:47-53). Aggregate formation by a protein during storage of a liquid pharmaceutical composition can adversely affect biological activity of that protein, resulting in loss of therapeutic efficacy of the pharmaceutical composition. Furthermore, aggregate formation may cause other problems such as blockage of tubing, membranes, or pumps when the protein-containing pharmaceutical composition is administered using an infusion system.

The pharmaceutical compositions may also include an amount of an amino acid base sufficient to decrease aggregate formation by the protein during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L or D isomer, or mixtures thereof) of a particular amino acid (methionine, histidine, arginine, lysine, isoleucine, aspartic acid, tryptophan, threonine and mixtures thereof) or combinations of these stereoisomers or glycine or an organic base such as but not limited to imidazole, may be present in the pharmaceutical compositions so long as the particular amino acid or organic base is present either in its free base form or its salt form. In one embodiment the L-stereoisomer of an amino acid is used. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the protein during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L-cysteine. As with the other amino acids, the amino acid analogues are incorporated into the compositions in either their free base form or their salt form. In a further embodiment, the amino acids or amino acid analogues are used in a concentration, which is sufficient to prevent or delay aggregation of the protein.

In a further embodiment, methionine (or other sulphuric amino acids) or analogous amino acids, may be added to inhibit oxidation of methionine residues to methionine sulfoxide when the protein acting as the therapeutic agent is a protein comprising at least one methionine residue susceptible to such oxidation. By "inhibit" is intended minimal accumulation of methionine oxidized species over time. Inhibiting methionine oxidation results in greater retention of the protein in its proper molecular form. Any stereoisomer of methionine (L or D isomer) or any combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be obtained by adding methionine such that the ratio of methionine added to methionine residues ranges from about 1:1 to about 1000:1, such as 10:1 to about 100:1.

In a further embodiment, the composition may include a stabilizer selected from the group of high molecular weight polymers or low molecular compounds. The stabilizer may be selected from polyethylene glycol (e.g. PEG 3350), polyvinyl alcohol (PV A), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

The pharmaceutical compositions may also include additional stabilizing agents, which further enhance stability of a therapeutically active protein therein. Stabilizing agents include, but are not limited to, methionine and EDTA, which protect the protein against methionine oxidation, and a nonionic surfactant, which protects the protein against aggregation associated with freeze-thawing or mechanical shearing.

In a further embodiment, the composition also includes a surfactant. The surfactant may be selected from a detergent, ethoxylated castor oil, polyglycolyzed glycerides, acetylated monoglycerides, sorbitan fatty acid esters, polyoxypropylenepolyoxyethylene block polymers (e.g. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (e.g. phosphatidyl serine, phosphatidyl choline, phosphatidyl ethanolamine, phosphatidyl inositol, diphosphatidyl glycerol and sphingomyelin), derivates of phospholipids (e.g. dipalmitoyl phosphatidic acid) and lysophospholipids (e.g. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (e.g. cephalins), glyceroglycolipids (e.g. galactopyransoide), sphingoglycolipids (e.g. ceramides, gangliosides), dodecylphosphocholine, hen egg lysolecithin, fusidic acid derivatives—(e.g. sodium tauro-dihydrofusidate etc.), long-chain fatty acids and salts thereof$_6$-$C_{12}$ (e.g. oleic acid and caprylic acid), acylcarnitines and derivatives, $N^{\alpha}$-acylated derivatives of lysine, arginine or histidine, or side-chain acylated derivatives of lysine or arginine, $N^{\alpha}$-acylated derivatives of diproteins comprising any combination of lysine, arginine or histidine and a neutral or acidic amino acid, $N^{\alpha}$-acylated derivative of a triprotein comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, amomc (alkyl-arylsulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), nonionic surfactants (e.g. Dodecyl β-D-glucopyranoside), poloxamines (e.g. Tetronic's), which are tetrafunctional block copolymers derived from sequential addition of propylene oxide and ethylene oxide to ethylenediamine, or the surfactant may be selected from the group of imidazoline derivatives, or mixtures thereof.

The use of a surfactant in pharmaceutical compositions is well-known to the skilled person. For convenience, reference is made to Remington: The Science and Practice of Pharmacy, $20^{th}$ edition, 2000.

It is possible that other ingredients may be present in the pharmaceutical composition. Such additional ingredients may include wetting agents, emulsifiers, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical composition.

Pharmaceutical compositions containing a modified protein, such as e.g. a modified GH protein may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions may be administered in several dosage forms, for example, as solutions, suspensions, emulsions, microemulsions, multiple emulsion, foams, salves, pastes, plasters, ointments, tablets, coated tablets, rinses, capsules, for example, hard gelatin capsules and soft gelatin capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the Modified GH protein, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behavior in lipid-water systems, polymeric micelles, multiple emulsions, self-emulsifying, self-microemulsifying, cyclodextrins and derivatives thereof, and dendrimers.

Compositions are useful in the composition of solids, semi-solids, powder and solutions for pulmonary administration of a modified protein, such as e.g. a Modified GH protein, using, for example a metered dose inhaler, dry powder inhaler and a nebulizer, all being devices well known to those skilled in the art.

Therapeutic Uses of the Modified Proteins

To the extent that the unmodified protein is a therapeutic protein, the invention also relates to the use of the modified proteins in therapy, and in particular to pharmaceutical compositions comprising the modified proteins. Thus, as used herein, the terms "treatment" and "treating" mean the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications, The patient to be treated is preferably a mammal, in particular a human being, but it may also include animals, such as dogs, cats, cows, sheep and pigs. Nonetheless, it should be recognized that therapeutic regimens and prophylactic (preventative) regimens represents separate aspects for the uses disclosed herein and contemplated by treating physician or veterinarian.

A "therapeutically effective amount" of a modified protein as used herein means an amount sufficient to cure, alleviate or partially arrest the clinical manifestations of a given disease and its complications. An amount adequate to accomplish this is defined as "therapeutically effective amount". Effective amounts for each purpose will depend on e.g. the severity of the disease or injury as well as the weight, sex, age and general state of the subject. It will be understood that determining an appropriate dosage may be achieved using routine experimentation, by constructing a matrix of values and testing different points in the matrix, which is all within the ordinary skills of a trained physician or veterinarian.

The methods and compositions disclosed herein provide modified proteins for use in therapy. As such, a typical parenteral dose is in the range of 10-9 mg/kg to about 100 mg/kg body weight per administration. Typical administration doses are from about 0.0000001 to about 10 mg/kg body weight per administration. The exact dose will depend on e.g. indication, medicament, frequency and mode of administration, the sex, age and general condition of the subject to be treated, the nature and the severity of the disease or condition to be treated, the desired effect of the treatment and other factors evident to the person skilled in the art. Typical dosing frequencies are twice daily, once daily, bi-daily, twice weekly, once weekly or with even longer dosing intervals. Due to the prolonged half-lives of the active compounds compared to the corresponding un-conjugated protein, dosing regimen with long dosing intervals, such as twice weekly, once weekly or with even longer dosing intervals is a particular embodiment. Many diseases are treated using more than one medicament in the treatment, either concomitantly administered or sequentially administered. It is, therefore, contemplated that the modified proteins in therapeutic methods for the treatment of one of the diseases can be used in combination with one or more other therapeutically active compound normally used in the treatment of a disease. It is also contemplated that the use of the modified protein in combination with other therapeutically active compounds normally used in the treatment of a disease in the manufacture of a medicament for that disease.

EXAMPLES

General Preparation Methods for Modifying Compounds

Unless otherwise specified, starting materials were generally available from commercial sources such as Aldrich Chemicals Co. (Milwaukee, Wis.), Lancaster Synthesis, Inc. (Windham, N.H.), Acros Organics (Fairlawn, N.J.). Microbial transglutaminase was provided by Ajinomoto North America, Inc. (Itasca, Ill.). $CRM_{197}$ (CAS Number 92092-36-9) is available from Aldrich Chemicals Co. (Milwaukee, Wis.). Monomethyl auristatin F was purchased from Concortis (San Diego, Calif.). Cyclooctyne reagents were purchased from Synaffix (Nijmegen, The Netherlands). MenA antigenic polysaccharide was supplied by Novartis NV&D.

Modifying compounds were purified by column chromatography (Interchim puriflash 430) and analyzed by NMR spectroscopy (400 MHz Bruker), LCMS (Waters Acquity UPLC-UV-CAD-MS), and LCUV (Agilent 1200 series UPLC-UV). Labeled $CRM_{197}$ is characterized by LCMS (UPLC-UV-TOF-MS HRMS Waters Acquity UPLC Qtof). Labeled $CRM_{197}$ is purified by amicon filters (3 kDa or 10 kDa MWCO), and/or SEC (General Electric ÄKTA purifier).

Identification of the protein site of modification (site selectivity) was characterized by protein mapping. The mTGase used in the examples is microbial transglutaminase from Anjinomoto North America, Inc. (Itasca, Ill.).

The following acronyms used in the examples below have the corresponding meanings:

MMAF: monomethylauristatin F mTGase: microbial transglutaminase

MWCO: molecular weight cut off

NHS: N-hydroxysuccinimide

BCN-NHS: (1R,8S,9s)-Bicyclo[6.1.0]non-4-yn-9-ylmethyl N-succinimidyl carbonate

HATU: (O-(7-azabenzotriazol-1-yl)-N,N,N',N'-tetramethyluronium hexafluorophosphate)

RT: room temperature

Rt: retention time

Z-Q-G-NH-$(PEG)_3$-$N_3$

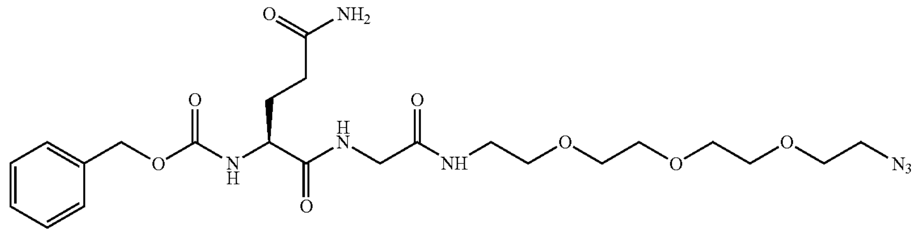 [SMILES: [N-]=[N+]=NCCOCCOCCOCCNC(=O)CNC(=O)[C@H](CCC(N)=O)NC(=O)OCc1ccccc1]

Commercially available ZQG (1 g, 2.96 mmol), Amine-PEG-Azide (0.882 mL, 4.45 mmol), DIPEA (1.553 mL, 8.89 mmol), and HATU (1.127 g, 2.96 mmol) were added together in DMF and stirred at RT for 16 hrs. The solution was loaded directly onto a 55 g C-18 RP column and purified by column chromatography 5-80% MeCN/Water. Due to the large amount of MeOH required to load sample poor peak shape observed. Reduced volume of the desired peak and reloaded onto the column. The product was purified a second time by column chromatography 5-80% MeCN/Water. Yield: 300 mg (19% yield).

$^1H$ NMR (400 MHz, DMSO-d6) δ ppm 1.65-1.79 (m, 1 H) 1.82-1.95 (m, 1 H) 2.07-2.17 (m, 2 H) 3.14-3.26 (m, 2 H) 3.36-3.44 (m, 4 H) 3.46-3.56 (m, 8 H) 3.57-3.62 (m, 2 H) 3.68 (d, J=5.81 Hz, 2 H) 3.91-4.04 (m, 1 H) 5.03 (d, J=2.27 Hz, 2 H) 6.77 (br. s., 1 H) 7.23-7.34 (m, 2 H) 7.34-7.39 (m, 4 H) 7.55 (d, J=7.58 Hz, 1 H) 7.82 (t, J=5.56 Hz, 1 H) 8.16 (t, J=5.68 Hz, 1 H); HRMS calculated for ($C_{23}H_{35}N_7O_8$): 537.2547 observed: (M+1) 538.2623.

ZQ-NH-(PEG)$_3$N$_3$

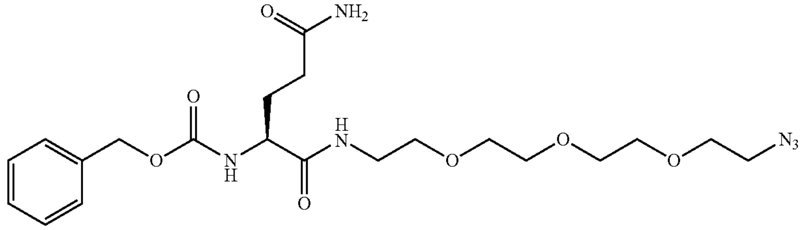 [SMILES: [N-]=[N+]=NCCOCCOCCOCCNC(=O)[C@H](CCC(N)=O)NC(=O)OCc1ccccc1]

Commercially available NH$_2$-(PEG)$_3$-N$_3$ (0.087 mL, 0.318 mmol), Huenig's Base (0.069 mL, 0.398 mmol), and commercially available ZQ-NHS (100 mg, 0.265 mmol) were combined in DMSO and mixed at RT 16 hrs. The reaction was loaded directly onto a 35 g C-18 column for purification 10-75% MeCN/H$_2$O. Yield: 90 mg (70% yield).

$^1$H NMR (400 MHz, DMSO-d6) δ ppm 1.62-1.75 (m, 1 H) 1.77-1.91 (m, 1 H) 2.08 (dt, J=9.14, 5.88 Hz, 2 H) 3.11-3.27 (m, 2 H) 3.35-3.43 (m, 4 H) 3.48-3.56 (m, 8 H) 3.57-3.62 (m, 2 H) 3.94 (td, J=8.31, 5.38 Hz, 1 H) 5.01 (s, 2 H) 6.73 (br. s., 1 H) 7.23 (br. s., 1 H) 7.28-7.41 (m, 6 H) 7.88 (t, J=5.62 Hz, 1 H); HRMS calculated for ($C_{21}H_{32}N_6O_2$): 480.2332 observed: (M+1) 481.2440.

Cyclooctyne-cyclopropyl-CH$_2$—OC(O)NH-Q-G

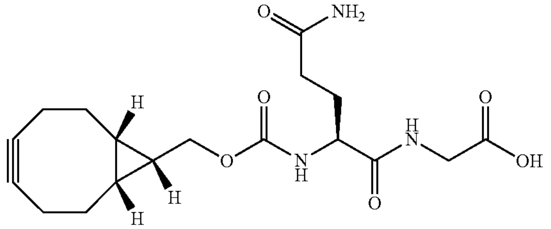 [SMILES: NC(=O)CC[C@H](NC(=O)OC[C@@H]1[C@@H]2CCC#CCC[C@@H]21)C(=O)NCC(=O)O]

Commercially available QG (92 mg, 0.316 mmol) and Huenig's Base (64.5 μL, 0.369 mmol) were dissolved in 2 mL of 1:1 Water:DMSO and warmed to 35° C. Commercially available Click-easy™ BCN N-hydroxysuccinimide ester I (50 mg, 0.246 mmol) was dissolved in 2 mL of DMSO and slowly added to the reaction. The reaction mixed at 40° C. for 1 hr. The product was purified by column chromatography (20 g C-18, 0-70 MeCN/Water). Product eluted around 50% MeCN. Yield: 46 mg (49% yield).

$^1$H NMR (400 MHz, DMSO-d6) δ ppm 0.87 (t, J=9.66 Hz, 2 H) 1.27 (quin, J=8.53 Hz, 1 H) 1.52 (d, J=10.88 Hz, 2 H) 1.62-1.75 (m, 1 H) 1.81-1.95 (m, 1 H) 2.04-2.25 (m, 8 H) 3.14 (br. s., 1 H) 3.49-3.73 (m, 2 H) 3.89-3.99 (m, 1 H) 4.05 (d, J=7.95 Hz, 2 H) 6.72 (br. s., 1 H) 7.21-7.31 (m, 2 H) 7.88 (br. s., 1 H); HRMS calculated for ($C_{18}H_{25}N_3O_6$): 379.1743 observed: (M+1) 380.1811.

Cyclooctyne-cyclopropyl-CH$_2$—OC(O)NH-L-Q-G

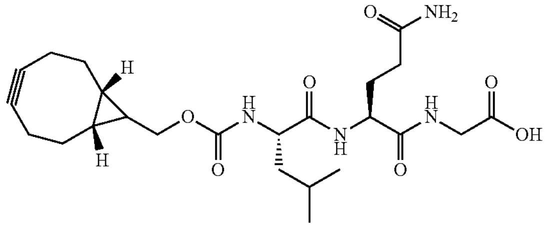 [SMILES: CC(C)C[C@H](NC(=O)OCC1[C@H]2CCC#CCC[C@@H]12)C(=O)N[C@@H](CCC(N)=O)C(=O)NCC(=O)O]

Leucine-glutamine-glycine peptide was prepared using a peptide synthesizer. The synthesizer was programmed for the leucine-glutamine-glycine sequence. The resin was recovered and peptide was removed with TFA. The solution was slowly added to ether (cold) and to precipitate the product. The solution was centrifuged and ether was decanted. The solid was dissolved in water and purified by column chromatography (35 g RP C-18 column) Product eluted with 100% water in 84% yield.

Leucine glutamine glycine peptide (30 mg, 0.07 mmol), Huenig's Base (0.030 mL, 0.174 mmol), and commercially available Click-easy™ BCN N-hydroxysuccinimide ester I (20 mg, 0.070 mmol) were combined in DMF and stirred for five hours at room temp. The reaction was loaded directly onto 20 g C-18 column (0-20% MeCN/Water) and purified over 10 CV to yield 20 mg (58% yield) of the product. HRMS calculated for ($C_{21}H_{32}N_6O_7$): 492.2584 observed: (M+1) 493.2682.

Z-Q-NH-(PEG)$_2$-NHC(O)O—CH$_2$-cyclopropylcy-cloctyne

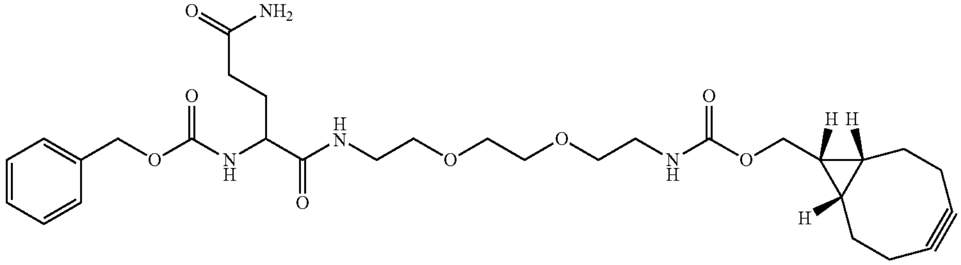 [SMILES: NC(=O)CCC(NC(=O)OCc1ccccc1)C(=O)NCCOCCOCCNC(=O)OC[C@@H]1[C@@H]2CCC#CCC[C@@H]21]

Commercial BocNH-(PEG)3-amine (0.308 mL, 0.994 mmol) in DMSO was added to commercially available ZQ-NHS (250 mg, 0.663 mmol) and stirred at RT for 3 hours. The reaction was loaded directly on to a 30 g C-18 column for purification (0-50% MeCN/Water). The product eluted at 45% MeCN. Solvent was removed to yield a white residue (200 mg, 59.1% yield). LCMS calculated for ($C_{21}H_{32}N_6O_7$): 510.27 observed: (M+1) 511.4.

The Boc-protected product (200 mg, 0.392 mmol) was treated with TFA (3 mL, 38.9 mmol) and shaken at RT for 10 minutes. The reaction was dried on high vacuum overnight and crude ZQ-NH-(PEG)$_2$-NH$_2$ was used directly in next reaction. Huenig's Base (2 mL, 11.45 mmol) was added to ZQ-NH-(PEG)$_2$-NH$_2$ (150 mg, 0.365 mmol) in 1 mL of DMSO. Commercially available BCN-NHS (106 mg, 0.365 mmol) was then added and reaction stirred for several hours. Product was purified by column chromatography (35 g C-18 column 15-75% MeCN/Water). Product eluted under DMSO peak as well as at ~60% MeCN. Combined fractions and concentrated to 10 mL. Ran second column at 20-50% MeCN/water. Product eluted at 45% MeCN. The solvent was removed under reduced pressure to yield 50 mg (23% yield) of product.

$^1$H NMR (400 MHz, DMSO-d6) δ ppm 0.78-0.91 (m, 2 H) 1.26 (quin, J=8.53 Hz, 1 H) 1.41-1.59 (m, 2 H) 1.62-1.75 (m, 1 H) 1.77-1.90 (m, 1 H) 1.95-2.30 (m, 8 H) 3.11 (q, J=5.95 Hz, 2 H) 3.20 (td, J=12.87, 6.66 Hz, 2 H) 3.36-3.42 (m, 4 H) 3.49 (s, 4 H) 3.88-3.98 (m, 1 H) 4.02 (d, J=8.07 Hz, 2 H) 5.01 (s, 2 H) 6.73 (br. s., 1 H) 7.07 (t, J=5.44 Hz, 1 H) 7.23 (br. s., 1 H) 7.29-7.37 (m, 6 H) 7.88 (t, J=5.62 Hz, 1H). HRMS calculated for ($C_{30}H_{42}N_4O_8$): 586.3003 observed: (M+1) 587.3092.

Z-Q-NH—(CH$_2$)$_3$-dimethylacetal

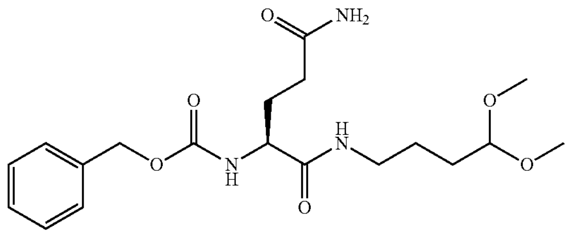 [SMILES: COC(CCCNC(=O)[C@H](CCC(N)=O)NC(=O)OCc1ccccc1)OC]

ZQNHS (100 mg, 0.265 mmol), 4,4-dimethoxybutan-1-amine (0.049 mL, 0.292 mmol), and Huenig's Base (0.046 mL, 0.265 mmol) were dissolved in DMF and mixed at RT for 1 hr. The reaction was loaded directly onto a 35 g C-18 column for purification (0-40% MeCN/H$_2$O). The solvent was removed under reduced pressure to yield 50 mg (48% yield) of the product.

$^1$H NMR (400 MHz, DMSO-d6) δ ppm 1.30-1.43 (m, 2 H) 1.43-1.54 (m, 2 H) 1.58-1.75 (m, 1 H) 1.76-1.89 (m, 1 H) 2.01-2.16 (m, 2 H) 3.04 (dt, J=12.57, 6.47 Hz, 2 H) 3.19 (s, 6 H) 3.89 (td, J=8.46, 5.31 Hz, 1 H) 4.32 (t, J=5.56 Hz, 1 H) 5.00 (s, 2 H) 6.76 (br. s., 1 H) 7.26 (br. s., 1 H) 7.28-7.42 (m, 6 H) 7.86 (t, J=5.68 Hz, 1 H) LCMS calculated for ($C_{19}H_{29}N_3O_6$): 395.21 observed: (M+1) 396.5.

Z-Q-NH—(CH$_2$)$_2$—NH—C(O)—CH$_2$-Alexafluor647

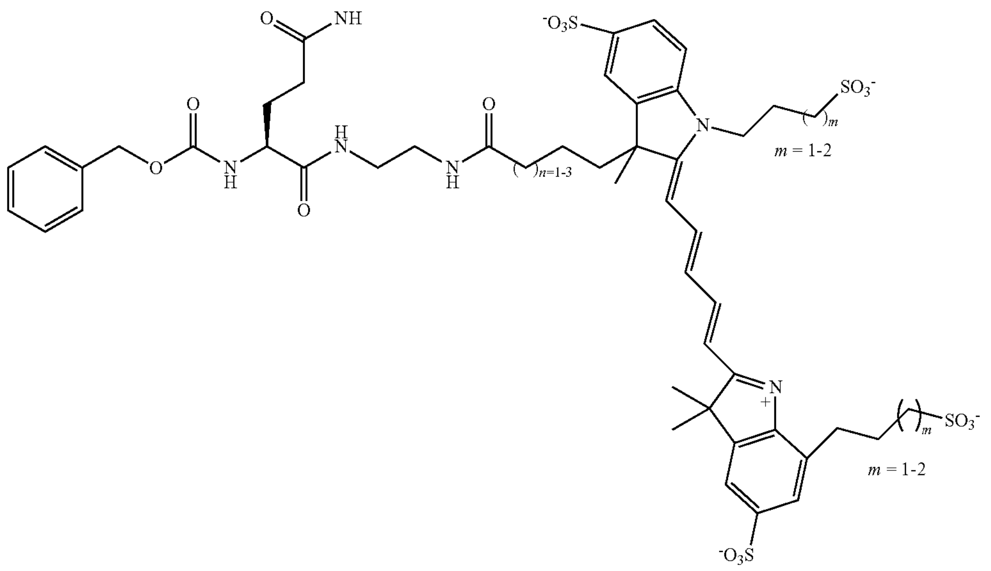

Commercially available ZQ-NHS (286 mg, 0.758 mmol), Huenig's Base (0.5 mL, 2.86 mmol) and tert-butyl(2-aminoethyl)carbamate (0.3 mL, 1.498 mmol) were combined in DCM and sonicated. The solution stirred 16 hours. The reaction was filtered and washed with DCMm followed by evaporation. The residue was dissolved in MeOH/DCM 1:10, and passed through a $HCO_3$ catch and release column to remove the acid side product. The resulting product was treated with TFA (1 mL, 12.98 mmol) in 15 mL of DCM were added. Reaction mixed for 30 minutes and then evaporated on rotovap. The residue was dissolved in MeOH/DCM 1:10 and passed through a $HCO_3$ catch and release column to remove acid side product. The solvent was removed to yield 300 mg (91% yield) of the product.

The resulting amine linker (5.1 mg, 0.016 mmol) was dissolved in DMSO (0.5 mL) and Huenig's Base (3.66 μl, 0.021 mmol) was added followed by Alexflour647 (5 mg, 5.24 μmol). The reaction stirred at room temp for X. The reaction was loaded directly onto a 35 g C-18 column for column chromatography purification (5-35% MeCN/Water). Product eluted ~10% MeCN. The product was lyophilized to yield a dark purple powder. Yield: 3.5 mg (57% yield). HRMS calculated for ($C_{51}H_{67}N_6O_{17}S_4^+$): mass expected: 1163.34 mass observed: M+1, 1164.

Z-Q-NH—$(CH_2)_2$—C(O)—$(CH_2)_2$—$SO_2$-Tol

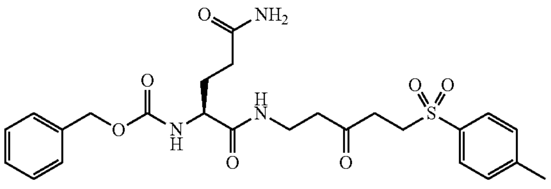 [SMILES: Cc1ccc(S(=O)(=O)CCC(=O)CCNC(=O)[C@H](CCC(N)=O)NC(=O)OCc2ccccc2)cc1]

3-((tert-butoxycarbonyl)amino)propanoic acid (2 g), HATU (4.42 g), Huenig's Base (4.62 mL) and N,O-dimethylhydroxylamine hydrochloride (1.134 g) were combined in DCM and stirred at RT for two hours. The reaction was poured into water and the organics were extracted. The organic layer was evaporated to yield crude yellow oil. The product was purified by column chromatography (50 g C-18, 10-70% MeCN/Water). Fractions collect and concentrated to yield a yellow oil Yield: 1.3 g, 53% yield. Expected Mass: 232, Observed M+1: 233.

tert-Butyl (3-(methoxy(methyl)amino)-3-oxopropyl)carbamate (1.3 g, 5.60 mmol) was dissolved in dry THF and the flask was purged with nitrogen. The solution was cooled to 0° C. then vinylmagnesium bromide (20 ml, 20.00 mmol) in THF was slowly added. The reaction warmed to RT ON. The reaction was poured into cold sat. $NH_4Cl$ and extracted with ethyl acetate. The organics were dried and the solvent was removed on rotovap. The crude material was carried on.

tert-Butyl (3-oxopent-4-en-1-yl)carbamate and 4-methylbenzenethiol were combined in MeOH and stirred at RT 3 days. Methanol was removed by rotovap to yield a thick oily yellow residue. The residue was dissolved in DCM and washed with water 2×. The organic layer was dried and the solvent removed on rotovap to yield a yellow oil. This product (1 g, 3.09 mmol) was dissolved in DCM and cooled to 0° C. TFA (3 mL, 38.9 mmol) was slowly added then warmed to RT and stirred for 1 hour. Solvent was removed and residue was dissolved in DCM and passed through a carbonate catch and release column followed by a carboxylic acid catch and release. Product went through both. Columns were washed, the solvent was combined and then solvent by rotovap. Product was purified by column chromatography (50 g C-18 10-70% MeCN/Water). The product was collected solvent removed by evaporation to yield a yellow oil. The product was collected and the solvent was removed by evaporation to yield a yellow oil. The product was carried on without any further purification. 850 mg, quantitative yield.

1-Amino-5-(p-tolylthio)pentan-3-one (100 mg, 0.448 mmol) and Huenig's Base (0.130 mL, 0.746 mmol) were dissolved in DMF then commercially available ZQ-NHS (141 mg, 0.373 mmol) was added and mixed at RT. The product was purified by column chromatography (25 g C-18 column 10-75% MeCN/Water). The product was collected and organics evaporated by rotovap. MeOH was added to the sulfide linker in water. Oxone (229 mg, 0.373 mmol) was added and the reaction stirred at RT ON. The reaction was filtered and purified by column chromatography (25 g C-18 column 10-75% MeCN/Water) and product was lyophilized to 75 mg (39% yield).

$^1$H NMR (400 MHz, DMSO-d6) δ ppm 1.59-1.72 (m, 1 H) 1.75-1.89 (m, 1 H) 2.06 (dt, J=8.99, 5.90 Hz, 1 H) 2.42 (s, 3 H) 2.60 (t, J=6.60 Hz, 2 H) 2.77 (t, J=7.40 Hz, 2 H) 3.11-3.26 (m, 2 H) 3.39-3.48 (m, 2 H) 3.86 (td, J=8.28, 5.32 Hz, 1 H) 5.01 (d, J=1.83 Hz, 3 H) 6.74 (br. s., 1 H) 7.23 (br. s., 1 H) 7.28-7.42 (m, 6 H) 7.47 (d, J=8.19 Hz, 2 H) 7.78 (d, J=8.19 Hz, 2 H) 7.83 (t, J=5.50 Hz, 1 H). HRMS calculated for ($C_{25}H_{31}N_3O_7S$): mass expected: 517.1883 mass observed: M+1, 518.1974.

Ac-L-Q-G-NH—$(CH_2)_2$—C(O)—$(CH_2)_2$—$SO_2$-Tol

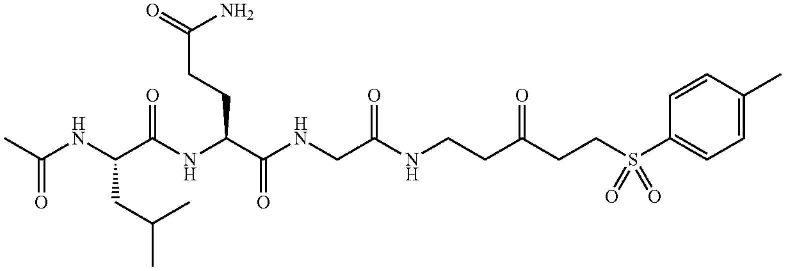 [SMILES: CC(=O)N[C@@H](CC(C)C)C(=O)N[C@@H](CCC(N)=O)C(=O)NCC(=O)NCCC(=O)CCS(=O)(=O)c1ccc(C)cc1]

1-Amino-5-(p-tolylthio)pentan-3-one was prepared as described above in the synthesis of Z-Q-NH—$(CH_2)_2$—C(O)—$(CH_2)_2$—$SO_2$-Tol. LQG was prepared as described above in the synthesis of Cyclooctyne-cyclopropyl-$CH_2$—OC(O)NH-L-Q-G. LQG was acelated at the N-terminus by combining LQG (27 mg, 0.085 mmol), Ac2O (9.66 μl, 0.102 mmol) and Huenig's Base (0.045 mL, 0.256 mmol) in DCM and stirring at RT for several hours. The solvent was evaporated and water was added. The product was lyophilized and used directly in the next reaction. LCMS Observed Mass: (M+1) 359.2; Desired Mass: 358.4

Ac-LQG (38 mg, 0.106 mmol), 1-Amino-5-(p-tolylthio)pentan-3-one (47.4 mg, 0.212 mmol), and Huenig's Base (0.074 mL, 0.424 mmol) were combined in DMF. HATU (40.3 mg, 0.106 mmol) was added and the reaction stirred at RT ON. Product was purified by column chromatography (35 g C-18 column 10-50% MeCN/Water) to yield.

The sulfide (13.5 mg, 0.024 mmol) was dissolved in 1:1 Water:MeOH. Oxone (44.2 mg, 0.072 mmol) was added and the reaction stirred at RT ON. The product was purified by column chromatography (25 g C-18 column 10-60% MeCN/Water).

$^1H$ NMR (400 MHz, DMSO-d6) δ ppm 0.85 (dd, J=16.08, 6.54 Hz, 6 H) 1.36-1.45 (m, 2 H) 1.59 (dt, J=13.27, 6.57 Hz, 1 H) 1.69-1.79 (m, 1 H) 1.83 (s, 3 H) 2.00-2.14 (m, 2 H) 2.41 (s, 3 H) 2.57-2.64 (m, 2 H) 2.75 (t, J=7.40 Hz, 2 H) 3.18 (q, J=6.52 Hz, 1 H) 3.27 (s, 2 H) 3.41 (t, J=7.40 Hz, 2 H) 3.59 (dd, J=5.75, 3.18 Hz, 2 H) 4.07-4.17 (m, 1 H) 4.21-4.30 (m, 1 H) 6.74 (br. s., 1 H) 7.24 (br. s., 1 H) 7.46 (d, J=7.95 Hz, 2 H) 7.68 (t, J=5.50 Hz, 1 H) 7.76 (d, J=8.31 Hz, 2 H) 7.93-8.05 (m, 2 H) 8.11 (d, J=7.09 Hz, 1 H) HRMS calculated for ($C_{27}H_{41}N_5O_8S$) Desired Mass: 595.2676 Observed Mass: (M+1) 596.2755.

Z-Q-NH—$(CH_2)_4$—C(O)—$(CH_2)_2$—$SO_2$-Tol again. The product was purified by column chromatography (25 g column 0-45% EtOAc/Hep) to 385 mg (32.5% yield).

Tert-Butyl (6-(methoxy(methyl)amino)-6-oxohexyl)carbamate (385 mg, 1.403 mmol) was dissolved in dry THF and cooled to 0° C. Vinylmagnesium bromide (4.210 mL, 4.21 mmol) was slowly added. The reaction was allowed to warm to RT overnight. The reaction was poured into sat. $NH_4Cl$ and organics were extracted with EtOAc. The organic layer was washed with water and brine, dried and evaporated. The product was purified by column chromatography (Sunfire RP HPLC 10-40% MeCN/Water 0.1% TFA over 10 minutes 226 nm UV) to give 280 mg (83% yield).

Tert-Butyl (6-oxooct-7-en-1-yl)carbamate (280 mg, 1.160 mmol) and 4-methylbenzenethiol (173 mg, 1.392 mmol) were dissolved in MeOH and stirred at RT for 16 hrs. Methanol was removed and the product was purified by chromatography (25 g column 0-30% EtOAc/Hep) to yield 160 mg (38% yield).

Tert-Butyl (6-oxo-8-(p-tolylthio)octyl)carbamate (160 mg, 0.438 mmol) and ozone (807 mg, 1.313 mmol) were combined together in MeOH/Water 50/50 and stirred at RT for 16 hours. The reaction was poured into water and extracted with DCM. The organic layer was dried by evaporation and 4 Molar HCl in dioxane was added and stirred at RT for several hours. The solvent was removed by evaporation to yield an off-white residue. The product was purified by a Sunfire RP HPLC (10-40% MeCN/Water 0.1% TFA) to yield 33 mg (25% yield).

8-amino-1-tosyloctan-3-one (20 mg, 0.067 mmol) and commercially available ZQNHS (23.07 mg, 0.061 mmol) were combined in DMSO and mixed at 37° C. for an hour. Reaction not complete and no progress was observed after several hours. Huenig's Base (5.34 μl, 0.031 mmol) was added and the reaction advanced. The reaction was loaded

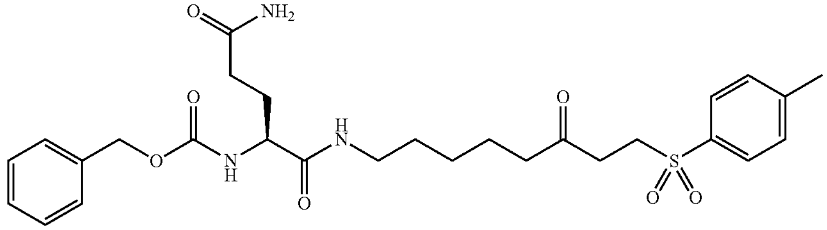 [SMILES: Cc1ccc(S(=O)(=O)CCC(=O)CCCCCNC(=O)[C@H](CCC(N)=O)NC(=O)OCc2ccccc2)cc1]

6-((tert-Butoxycarbonyl)amino)hexanoic acid (1 g, 4.32 mmol) was dissolved in DCM then N,O-dimethylhydroxylamine hydrochloride (0.464 g, 4.76 mmol), HATU (1.808 g, 4.76 mmol), and TEA (0.723 mL, 5.19 mmol) were added. The reaction stirred at RT for several hours, reaction not complete, so additional amine, HATU, and TEA added. The reaction stirred 16 hrs. The reaction was filtered and solvent was evaporated. Ether was added and the reaction was filtered directly onto column (6 g C-18 0-75% MeCN/Water) for purification. Column ran twice to 2.4 mg (7% yield).

$^1H$ NMR (400 MHz, DMSO-d6) δ ppm 1.17 (q, J=7.58 Hz, 2 H) 1.28-1.44 (m, 4 H) 1.61-1.75 (m, 1 H) 1.77-1.90 (m, 1 H) 2.00-2.16 (m, 2 H) 2.37-2.43 (m, 5 H) 2.74 (t, J=7.34 Hz, 2 H) 2.92-3.08 (m, 2 H) 3.43 (t, J=7.34 Hz, 2 H) 3.90 (td, J=8.31, 5.50 Hz, 1 H) 5.01 (s, 2 H) 6.74 (br. s., 1 H) 7.25 (br. s., 1 H) 7.28-7.40 (m, 6 H) 7.46 (d, J=7.82 Hz, 2 H) 7.77 (d, J=8.31 Hz, 2 H) 7.78-7.84 (m, 1 H). HRMS calculated for ($C_{28}H_{37}N_3O_7S$): 559.2352 observed: (M+1) 560.2426.

Z-Q-NH-MenA Polysaccharide

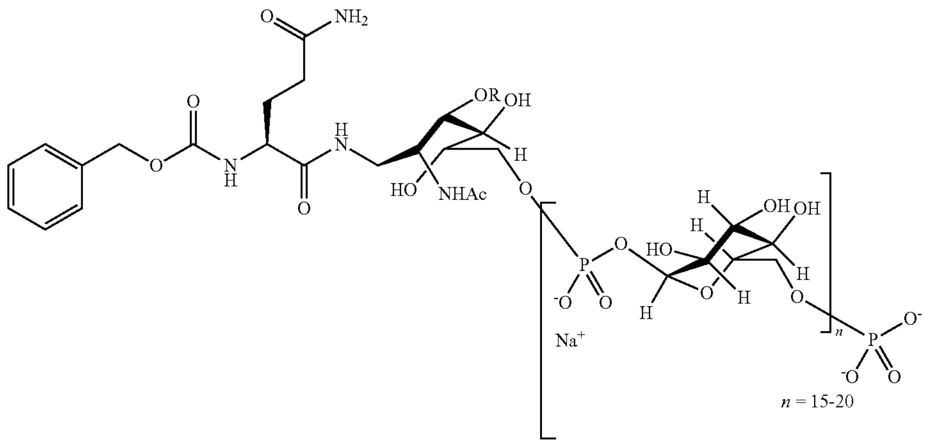

Amine functionalized MenA antigenic polysaccharide (10 mg) was added to commercially available ZQNHS (10 mg 26.4 umol) in DMSO with base and stirred for several hours. The reaction was lyophilized, dissolved in water, and purified by a 10 KD Amicon filter 4×. The flow through was then passed through a 3 KD Amicon to recover additional product. This was carried on crude with an estimated yield of ~50%.

Z-Q-NH—$(CH_2)_5$—C(O)-monomethylauristatin F

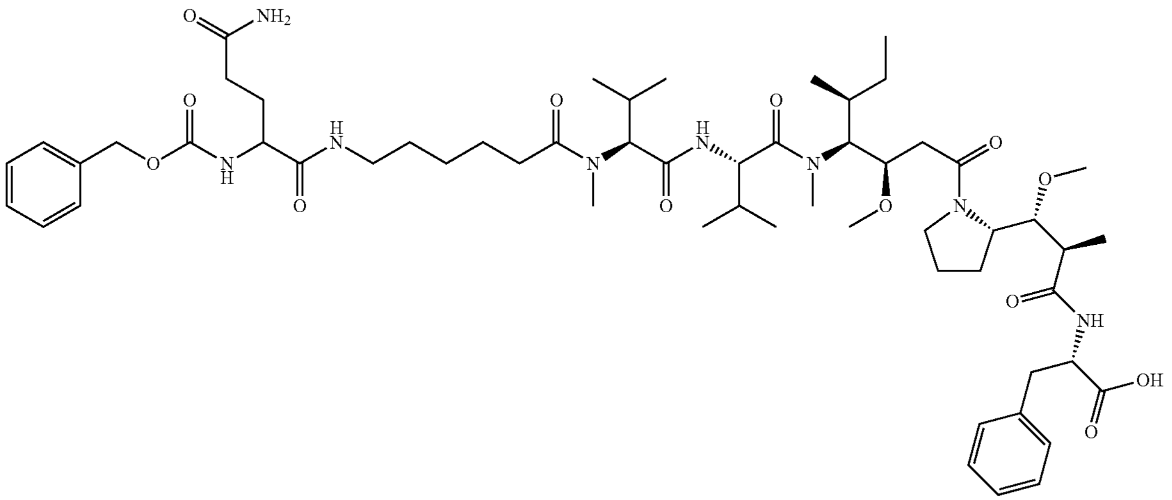 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCCCCNC(=O)C(CCC(N)=O)NC(=O)OCc1ccccc1)C(C)C]

6-((tert-butoxycarbonyl)amino)hexanoic acid (46.5 mg, 0.201 mmol) was dissolved in DMSO (1 mL) and Huenig's Base (0.08 mL, 0.458 mmol) and HATU (76 mg, 0.201 mmol) were added. The reaction stirred at RT for 30 minutes before adding the reaction mixture to MMAF (50 mg, 0.067 mmol). The reaction then stirred at RT for 4 hours. The reaction mixture was loaded directly onto 35 g C-18 column for purification by column chromatography (5-75% MeCN/Water 0.1% formic acid). The solvent was removed on rotovap and placed on high vac overnight.

The resulting product was treated with TFA (2 mL) at 0° C. and brought to room temp to stir for 5 min. The reaction was loaded directly onto a 35 g C-18 column for column purification. The solvent was removed under reduced pressure to yield 30 mg (52% yield).

The deprotected amine (20 mg, 0.023 mmol) was dissolved in THF then LiOH (1 mL, 4.00 mmol) was added. The reaction stirred at RT for 30 minutes was then loaded directly onto column (35 g C-18 column) for purification (0% MeCN followed by 20-40% MeCN/Water). Product eluted with THF and column rerun under above conditions to yield 10 mgs in 51% yield.

The resulting product (5 mg, 5.92 μmol) was dissolved in DMSO, added to commercially available ZQNHS (4.4 mg, 0.012 mmol), and stirred at 37° C. for 20 minutes. The reaction mixture was loaded directly onto a 25 g C-18 column for column chromatography purification (20-75% MeCN/Water). The solvent was removed under reduced pressure to yield 3 mg in 46% yield. LCMS calculated for $(C_{21}H_{32}N_6O_2)$: 1106.6627 observed: (M+1) 1107.9.

Phenol-$(CH_2)_2$—C(O)-L-Q-G

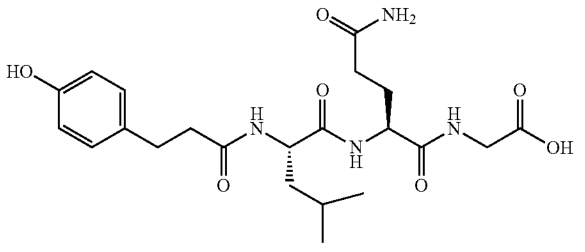 [SMILES: CC(C)C[C@H](NC(=O)CCc1ccc(O)cc1)C(=O)N[C@@H](CCC(N)=O)C(=O)NCC(=O)O]

LQG was prepared as described in "Synthesis of Cyclooctyne-cyclopropyl-$CH_2$—OC(O)NH-L-Q-G" above. Commercially available 2,5-dioxopyrrolidin-1-yl 3-(4-hydroxyphenyl)propanoate (14.65 mg, 55.6 μmol) was added to LQG (16 mg, 50.6 μmol) in DMSO with Huenig's Base (18 uL, 101 μmol) and reaction stirred at room temp overnight. Reaction loaded directly on 20 g column for purification (10-50% MeCN/Water) to yield 13 mg of product for a 55% yield. HRMS calculated for ($C_{21}H_{32}N_6O_2$): 464.2271 observed: (M+1) 465.2356.

ZQ$(PEG)_2$azidobenzylamide

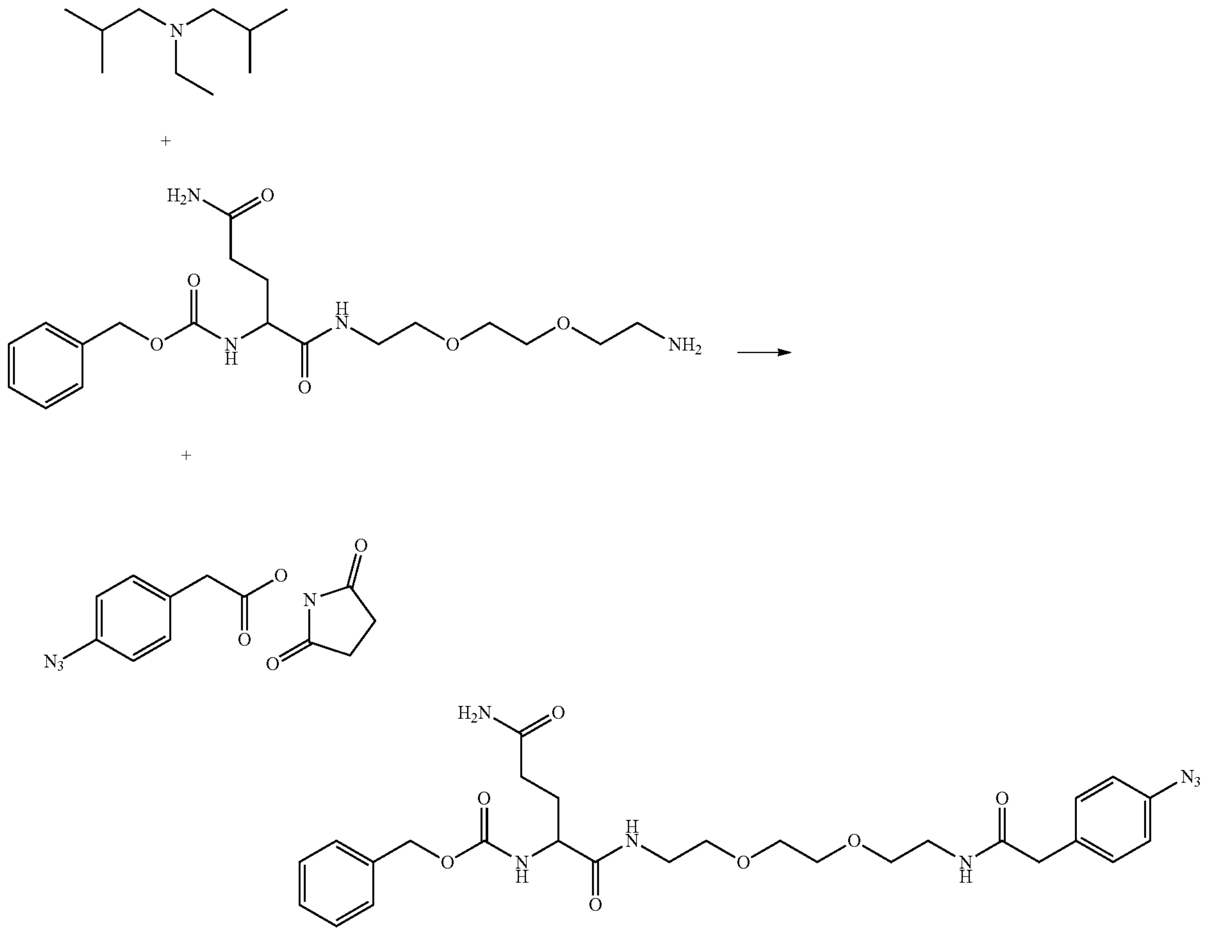

4-Azidophenylacetic acid N-succinimido ester (ChemPacific, 26.7 mg. 0.073 mmol) was dissolved in DMF (1 mL) and combined with a solution of benzyl (5-amino-1-((2-(2-(2-aminoethoxy)ethoxy)ethyl)amino)-1,5-dioxopentan-2-yl)carbamate (20 mg, 0.049 mmol) in DMF (2.3 mL). DIPEA (0.121 mL, 0.585 mmol) was added and the reaction was mixed at r.t. for 4 hours at which point DIPEA (61 μL, 6 eq.) and 4-azidophenylacetic acid N-succinimido ester (9 mg, 0.024 mmol) were added. The reaction was mixed at r.t. for 2 days. 4-azidophenylacetic acid N-succinimido ester (89 mg, 0.24 mmol) was added and the reaction was stirred at r.t. for 2 hours. The solution was purified via MS-triggered HPLC (100-Prep3; Acid Method 3; Sunfire 30×50 mm 5 μm column ACN/$H_2O$ w/0.1% TFA 75 ml/min, A: Water (0.1% formic acid); B: ACN gradient 0 min 5% B; 5% to 95% B in 1.70 min; 2.0 min 95% B; 2.1 min 5% B flow rate 2 ml/min 1.5 ml injection; Tube Trigger M=570). Fractions with desired product were pooled and lyophilized to give 3.6 mg of light yellow powder (13%) of ZQ(PEG2)azido-benzylamide (benzyl (17-amino-1-(4-azidophenyl)-2,13,17-trioxo-6,9-dioxa-3,12-diazaheptadecan-14-yl)carbamates). LCMS SQ2; Product Analysis-Acidic; $R_t$=1.79: MS [M+H] observed: 570.3, calculated: 569.6.

ZQ(PEG)$_2$amidoethylmethyldiazirin

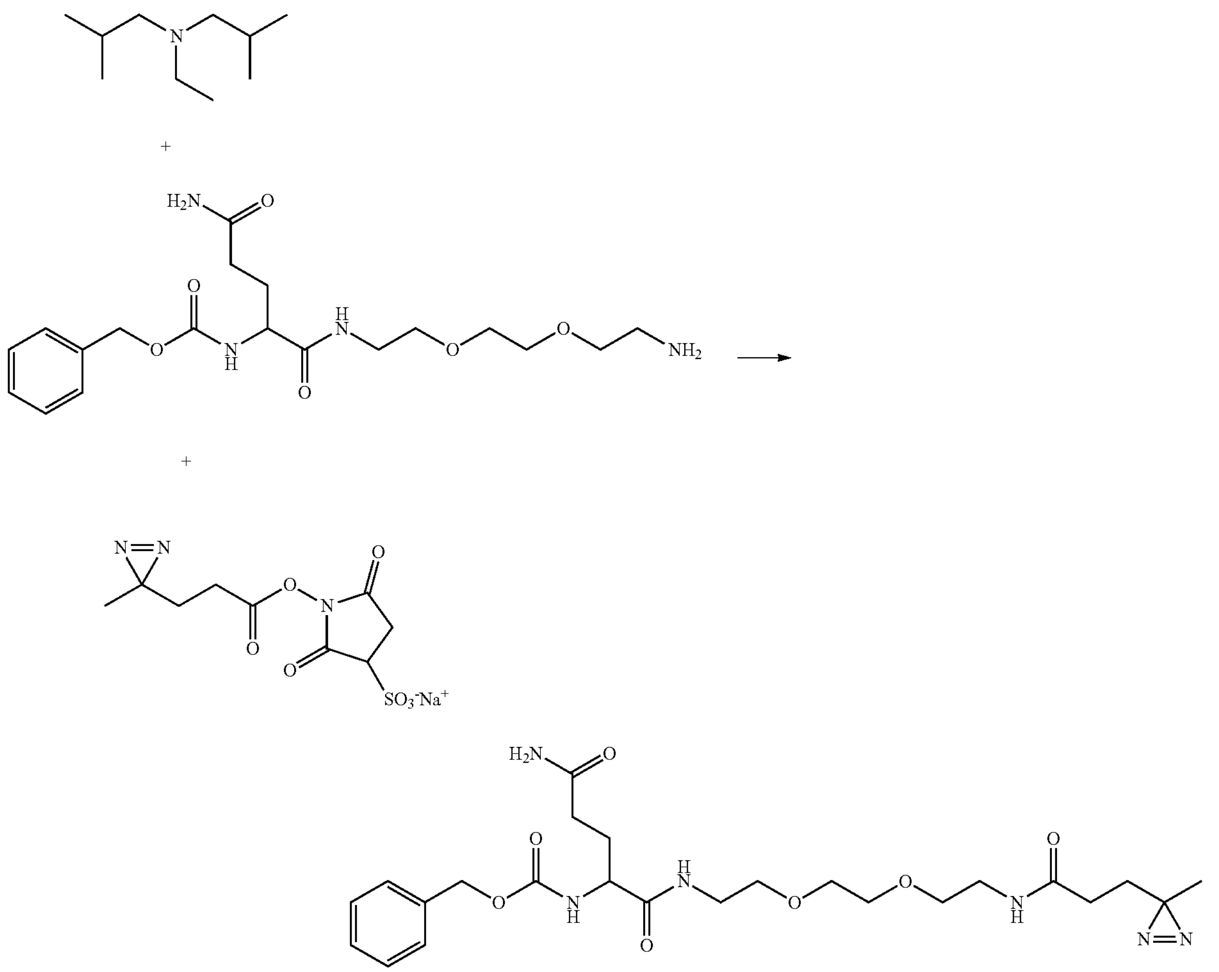

Sulfo-NHS-diazirine (Thermo Scientific, 23.92 mg, 0.073 mmol) was dissolved in DMF (1 mL) and combined with a solution of benzyl (5-amino-1-((2-(2-(2-aminoethoxy)ethoxy)ethyl)amino)-1,5-dioxopentan-2-yl)carbamate (20 mg, 0.049 mmol) in DMF (2.3 mL). The reactants were stirred to combine and DIPEA (0.121 mL, 0.585 mmol) was added. The reaction was stirred at r.t. for 2 hours at which point the reaction became cloudy and 0.5 mL DMF was added. The reaction was stirred for an additional 2 hours and DIPEA (61 μL) and sulfo-NHS-diazirine (8 mg) were added. The reaction was mixed at r.t. for 16 hours at which point the consumption of starting material was observed by LCMS analysis. The solution was purified via MH-triggered HPLC (100-Prep3; Acid Method 3; Sunfire 30×50 mm Sum column ACN/$H_2O$ w/0.1% TFA 75 ml/min, 1.5 ml injection; Tube Trigger M=521). Fractions with the desired product, ZQ(PEG)$_2$amidoethylmethyldiazirin (benzyl (18-amino-1-(3-methyl-3H-diazirin-3-yl)-3,14,18-trioxo-7,10-dioxa-4,13-diazaoctadecan-15-yl)carbamate) were pooled and lyophilized to give 2 mg of the desired compound as a white powder (8%). LCMS SQ2; Product Analysis-Acidic; $R_t$=1.49: MS [M+H] observed: 521.4, calculated: 520.6.

2-(((2,5-Dioxopyrrolidin-1-yl)oxy)carbonyl)-2-undecyltridecanedioic acid

A solution of DCC (126 mg, 0.610 mmol) in DCM (1.57 mL) was added to a solution of intermediate 4 and N-hydroxysuccinimide in DCM (5 mL) and THF (5 mL) under $N_2$. After 3.5 hours, the solvent was evaporated and the residue purified by supercritical fluid chromatography (SFC; Princeton 2-ethyl-pyridine, 20×150 mm, 20-30% MeOH/$CO_2$), yielding the title compound as a colorless oil (138 mg, 0.256 mmol, 50%): LCMS method B Rt=1.21 min, M+H 540.5; $^1$H NMR (600 MHz, ACETONITRILE-d3) δ ppm 0.91 (t, J=7.20 Hz, 3 H) 1.22-1.42 (m, 34 H) 1.57 (quin, J=7.34 Hz, 2 H) 1.93-1.96 (m, 2 H) 2.28 (t, J=7.47 Hz, 2 H) 2.79 (br. d, J=6.30 Hz, 4 H).

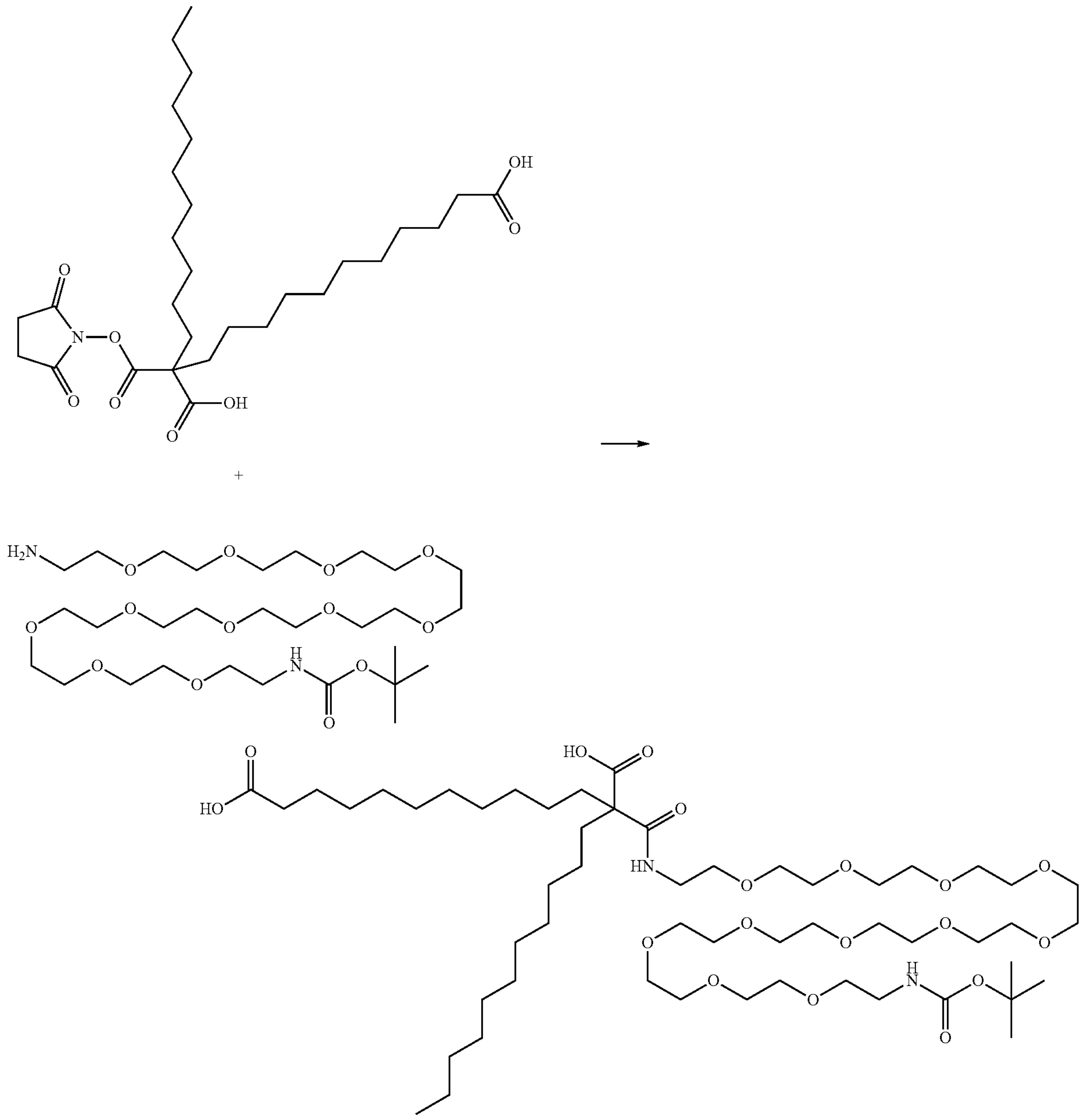

2-((2,2-Dimethyl-4-oxo-3,8,11,14,17,20,23,26,29,32,35,38-dodecaoxa-5-azatetracontan-40-yl)carbamoyl)-2-undecyltridecanedioic acid t-Boc-N-amido-dPEG®$_{11}$-amine (100 mg, 0.155 mmol, Quanta Biodesign) and 2-((2,5-Dioxopyrrolidin-1-yl)oxy)carbonyl)-2-undecyltridecanedioic acid (80 mg, 0.148 mmol) were dissolved in THF (3 mL) and stirred at room temperature under nitrogen nitrogen. After 30 minutes, DIPEA (0.05 mL, 0.286 mmol) was added and the reaction mixture stirred at room temperature overnight. Complete conversion was observed by LCMS (Acidic Eluent A: Water+0.05% Trifluoroacetic Acid, Eluent B: ACN, column Sunfire C18 3.5 μm 3.0×30 mm −40° C., 5-95% gradient 2 minutes, retention time 1.92 min). The reaction mixture was concentrated under reduced pressure, then dissolved in about 1.5 mL of acetonitrile. Purified on a MS-triggered HPLC (Sunfire 30×50 mm Sum column ACN/H2O w/0.1% TFA 75 ml/min 1.5 ml injection, 65-95% ACN 3.5 min gradient, retention time 3.23 minutes) and the fractions pooled and lyophilized to give 85 mg clean product in 54% yield. Clear oil. LCMS: SQ4, RXN-MON-Acidic-NonPolar Rt=1.18 mM, M+H 1070.1; $^{1}$H NMR (400 MHz, ACETONITRILE-d$_{3}$) δ ppm 0.82-1.03 (m, 1 H) 1.11-1.37 (m, 10 H) 1.37-1.51 (m, 2 H) 1.51-1.64 (m, 1 H) 1.69-1.82 (m, 1 H) 1.90-2.04 (m, 66 H) 2.05-2.21 (m, 8 H) 2.21-2.42 (m, 1 H) 3.17-3.28 (m, 1 H) 3.40-3.68 (m, 13 H).

2-((35-Amino-3,6,9,12,15,18,21,24,27,30,33-undecaoxapentatriacontyl)carbamoyl)-2-undecyltridecanedioic acid

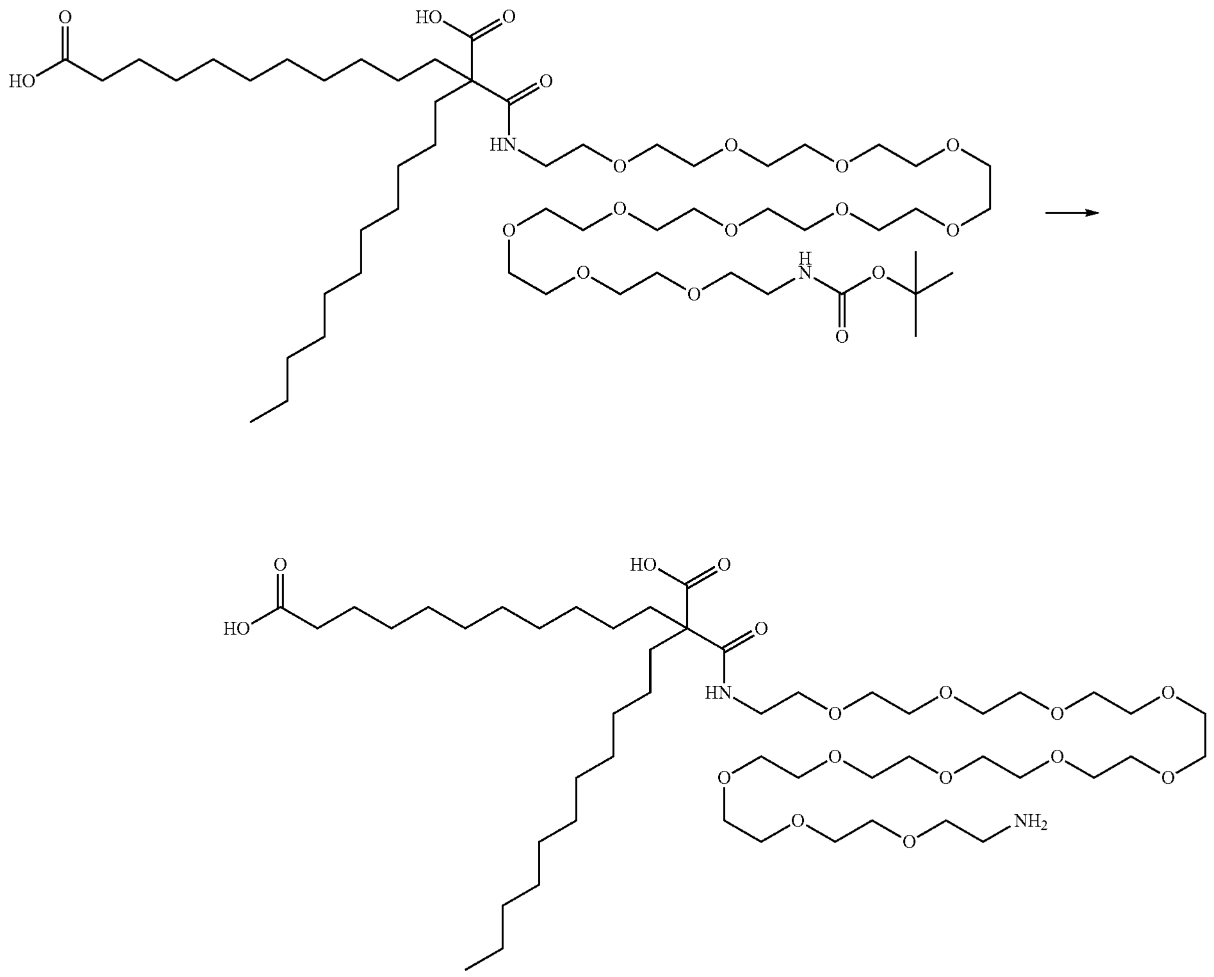

2-((2,2-Dimethyl-4-oxo-3,8,11,14,17,20,23,26,29,32,35,38-dodecaoxa-5-azatetracontan-40-yl)carbamoyl)-2-undecyltridecanedioic acid (5 mg, 4.68 μmol) was dissolved in DCM (Volume: 2 mL), then trifluoroacetic acid (25 μl, 0.324 mmol) was added. The reaction mixture was stirred at room temperature under nitrogen atmosphere for about 2 hours. Complete conversion was observed by LCMS (Acidic Eluent A: Water+0.05% Trifluoroacetic Acid, Eluent B: ACN, column Sunfire C18 3.5 μm 3.0×30 mm −40° C., 5-95% gradient 2 minutes, retention time 1.45 min) The reaction mixture was concentrated under reduced pressure, then rinsed with DCM and concentrated again 3 times. Dissolved in a mixture of acetonitrile and DMSO. Purified on a MS-triggered HPLC (Sunfire 30×50 mm Sum column ACN/H2O w/0.1% TFA 75 ml/min 1.5 ml injection, 45-70% ACN 3.5 min gradient, retention time 2.50 minutes) and the fractions pooled and lyophilized to give 2.5 mg clean product in 55% yield. Clear oil.

LCMS ZQ1 RXNMON_Acidic Rt=1.45 min, M+H 969.9; $^1$H NMR (400 MHz, ACETONITRILE-$d_3$) δ ppm 0.62-0.91 (m, 2 H) 0.91-1.10 (m, 3 H) 1.10-1.31 (m, 18 H) 1.46 (quin, J=7.21 Hz, 2 H) 1.59-1.89 (m, 35 H) 1.94-2.09 (m, 1 H) 2.16 (t, J=7.40 Hz, 2 H) 2.97-3.11 (m, 1 H) 3.24-3.37 (m, 1 H) 3.37-3.61 (m, 28 H) 3.61-3.89 (m, 2 H) 7.85 (br. s., 1 H).

2-(((S)-5-(3-Amino-3-oxopropyl)-3,6-dioxo-1-phenyl-2,10,13,16,19,22,25,28,31,34,37,40-dodecaoxa-4,7-diazadotetracontan-42-yl)carbamoyl)-2-undecyltridecanedioic acid (ZQ-FA)

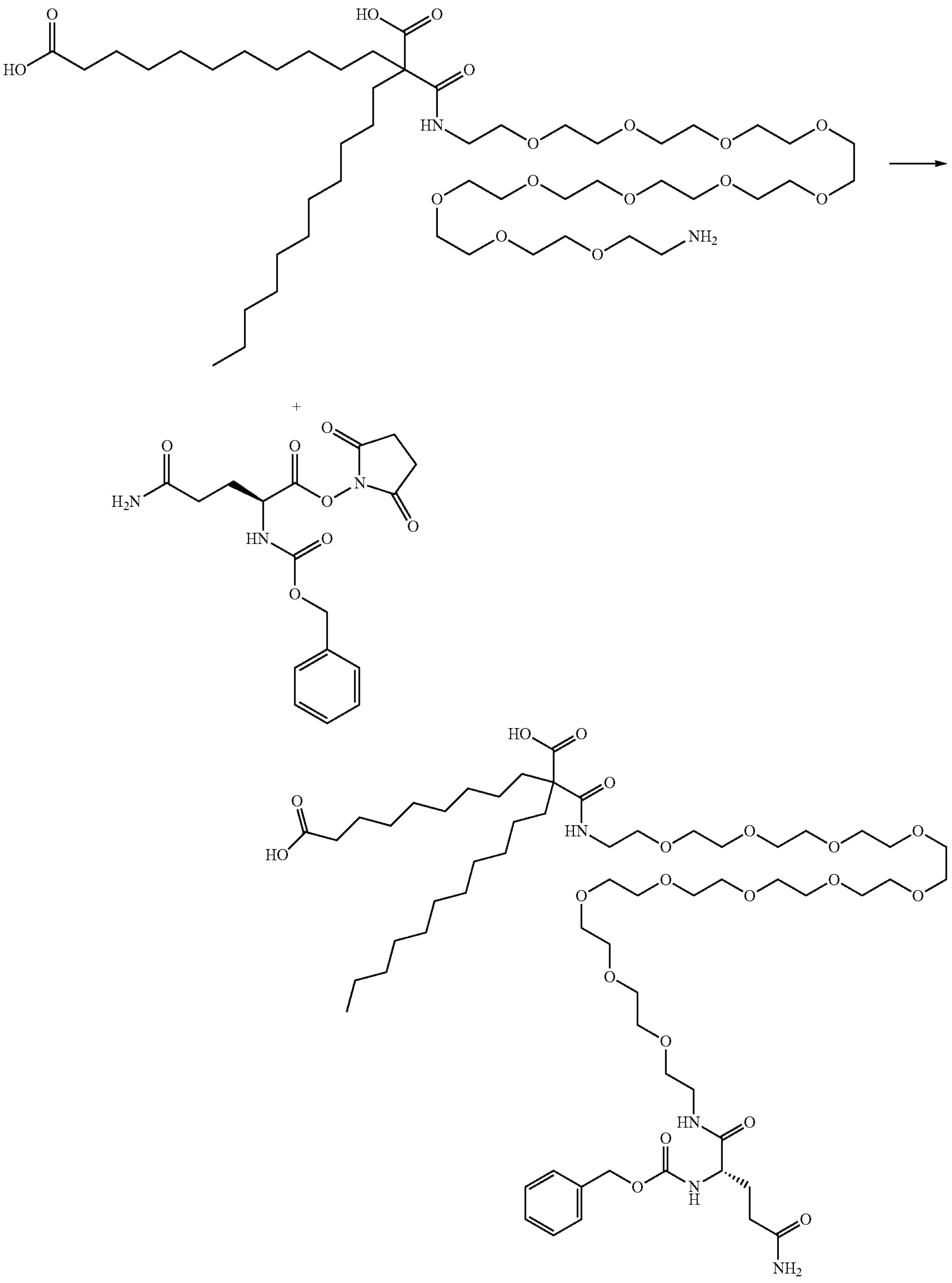

A solution of 2-((2,2-Dimethyl-4-oxo-3,8,11,14,17,20,23,26,29,32, 35,38-dodecaoxa-5-azatetracontan-40-yl)carbamoyl)-2-undecyltridecanedioic acid (20 mg, 0.018 mmol) in THF (Volume: 2 mL) was added to Z-L-Gln-Osu (Santa Cruz Biotechnology, CAS 34078-85-8, 11 mg, 0.029 mmol), then DIPEA (75 μl, 0.429 mmol) was added. Stirred at room temperature under a nitrogen atmosphere over weekend. Complete conversion was observed by LCMS (Acidic Eluent A: Water+0.05% Trifluoroacetic Acid, Eluent B: ACN, column Sunfire C18 3.5 μm 3.0×30 mm −40° C., 5-95% gradient 2 minutes, retention time 1.77 min) The reaction mixture was concentrated under reduced pressure and then dissolved in acetonitrile. Purified on a MS-triggered HPLC (Sunfire 30×50 mm Sum column ACN/H2O w/0.1% TFA 75 ml/min 1.5 ml injection, 55-80% ACN 3.5 min gradient, retention time 2.70 minutes) and the fractions pooled and lyophilized to give 10.5 mg clean product ZQ-FA in 46% yield as a clear colorless oil.

LCMS SQ4 RXNMON_Acidic Rt=1.60 min, M+H 1232.4; $^{1}$H NMR (400 MHz, ACETONITRILE-$d_3$) δ ppm 0.67-0.93 (m, 2 H) 0.93-1.10 (m, 2 H) 1.10-1.32 (m, 15 H) 1.45 (quin, J=7.24 Hz, 1 H) 1.59-1.69 (m, 1 H) 1.75-1.93 (m, 30 H) 1.94-2.21 (m, 20 H) 3.23 (quin, J=5.26 Hz, 1 H) 3.28-3.51 (m, 23 H) 3.95 (td, J=7.73, 5.44 Hz, 1 H) 4.92-5.22 (m, 1 H) 5.78 (br. s., 1 H) 6.13-6.42 (m, 1 H) 6.88 (br. s., 1 H) 7.20-7.36 (m, 2 H) 7.42 (t, J=5.07 Hz, 1 H).

Azido-nitrophenyl-glutamine-glycine

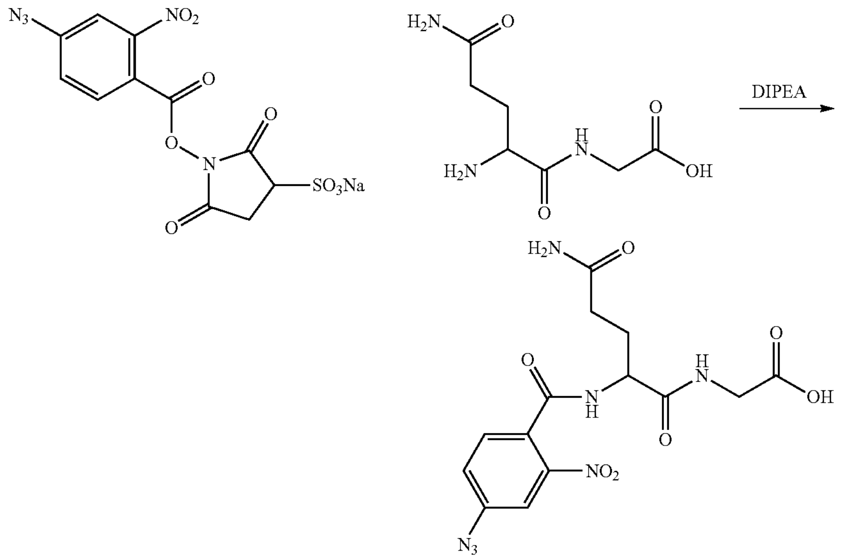

QG (30 mg, 0.148 mmol) was dissolved in DMF (Volume: 1 mL, Ratio: 1.000) and sodium 1-((4-azido-2-nitrobenzoyl) oxy)-2,5-dioxopyrrolidine-3-sulfonate (60.1 mg, 0.148 mmol) was added in $H_2O$ (Volume: 1.000 mL, Ratio: 1.000) followed by addition of DIPEA (0.177 mmol). The reaction stirred for 16 hours at which time the product was purified by HPLC (Sunfire 30×50 mm 5 um column ACN/H2O w/0.1% TFA 75 ml/min 1.5 ml injection, rt=1.53) to give the desired product in 62% yield. LCMS SQ4 RXNMON_Acidic Rt=0.68 min, M+H 394.3; $^{1}$H NMR (400 MHz, methanol-$d_4$) δ ppm 1H NMR (METHANOL-d4, 400 MHz): 8.12-8.26 (m, 1H), 7.21-7.40 (m, 2H), 4.60 (dd, J=8.3, 5.7 Hz, 1H), 3.83-4.15 (m, 2H), 2.36-2.54 (m, 2H), 2.21 (d, J=7.5 Hz, 1H), 2.07 (d, J=6.6 Hz, 1H).

Diazirine-QG

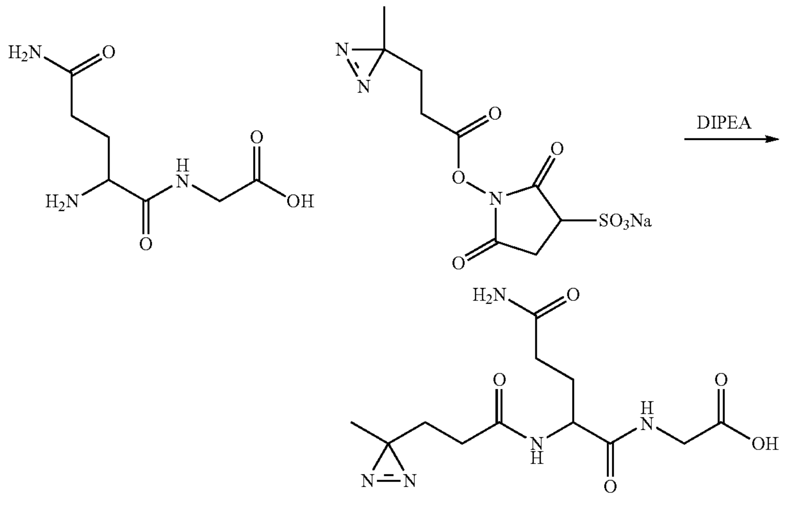

QG (30 mg, 0.148 mmol) was dissolved in DMF (Volume: 1 mL, Ratio: 1.000) and sodium 1-((3-(3-methyl-3H-diazirin-3-yl)propanoyl)oxy)-2,5-dioxopyrrolidine-3-sulfonate (50 mg, 0.153 mmol) in $H_2O$ (Volume: 1.000 mL, Ratio: 1.000) was added followed by DIPEA (0.031 mL, 0.177 mmol). Reaction stirred 16 hours at which time product was directly purified by HPLC (Sunfire 30×50 mm Sum column 15-20% gradient ACN/H2O w/0.1% TFA 75 ml/min 1.5 ml injection, rt=2.46) to give the desired product in 52% yield. LCMS SQ4 RXNMON_Acidic Rt=0.61 min, M+H 314.2; $^{1}$H NMR (400 MHz, methanol-$d_4$) δ ppm 1H NMR (METHANOL-d4, 400 MHz): 4.39 (dd, J=8.3, 5.7 Hz, 1H), 3.76-4.04 (m, 2H), 2.34 (m, 2H), 2.11-2.19 (m, 2H), 2.07-2.11 (m, 1H), 1.89-2.00 (m, 1H), 1.62-1.74 ppm (m, 2H), 1.01 (s, 3H).

ZQ$(PEG)_3$ Biotin

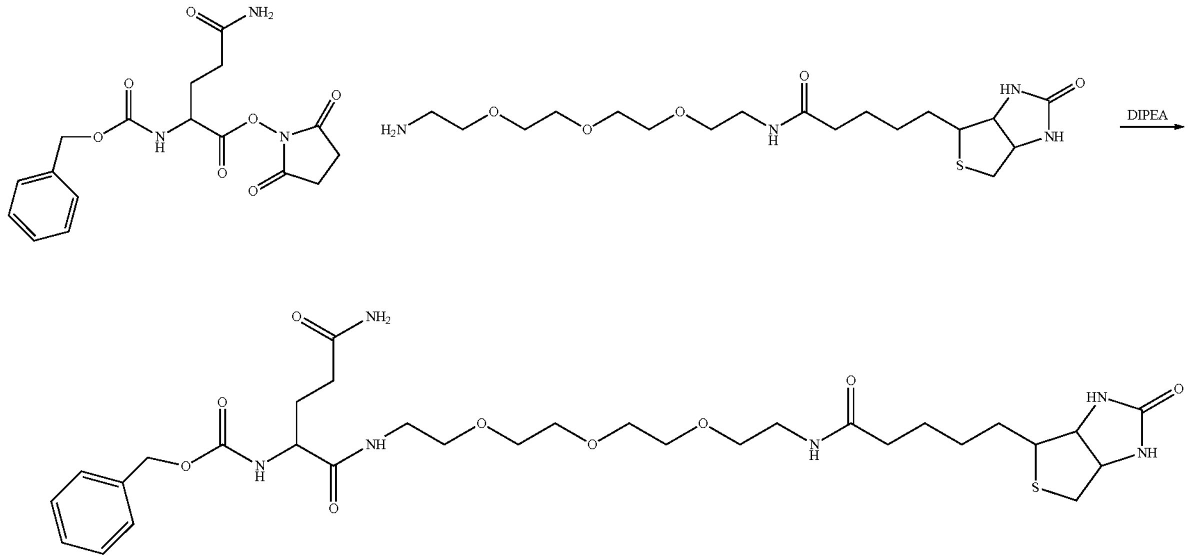

ZQ NHS (45.1 mg, 0.119 mmol), biotin amine (Pierce cat #21347, 50 mg, 0.119 mmol), and DIPEA (23 uL, 0.131 mmol) were combined in DMF (2 mL) and stirred at room temp for 2 hours at which time LCMS shows predominantly product. Reaction loaded on HPLC (Sunfire 30×50 mm Sum column 15-20% gradient ACN/H2O w/0.1% TFA 75 ml/min 1.5 ml injection, rt=2.46) to give the desired product in 43% yield. LCMS SQ4 RXNMON_Acidic Rt=0.79 min, M+H 681.4; 1H NMR (METHANOL-d4, 400 MHz): d=7.33-7.41 (m, 4H), 7.27-7.33 (m, 1H), 5.08 (s, 2H), 4.48 (dd, J=7.8, 4.4 Hz, 1H), 4.29 (dd, J=7.9, 4.5 Hz, 1H), 4.12 (m, 1H), 3.57-3.67 (m, 8H), 3.49-3.57 (m, 4H), 3.34-3.43 (m, 4H), 3.15-3.23 (m, 1H), 2.92 (dd, J=12.8, 5.1 Hz, 1H), 2.70 (d, J=12.8 Hz, 1H), 2.26-2.36 (m, 2H), 2.21 (t, J=7.4 Hz, 2H), 2.04 (m, 1H), 1.92 (m, 1H), 1.53-1.77 (m, 4H), 1.44 ppm (m, 2H).

Conjugation of Modifying Compounds to $CRM_{197}$

Z-Q-G-NH-$(PEG)_3$-$N_3$

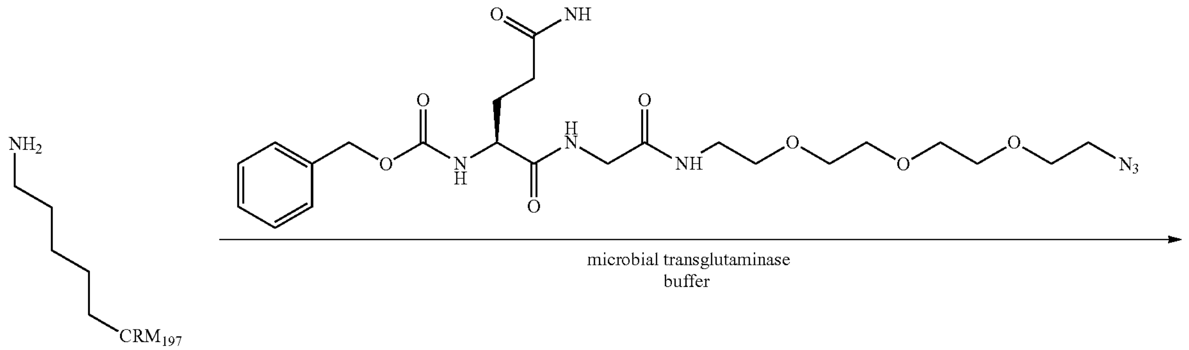

-continued

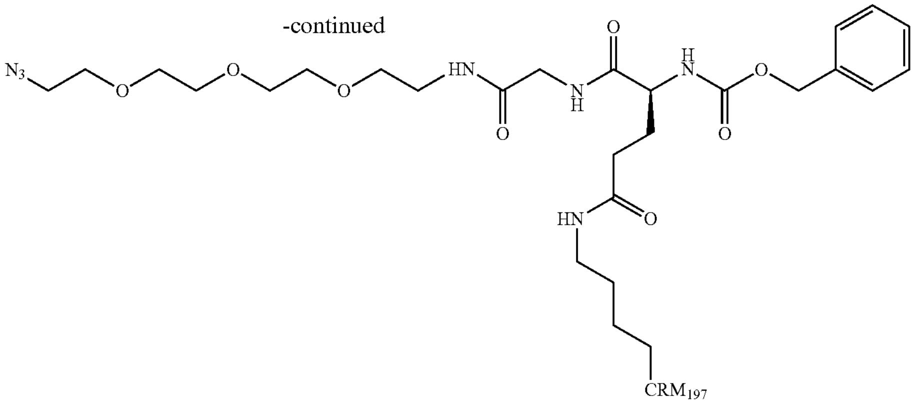

32 μL of CRM197 (32 mg/mL) is added to 1000 μL of Z-Q-G-NH-$(PEG)_3$-$N_3$ (2 mg/mL) in 100 mM pH 8 Tris buffer and 100 μL of microbial transglutaminase (stock of 50 mg/mL in PBS 1× prepared from commercial 1% mTGase in maltocyclodextrin) are added. Reaction incubated at 25° C. for 30 minutes. Reaction purified via SEC with a running buffer of PBS 1× over 1.5 CV. One addition of the linker is observed by Mass Spectrum. LCMS calculated: 58929; observed: (M+1) 58930. Yield: 700 ug, 68% yield.

32 μL of CRM197 (32 mg/mL) is added to 1000 μL of Z-Q-G-NH-$(PEG)_3$-$N_3$ (2 mg/mL) in 100 mM pH 8 Tris buffer and 100 μL of microbial transglutaminase (stock of 50 mg/mL in PBS 1× prepared from commercial 1% mTGase in maltocyclodextrin) are added. Reaction incubated at 25° C. for 18 hours. Reaction purified via SEC with a running buffer of PBS 1× over 1.5 CV. Two additions of the linker are observed by Mass Spectrum. LCMS calculated: 59450; observed: (M+1) 59451. Yield: 700 ug, 68% yield.

32 uL of CRM197 (32 mg/mL) is added to 1000 μL, of Z-Q-G-NH-$(PEG)_3$-$N_3$ (2 mg/mL) in 100 mM pH 6 Sodium acetate buffer and 100 uL of microbial transglutaminase (stock of 50 mg/mL in PBS 1× prepared from commercial 1% mTGase in maltodextrin) is added. Reaction incubated at 25° C. for 3 days. Reaction purified via SEC with a running buffer of PBS 1× over 1.5 CV. Three and four additions are observed by Mass Spectrum. LCMS calculated: 59971, 60492; observed: (M+1) 59972, 60493. Yield: 700 ug, 68% yield.

ZQ-NH-$(PEG)_3N_3$

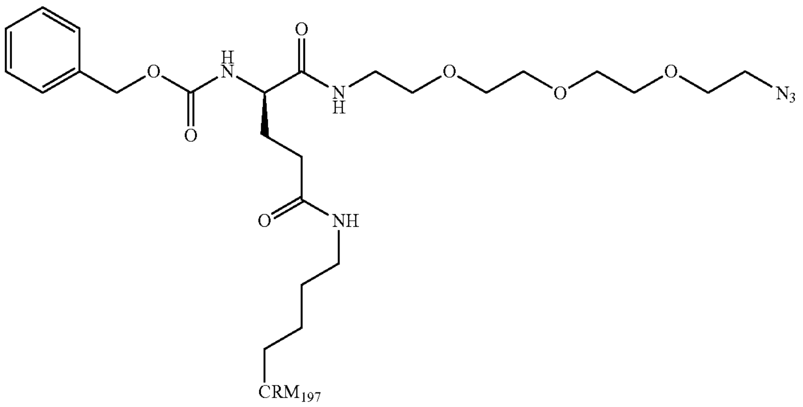

63 μL of CRM197 (32 mg/mL) is added to 1800 μL of ZQ-NH-$(PEG)_3N_3$ (2 mg/mL) in 100 mM pH 8 Tris buffer and 150 uL of microbial transglutaminase (stock of 50 mg/mL in PBS 1× prepared from commercial 1% mTGase in maltocyclodextrin) are added. Reaction incubated at 25° C. for 1 hour. Reaction purified via SEC with a running buffer of PBS 1× over 1.5 CV. One addition of the linker is observed by Mass Spectrum. LCMS calculated: 58872; observed: (M+1) 58875. Yield: 1.3 mg (67%).

Cyclooctyne-cyclopropyl-$CH_2$—OC(O)NH-Q-G

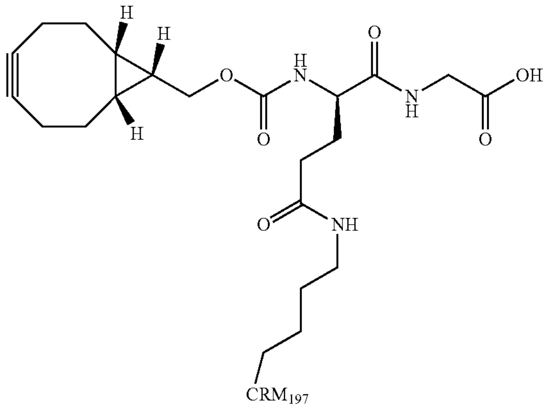

32 μL of CRM197 (32 mg/mL) is added to 1000 μL, of Cyclooctyne-cyclopropyl-$CH_2$—OC(O)NH-Q-G (2 mg/mL)

in 100 mM pH 8 Tris buffer and 100 μL of microbial transglutaminase (stock of 50 mg/mL in PBS 1× prepared from commercial 1% mTGase in maltocyclodextrin) are added. Reaction incubated at 25° C. for 3 hours. Reaction purified via SEC with a running buffer of PBS 1× over 1.5 CV One addition of the linker is observed by Mass Spectrum. LCMS calculated: 58771 observed: (M+1) 58771. Yield: 0.475 mg, 50% yield.

Cyclooctyne-cyclopropyl-$CH_2$—OC(O)NH-L-Q-G

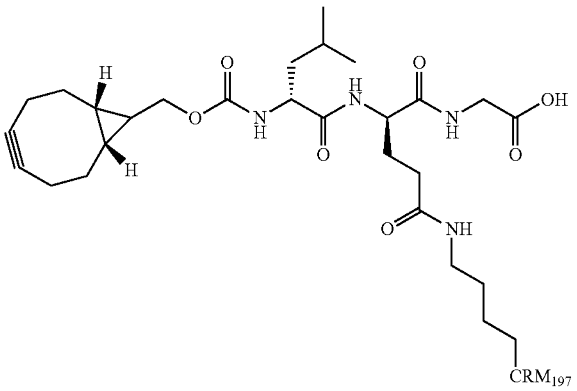

1 μL of CRM197 (32 mg/mL) is added to 30 μL of Cyclooctyne-cyclopropyl-$CH_2$—OC(O)NH-L-Q-G (2 mg/mL) in 100 mM pH 8 Tris buffer and 3 μL of microbial transglutaminase (stock of 50 mg/mL in PBS 1× prepared from commercial 1% mTGase in maltocyclodextrin) are added. Reaction incubated at 25° C. for 1 hour. One addition of the linker is observed by Mass Spectrum. LCMS calculated: 58884 observed: (M+1) 58885.

1 μL of CRM197 (32 mg/mL) is added to 30 μL, of Cyclooctyne-cyclopropyl-$CH_2$—OC(O)NH-L-Q-G (2 mg/mL) in 100 mM pH 8 Tris buffer and 3 μL of microbial transglutaminase (stock of 50 mg/mL in PBS 1× prepared from commercial 1% mTGase in maltocyclodextrin) are added. Reaction incubated at 25° C. for 24 hours. Two additions of the linker are observed by Mass Spectrum. LCMS calculated: 59360 observed: (M+1) 59361.

Z-Q-NH—$(CH_2)_3$-dimethylacetal

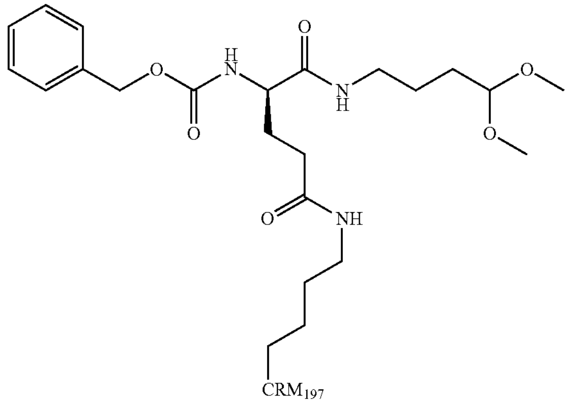

1 μL of CRM197 (32 mg/mL) is added to 50 μL of Z-Q-NH—$(CH_2)_3$-dimethylacetal (8 mg/mL) in 100 mM pH 8 Tris buffer and 3 uL of microbial transglutaminase (stock of 50 mg/mL in PBS 1× prepared from commercial 1% mTGase in maltocyclodextrin) are added. Reaction incubated at 22° C. for 1 hour. One addition of the linker is observed by Mass Spectrum. LCMS calculated: 58787; observed: (M+1) 58788.

Z-Q-NH—$(CH_2)_2$—NH—C(O)—$CH_2$-Alexafluor647

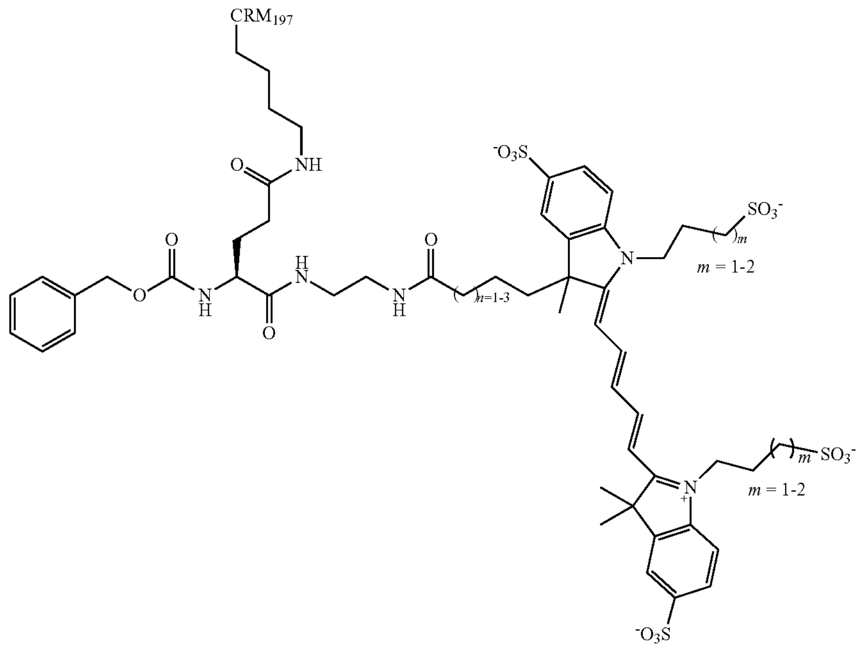

100 μL of CRM197 (32 mg/mL) is added to 3000 μL of Z-Q-NH—$(CH_2)_2$—NH—C(O)—$CH_2$-Alexafluor647 (1 mg/mL) in 100 mM pH 8 Tris buffer and 300 uL of microbial transglutaminase (stock of 50 mg/mL in PBS 1× prepared from commercial 1% mTGase in maltocyclodextrin) are added. Reaction incubated at 25° C. for 18 hours. Reaction purified via SEC with a running buffer of PBS 1× over 1.5 CV. One addition of the Fluorophore is observed by Mass Spectrum. LCMS calculated: 59554; observed: (M+1) 59556 Yield: 2.6 mg, 81% yield.

Ac-L-Q-G-NH—$(CH_2)_2$—C(O)—$(CH_2)_2$—$SO_2$-Tol

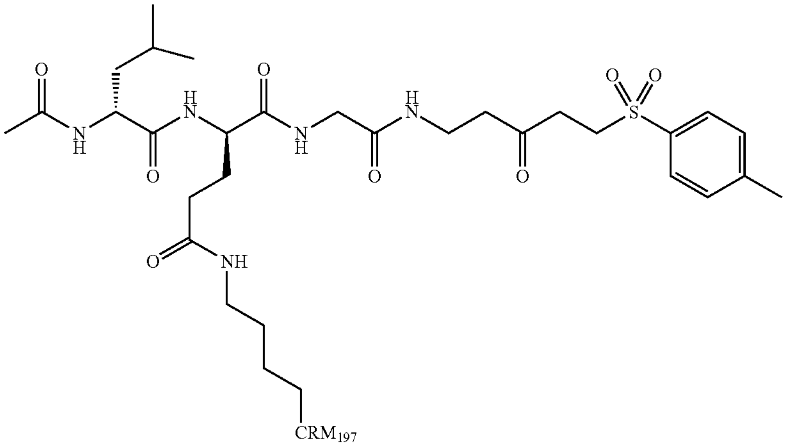

To a solution of Ac-L-Q-G-NH—$(CH_2)_2$—C(O)—$(CH_2)_2$—$SO_2$-Tol (50 μL, 0.084 μmol) (roughly 1 mg/mL) was added CRM (0.5 μL, 0.00027 μmol) and TGase (1.5 μL, 1.97E-05 μmol) and mixed at 25° C. for 1 hr. Reaction ~60% complete. LCMS calculated: 58987 observed: (M+1) 58988. Reaction taken directly onto further modification with glutathione (procedure below).

Z-Q-NH—$(CH_2)_4$—C(O)—$(CH_2)_2$—$SO_2$-Tol

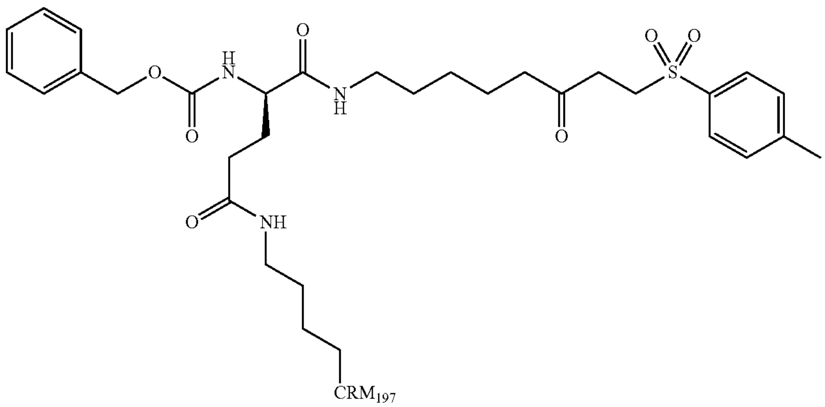

1 μL of CRM197 (32 mg/mL) is added to 30 μL of Z-Q-NH—$(CH_2)_4$—C(O)—$(CH_2)_2$—$SO_2$-Tol (1 mg/mL) in 100 mM pH 6 Sodium Acetate buffer and 3 μL of microbial transglutaminase (stock of 50 mg/mL in PBS 1× prepared from commercial 1% mTGase in maltocyclodextrin) are added. Reaction is incubated at 25° C. for 3 hours. Reaction is purified via a 10 kDa Amicon filter. One addition of the linker was observed by Mass Spec. LCMS calculated: 58951 observed: (M+1) 58953.

Z-Q-NH-MenA Polysaccharide

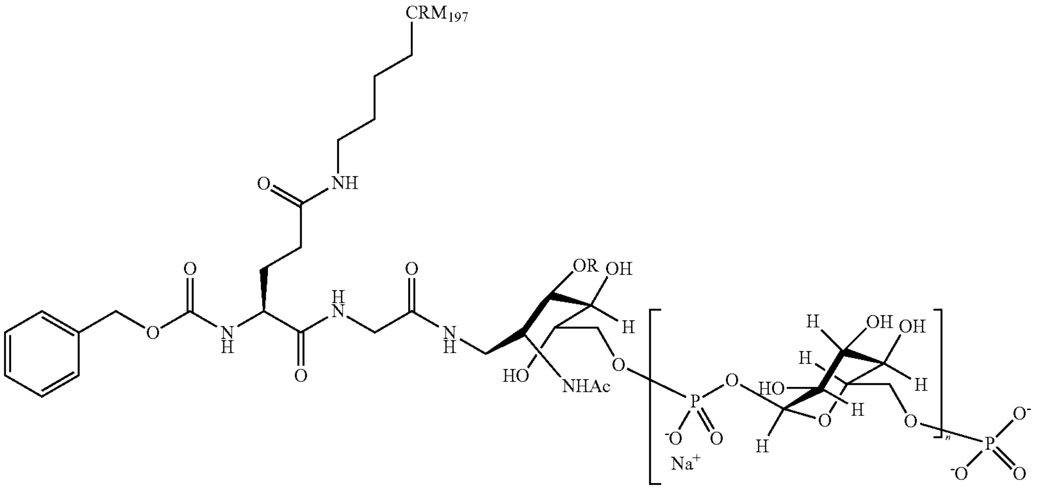

$n$ = 15-20

156 μL of CRM197 (32 mg/mL) is added to 5000 μL of Z-Q-NH-MenA Polysaccharide (1 mg/mL) in 100 mM pH 8 Tris buffer and 488 μL of microbial transglutaminase (stock of 50 mg/mL in PBS 1× prepared from commercial 1% mTGase in maltocyclodextrin) are added. Reaction incubated at 25° C. for 18 hours. Reaction purified via 50 kDa Amicon filter which resulted in a final yield of 2 mg of product (38% yield). Product was confirmed by SDS page (in above drawings paragraph 006) as the product is a hetergeneous mixture due to the heterogenity of the polysaccharide.

Z-Q-NH—$(CH_2)_5$—C(O)-monomethylauristatin F

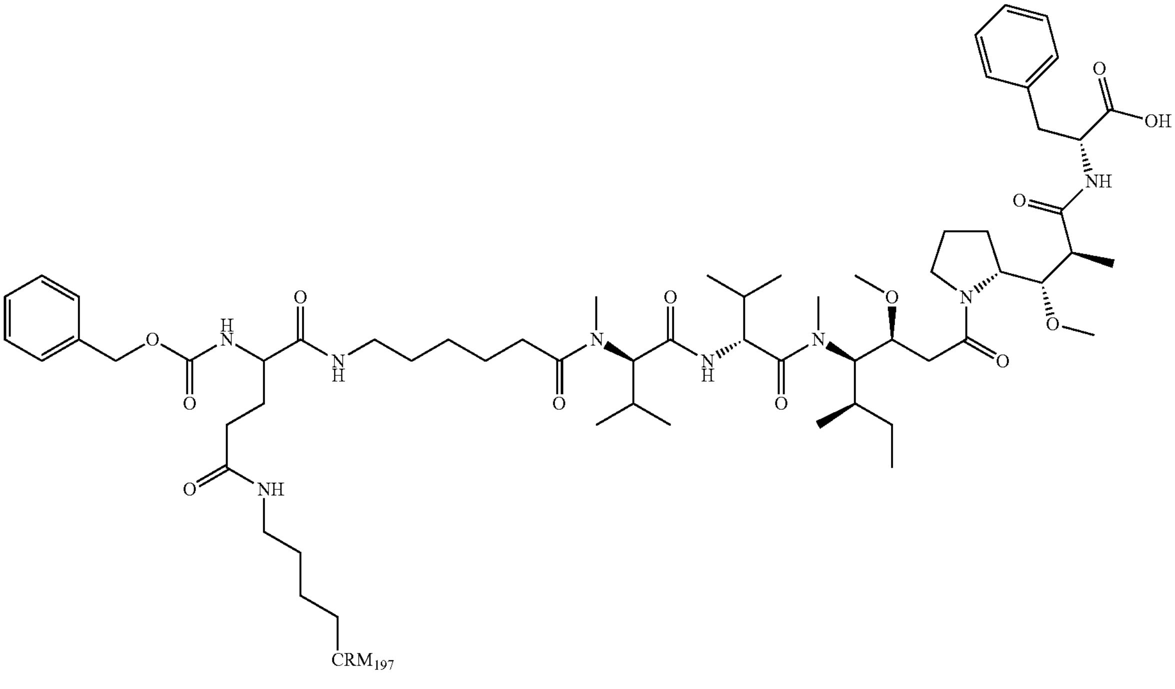

50 μL of CRM197 (32 mg/mL) is added to 1500 μL of Z-Q-NH—$(CH_2)_5$—C(O)-monomethylauristatin F (1 mg/mL) in 100 mM pH 8 Tris buffer and 150 μL of microbial transglutaminase (stock of 50 mg/mL in PBS 1× prepared from commercial 1% mTGase in maltocyclodextrin) are added. Reaction incubated at 25° C. for 45 minutes. Reaction purified via SEC with a running buffer of PBS 1× over 1.5 CV. One addition of MMAF is observed on the Mass Spec. LCMS calculated: 59499 observed: 59498 Yield: 659 ug, 38% yield.

60 μL of CRM197 (32 mg/mL) is added to 1500 μL of Z-Q-NH—$(CH_2)_5$—C(O)-monomethylauristatin F (1 mg/mL) in 100 mM pH 8 Tris buffer and 170 μL of microbial transglutaminase (stock of 50 mg/mL in PBS 1× prepared from commercial 1% mTGase in maltocyclodextrin) are added. Reaction incubated at 25° C. for 24 hours. An additional 60 μL of mTGase was added, and the reaction was incubated for another 18 hours. Reaction purified via SEC with a running buffer of PBS 1× over 1.5 CV. Two additions of MMAF are observed by the Mass Spectrum. LCMS calculated: 60590 observed: 60589 Yield: 700 ug, 36% yield.

Phenol-(CH2)2-C(O)-L-Q-G

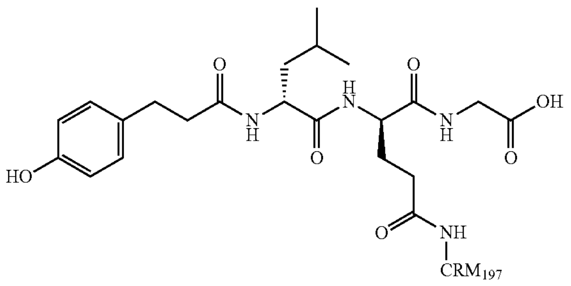

1 μL, of CRM197 (32 mg/mL) is added to 22 μL of Phenol-(CH2)2-C(O)-L-Q-G (0.5 mg/mL) in 100 mM pH 8 Tris buffer and 3 μL of microbial transglutaminase (stock of 50 mg/mL in PBS 1× prepared from commercial 1% mTGase in maltocyclodextrin) are added. Reaction incubated at 25° C. for 1 hour. The addition of one small molecule is observed by Mass Spec. Expected Mass: 58856. Observed Mass: 58857.

Modification of GBS80 with Z-Q-G-NH-$(PEG)_3$-$N_3$

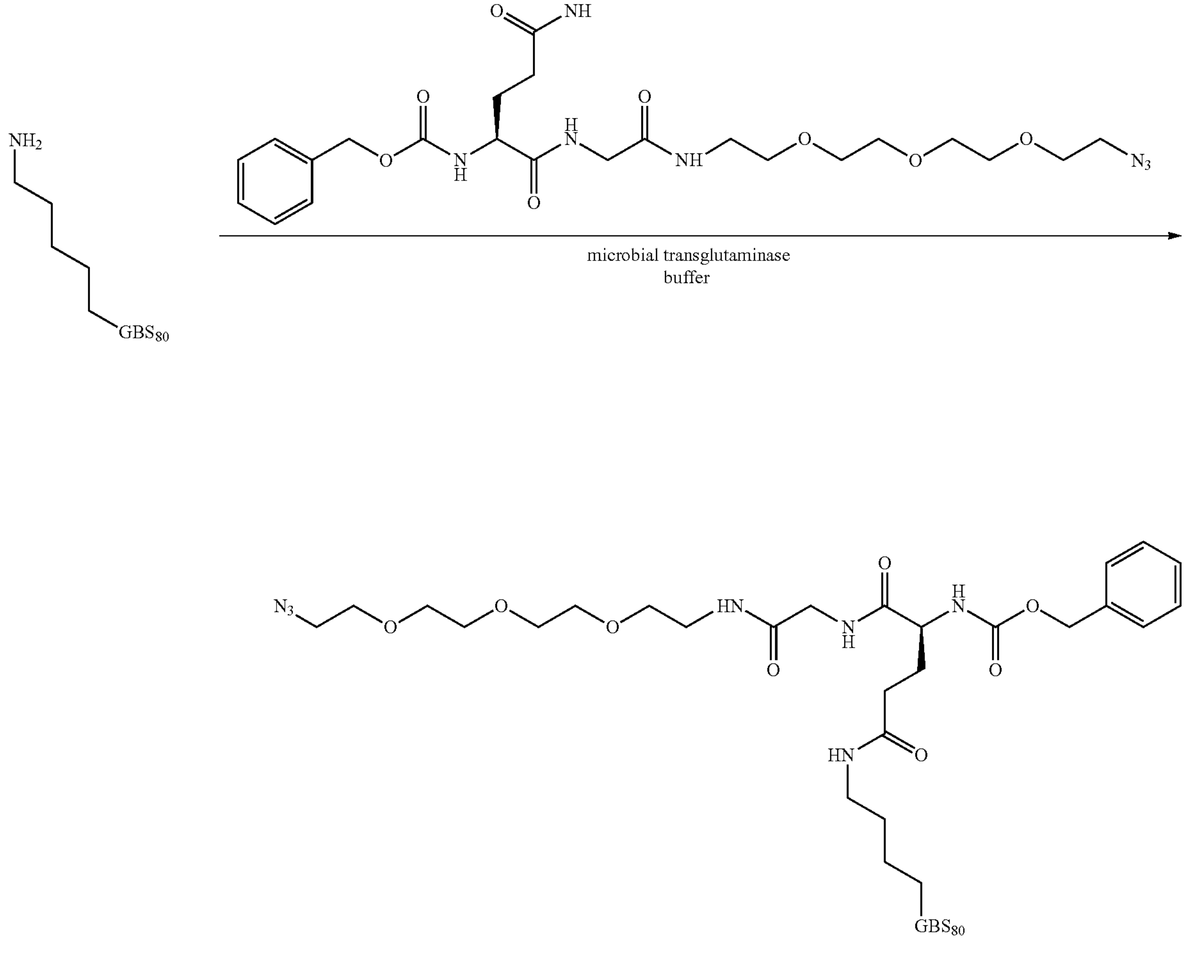

2.32 mL GBS80 protein (3.49 mg/mL) was added to 14 mL Z-Q-G-NH-$(PEG)_3$-$N_3$ (8 mg/mL) in 100 mM sod acetate pH 6 and 50 μL of mTGase (50 mg/ml in PBS) was added. Reaction was incubated overnight at 37° C. LCMS shows addition of 1 and 2 adducts and a small amount of +3. Reaction was quenched with 0.8 mL 3-(2,5-dioxo-2,5-dihydro-1H-pyrrol-1-yl)propanoic acid (10 mg/mL) and incubated at rt for 1 hr. Reaction was then passed through zeba spin column 3×. Recovered material was analyzed by LCMS giving modified GBS80 in 78% overall yield. LCMS calculated: 53355, 53880, 54405; observed: (M+1) 53355, 53877, 54398.

mTGase-Mediated Labelling of CRM197+ZQ(PEG2)Azidobenzylamide

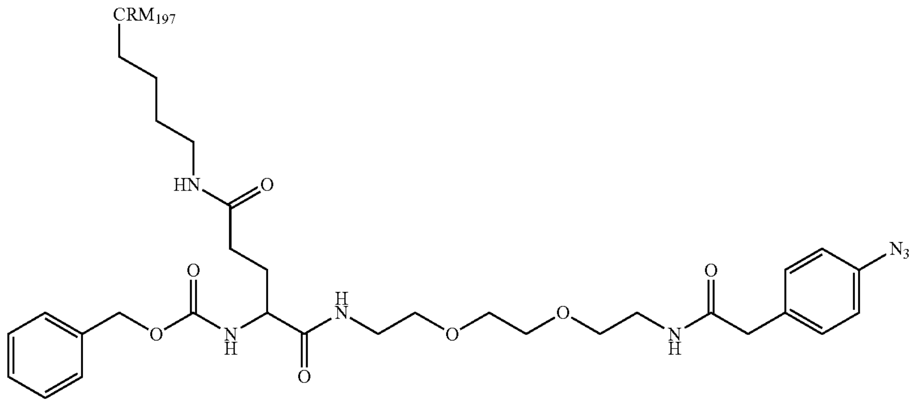

To a solution of ZQ(PEG2)azidobenzylamide (benzyl (17-amino-1-(4-azidophenyl)-2,13,17-trioxo-6,9-dioxa-3,12-diazaheptadecan-14-yl)carbamates) in tris buffer pH 8 (3.5 mg/mL, 86 μL, 0.527 μmol) was added CRM197 (33 mg/mL, 7.55 μL, 0.0043 μmol) followed by a solution of transglutaminase enzyme in PBS (50 mg/mL, 7.61 μL, 0.0100 μmol). The reaction was stirred at 37° C. for 16 hours at which point LCMS analysis showed conversion to +1, +2 and +3 products. LCMS QT2; Protein_35-70 kDa_3 min: $R_t$=1.48 min; MS [M+linker]: observed: 58958, calculated: 58962; MS [M+(2 linkers)]: observed: 59513, calculated: 59514; MS [M+(3 linkers)]: observed: 60067, calculated: 60066.

| Degree of Labelling | Calculated | Observed | % | $R_t$ (min) |
|---|---|---|---|---|
| CRM197 | 58410 | 58408 | 19 | 1.48 |
| CRM197 + 1 ZQ-linker | 58962 | 58958 | 36 | 1.48 |
| CRM197 + 2 ZQ-linker | 59514 | 59513 | 25 | 1.48 |
| CRM197 + 3 ZQ-linker | 60066 | 60067 | 20 | 1.48 |

mTGase-mediated labelling of CRM197+ZQ$(PEG)_2$ amidoethylmethyldiazirin

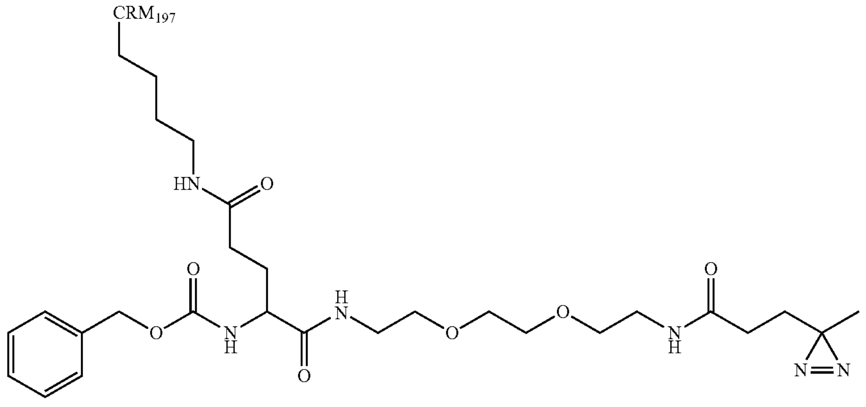

To a solution of benzyl (18-amino-1-(3-methyl-3H-diazirin-3-yl)-3,14,18-trioxo-7,10-dioxa-4,13-diazaoctadecan-15-yl)carbamate in tris buffer pH 8 (3.5 mg/mL, 50 μL, 0.336 μmol) was added CRM197 (33 mg/mL, 4.82 μL, 0.0027 μmol) followed by a solution of transglutaminase enzyme in PBS (50 mg/mL, 4.85 μL, 0.0064 μmol). The reaction was stirred at r.t. for two days at which point LCMS analysis showed conversion to +1, +2 and +3 product. LCMS QT2; Protein_35-70 kDa_3 min: $R_t$=1.69 min; MS [M+linker]: observed: 58912, calculated: 58913; MS [M+(2× linker)]: observed: 59415, calculated: 59416; MS [M+(3× linker)]: observed: 59918, calculated: 59919.

| Degree of Labelling | Calculated | Observed | % | $R_t$ (min) |
|---|---|---|---|---|
| CRM197 | 58410 | 58408 | 11 | 1.69 |
| CRM197 + 1 ZQ-linker | 58913 | 58912 | 45 | 1.69 |
| CRM197 + 2 ZQ-linker | 59416 | 59415 | 32 | 1.69 |
| CRM197 + 3 ZQ-linker | 59919 | 59918 | 12 | 1.69 |

mTGase-mediated labelling of CRM197+ZQ-FA

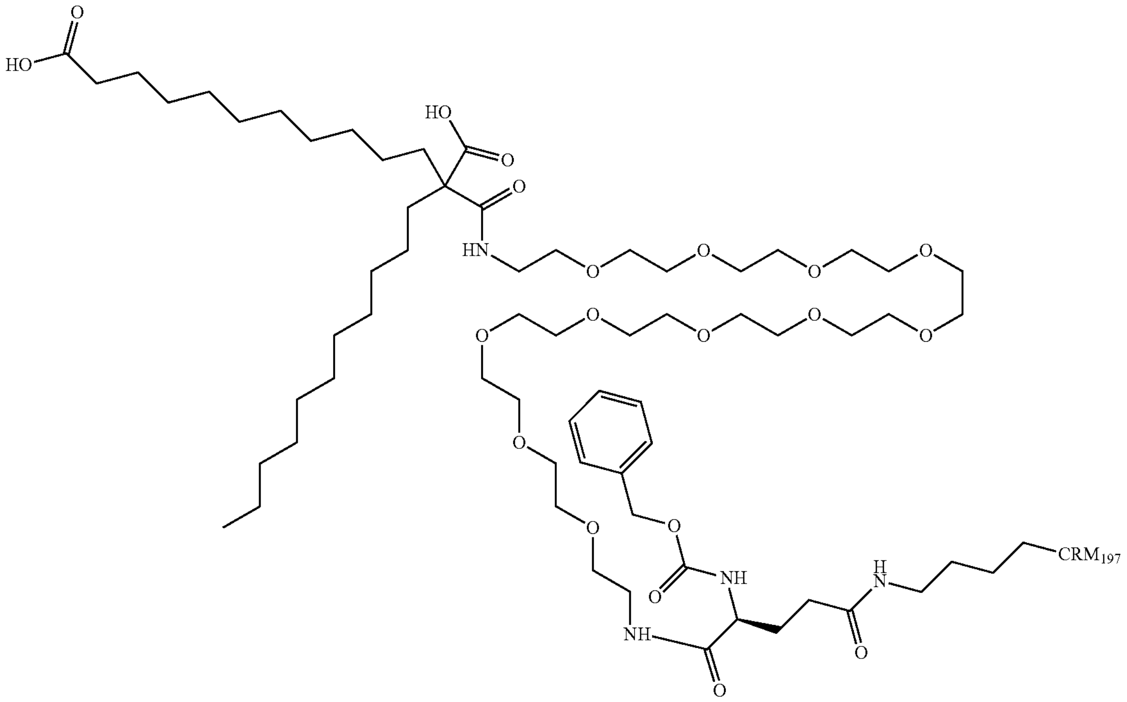

To a solution of ZQ-FA in 100 mM tris buffer pH 8 (8 mg/mL, 203 μL, 1.316 μmol) was added CRM197 (33 mg/mL, 1.515 μL, 0.00086 μmol) followed by a solution of transglutaminase enzyme in PBS (50 mg/mL, 0.455 μL, 0.00060 μmol). The reaction was stirred at r.t. for 16 hours. The reaction mixture was exchanged into 100 mM tris buffer pH 8 using 10 kDa MWCO Amicon centrifugal filter by diluting and concentrating the reaction 5 times to a volume of 100 pt. LCMS analysis showed conversion to +1, +2, +3 and +4 products. LCMS QT2; Protein_35-70 kDa_3 min: $R_t$=1.45 min; MS [M+ZQ-FA]: observed: 59625, calculated: 59624; MS [M+(2×ZQ-FA)]: observed: 60839, calculated: 60838; MS [M+(3×ZQ-FA)]: observed: 62054, calculated: 62052; MS [M+(4×ZQ-FA)]: observed: 63270, calculated: 63266.

| Degree of Labelling | Calculated | Observed | % | $R_t$ (min) |
|---|---|---|---|---|
| CRM197 | 58410 | n/a | 0 | n/a |
| CRM197 + 1 ZQ-FA | 59624 | 59625 | 14 | 1.45 |
| CRM197 + 2 ZQ-FA | 60838 | 60839 | 23 | 1.45 |
| CRM197 + 3 ZQ-FA | 62052 | 62054 | 35 | 1.45 |
| CRM197 + 4 ZQ-FA | 63266 | 63270 | 28 | 1.45 |

mTGase-Mediated Labelling of CRM197+ Azido Nitrophenyl QG

To a solution of azidonitrophenyl-QG in 100 mM tris buffer pH 8 (8 mg/mL, 100 μL) was added CRM197 (33 mg/mL, 1.0 μL, 33 ug) followed by a solution of transglutaminase enzyme in PBS (50 mg/mL, 1.0 μL, 0.1% TGase in maltocyclodextrin). The reaction was incubated at r.t. for 16 hours. LCMS analysis showed conversion to +1, +2, and +3 product. LCMS QT1; Protein_20-70 kDa_3 min: $R_t$=1.67 min; MS [M+1 azido nitrophenyl QG]: observed: 58815, calculated: 58803; MS [M+2 azido nitrophenyl QG]: observed: 59191, calculated: 59196; MS [M+3 azido nitrophenyl QG]: observed: 59585, calculated: 59589.

| Degree of Labelling | Calculated | Observed | % | $R_t$ (min) |
|---|---|---|---|---|
| CRM197 | 58410 | 58428 | 5 | n/a |
| CRM197 + 1 azidonitrophenylQG | 58803 | 58815 | 50 | 1.67 |
| CRM197 + 2 azidonitrophenylQG | 59196 | 59191 | 40 | 1.67 |
| CRM197 + 3 azidonitrophenylQG | 59589 | 59585 | 5 | 1.67 |

mTGase-Mediated Labelling of CRM197+ Diazirine-QG

To a solution of diazirine-QG in 100 mM tris buffer pH 8 (8 mg/mL, 100 μL) was added CRM197 (33 mg/mL, 1.0 μL, 33 ug) followed by a solution of transglutaminase enzyme in PBS (50 mg/mL, 1.0 μL, 0.1% TGase in maltocyclodextrin). The reaction was incubated at r.t. for 2 hours. LCMS analysis showed conversion to +1 product. LCMS QT1; Protein_20-

70 kDa_3 min: $R_t$=1.67 min; MS [M+diazirine-QG]: observed: 58705, calculated: 59706.

| Degree of Labelling | Calculated | Observed | % | $R_t$ (min) |
|---|---|---|---|---|
| CRM197 | 58410 | n/a | 0 | n/a |
| CRM197 + 1 diazirine-QG | 58706 | 58705 | 100 | 1.67 |

mTGase-Mediated Labelling of CRM197+ZQ(PEG)$_3$Biotin

To a solution of ZQ(PEG)$_3$Biotin in 100 mM tris buffer pH 8 (8 mg/mL, 100 μL) was added CRM197 (33 mg/mL, 1.0 μL, 33 ug) followed by a solution of transglutaminase enzyme in PBS (50 mg/mL, 1.0 μL, 0.1% TGase in maltocyclodextrin). The reaction was incubated at r.t. for 16 hours. LCMS analysis showed conversion to +1 product. LCMS QT1; Protein_20-70 kDa_3 min: $R_t$=1.67 min; MS [M+1 ZQ(PEG)$_3$ Biotin]: observed: 59073, calculated: 59074; MS [M+2 ZQ(PEG)$_3$Biotin]: observed: 59737, calculated: 59738; MS [M+3 ZQ(PEG)$_3$Biotin]: observed: 60403, calculated: 60402.

| Degree of Labelling | Calculated | Observed | % | $R_t$ (min) |
|---|---|---|---|---|
| CRM197 | 58410 | none | 0 | n/a |
| CRM197 + 1 ZQ(PEG)$_3$Biotin | 59074 | 59073 | 40 | 1.75 |
| CRM197 + 2 ZQ(PEG)$_3$Biotin | 59738 | 59737 | 55 | 1.75 |
| CRM197 + 3 ZQ(PEG)$_3$Biotin | 60402 | 60403 | 5 | 1.75 |

Examples of Functionalization of Labeled mTGase Catalyzed Selective Lysine Labeling of Proteins

Z-Q-G-NH-(PEG)$_3$-$N_3$

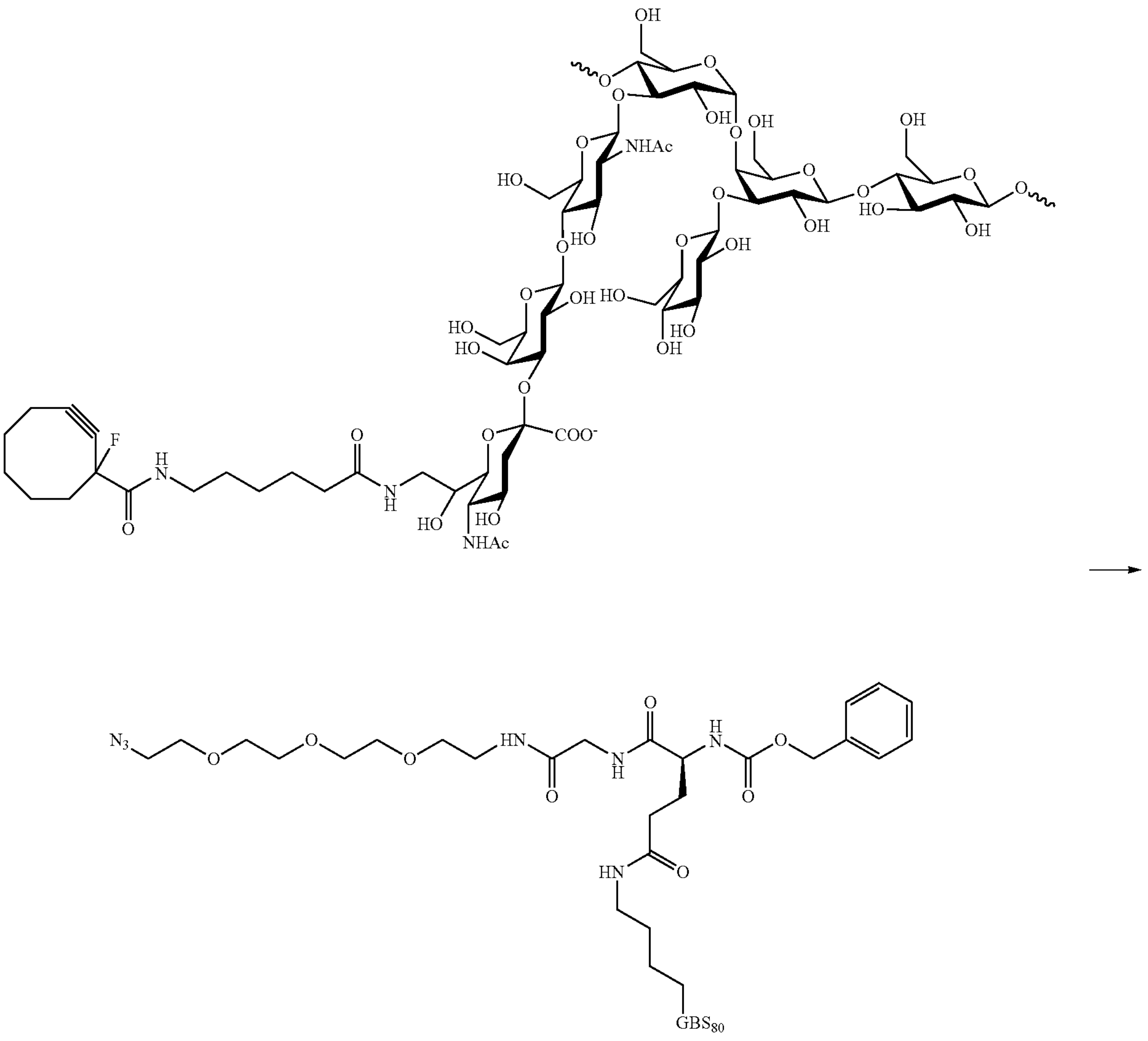

-continued
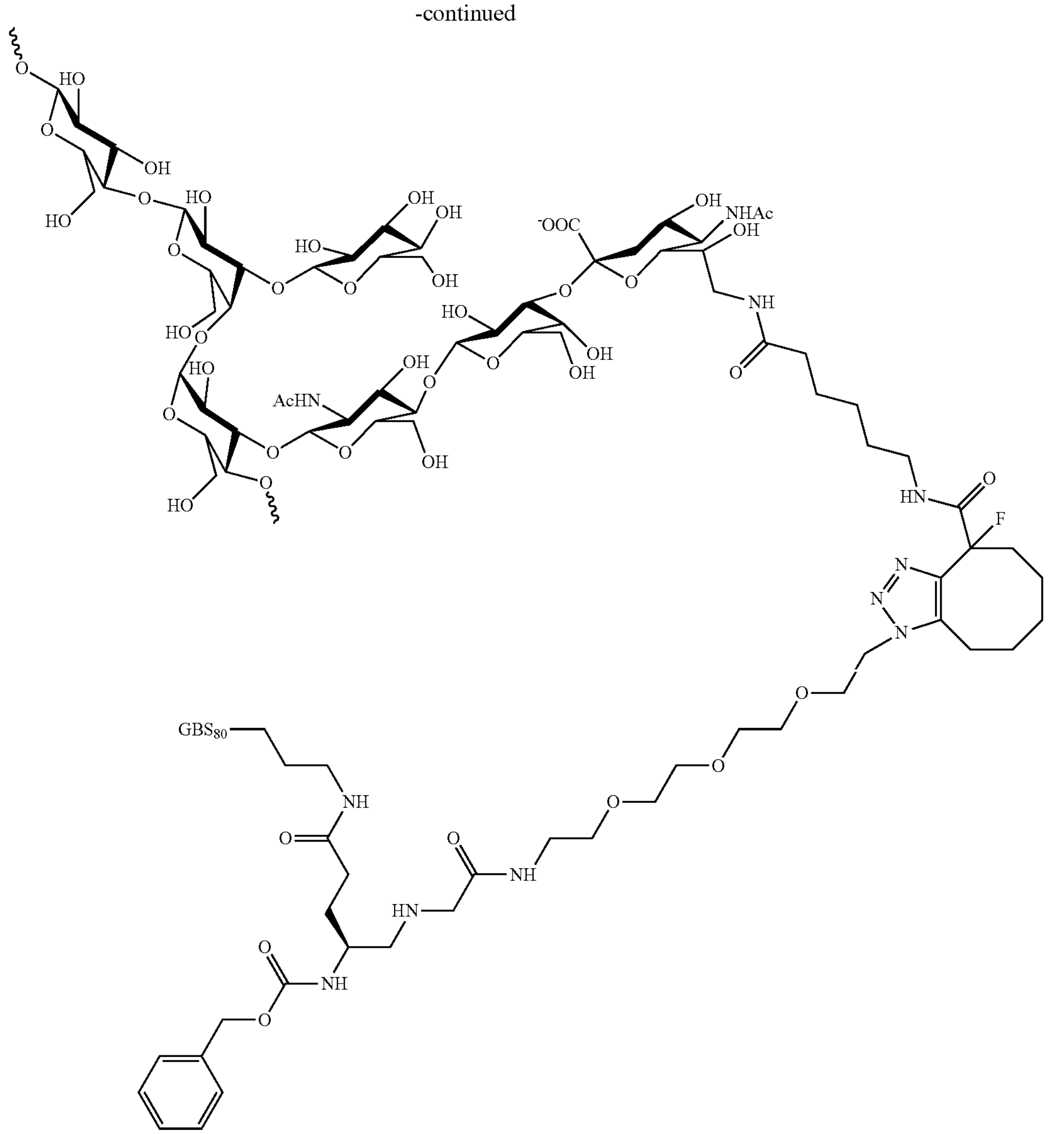
3.2 mg of azido labeled protein was combined with polysaccharide with a conjugation ratio of PS/Prot 6:1 w/w. Product purified by 2×HA column. First run (BLOCK 1=NaPi 2 mM pH 7.2, BLOCK 2=NaPi 400 mM pH 7.2) removes free protein. Second run (BLOCK 1=NaPi 2 mM/NaCl 550 mM pH 7.2, BLOCK 2=NaPi 10 mM pH 7.2, BLOCK 3=NaPi 35 mM pH 7.2, BLOCK 4=NaPi 400 mM pH 7.2) removes free polysaccharide.
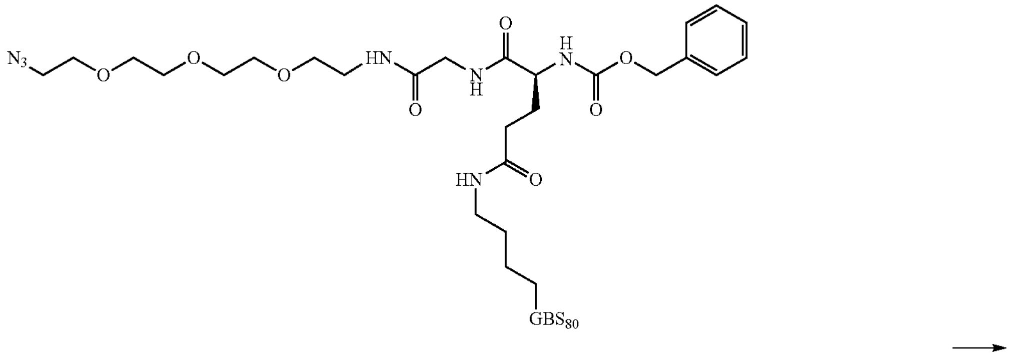

-continued
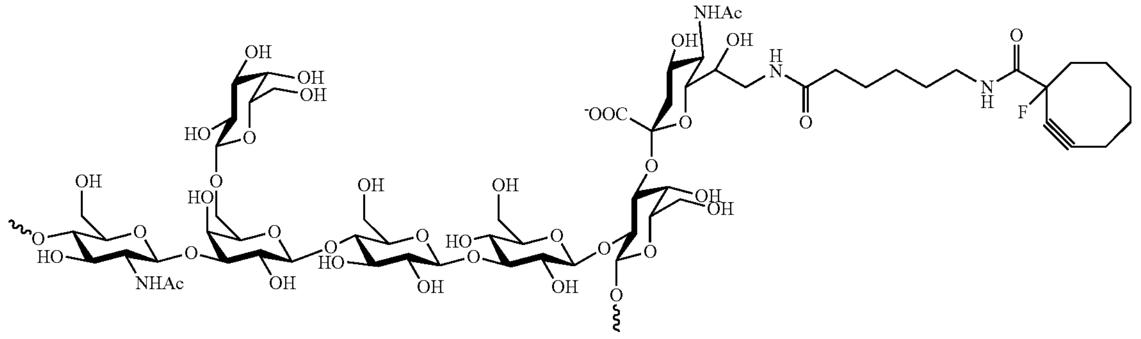
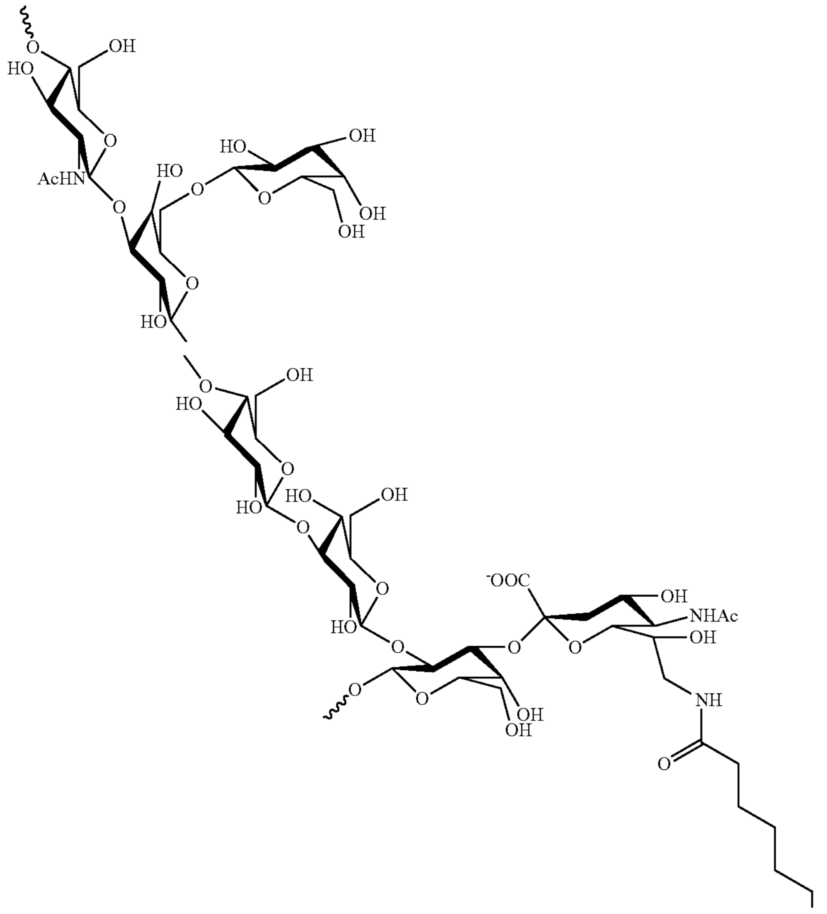

-continued

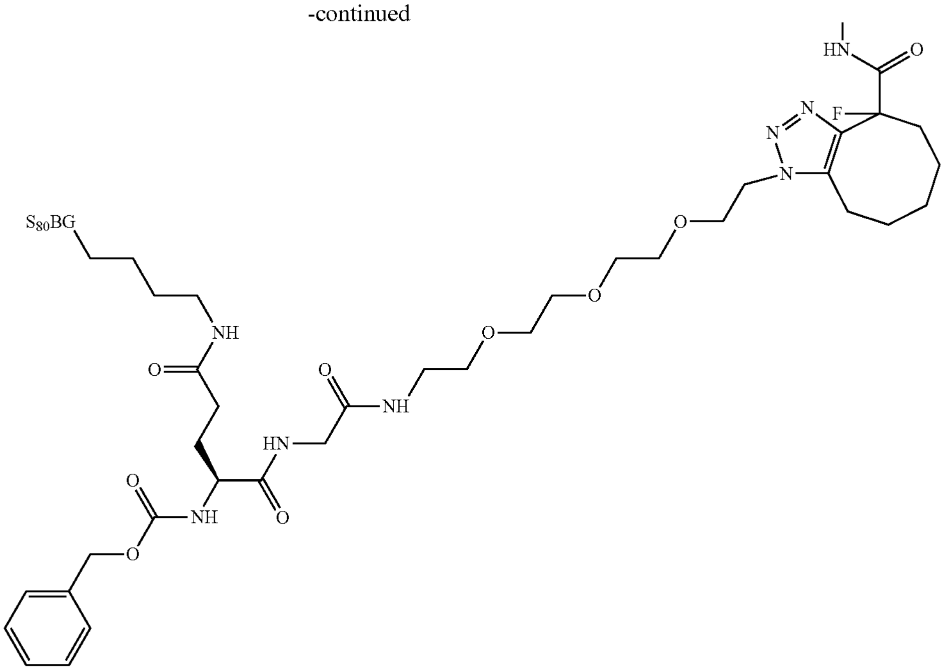

3.3 mg of azido labeled protein was combined with polysaccharide with a conjugation ratio PS/Prot 6:1 w/w. Product purified by 2×HA column. First run (BLOCK 1=NaPi 2 mM pH 7.2, BLOCK 2=NaPi 400 mM pH 7.2) removes free protein. Second run (BLOCK 1=NaPi 2 mM/NaCl 550 mM pH 7.2, BLOCK 2=NaPi 10 mM pH 7.2, BLOCK 3=NaPi 35 mM pH 7.2, BLOCK 4=NaPi 400 mM pH 7.2) removes free polysaccharide.

Figure 2:
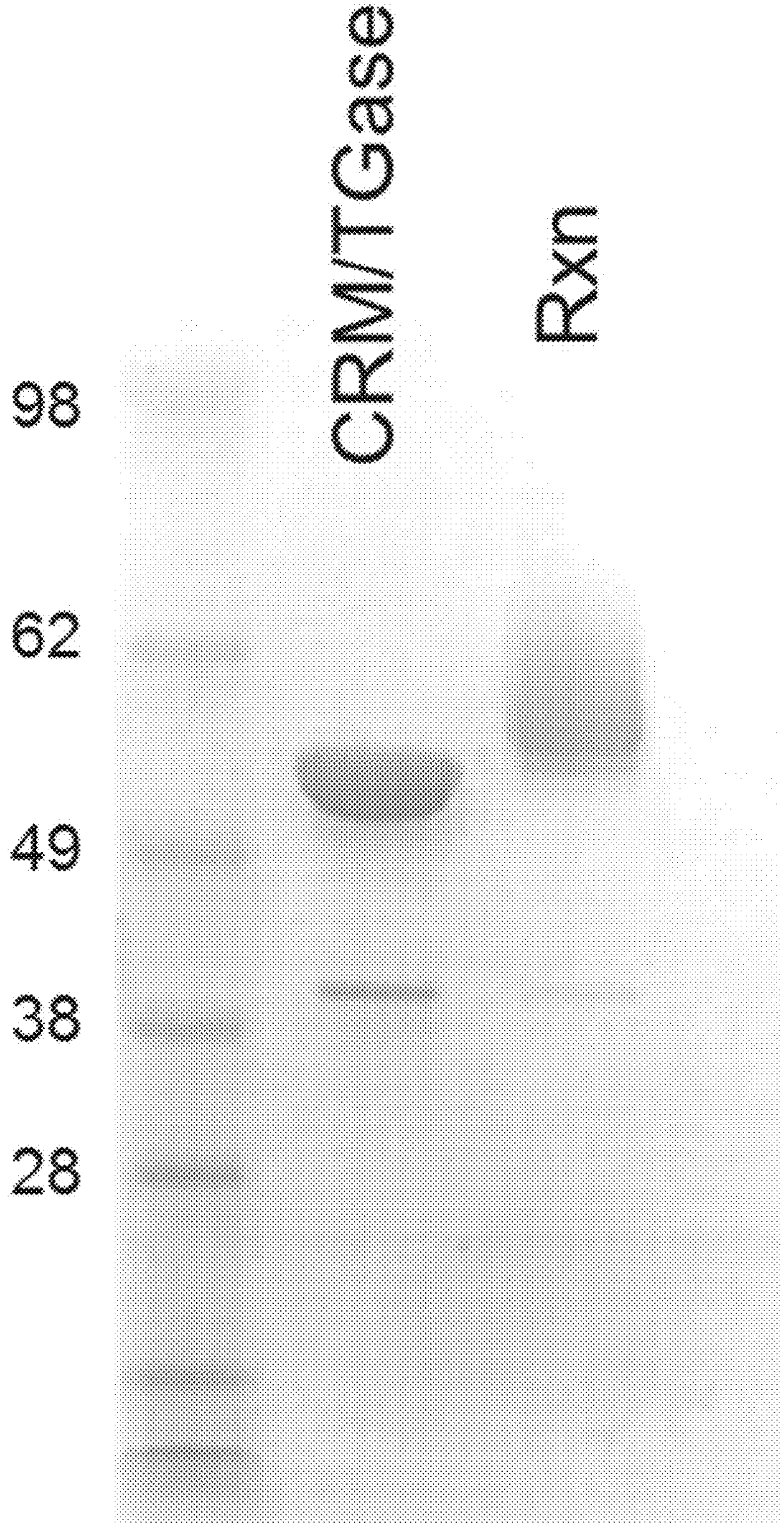
FIG. 2 is an SDS-Page gel electrophoresis characterizing the conjugation of MenA polysaccharide with $CRM_{197}$ using a compound of the invention.
Figure 3:
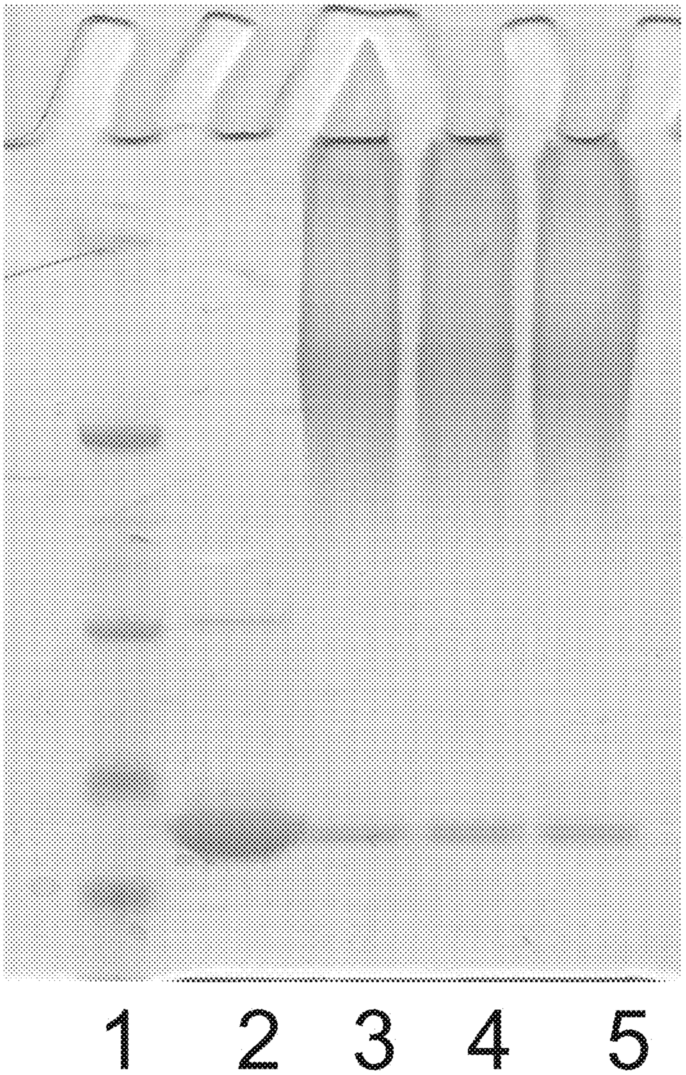
FIG. 3 is an SDS-Page gel electrophoresis characterizing the site selective conjugation of GBS80 antigenic polysaccharide with $CRM_{197}$ using a compound of the invention, wherein lane 1 is MW, lane 2 is GBS80-K—$N_3$, lane 3 is GBS80-K—$N_3$/PSV 1 mg of protein, lane 4 is GBS80-K—$N_3$/PSV 1 mg of protein, and lane 5 is GBS80-K—$N_3$/PSV 1 mg of protein.
Figure 4:
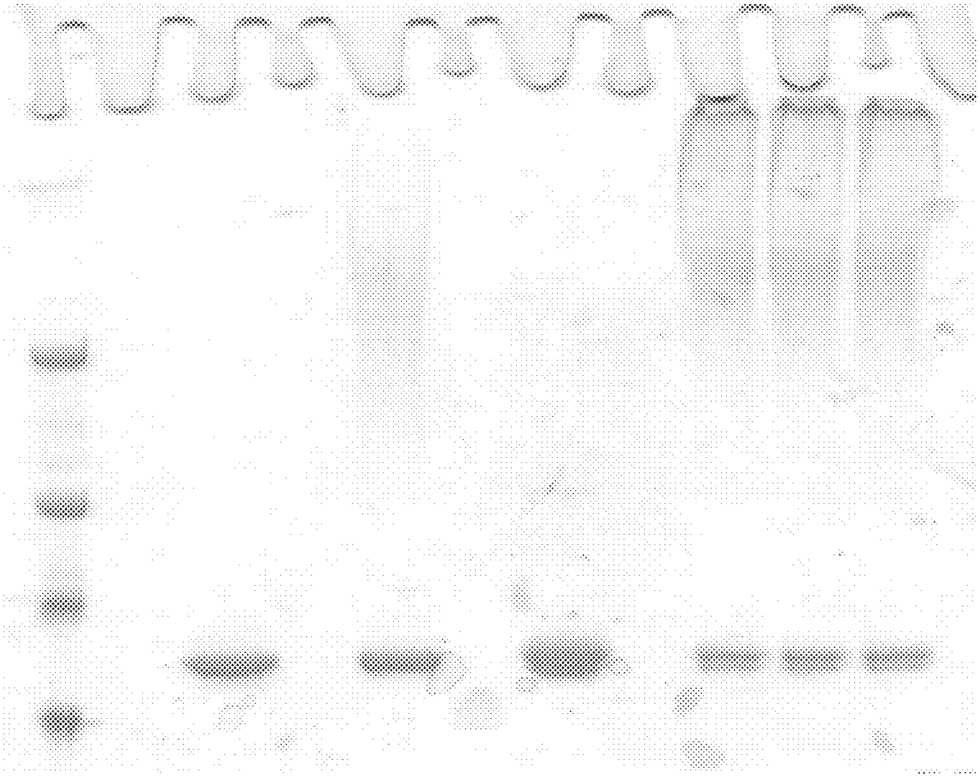
FIG. 4 is an SDS-Page gel electrophoresis characterizing the resulting reaction of a conjugated GBS80 antigenic polysaccharide with $CRM_{197}$ using a compound of the invention, wherein lane 1 is MW, lane 2 is GBS80-K—$N_3$, lane 3 is GBS80-K—$N_3$/PSII 1 mg of protein, lane 4 is GBS80-K—$N_3$/PSII 1 mg of protein, and lane 5 is GBS80-K—$N_3$/PSII 1 mg of protein.

As shown in FIGS. 2-4, SDS page gel characterization of products of these experiments were obtained. The respective yields are also shown in Table 3 below.

TABLE 3

| Sample | Protein | Conjugation chemistry | Sacch/ Prot (w/w) | Free saccharide % (dionex) | Protein TOT mg | Saccharide/ protein used for conjugation (w/w) | Yield (% final protein) |
|---|---|---|---|---|---|---|---|
| GBS PSV(alk)-GBS80(K-N3) | X | CFCC | 4.3 | 6.7 | 570.7 | 6:1 | 20.6 |
| GBS PSII(alk)-GBS80(K-N3) | X | CFCC | 1.5 | <3.3 | 1685.7 | 6:1 | 24.0 |

Each of these clicked GBS80 conjugates obtained through the mTGase labeling method were tested biologically assays discussed below.

ELISA Immuno Assay for Determination of Ig Titers Against GBS II or V Polysaccharide Antigens IgG titers against GBS polysaccharides II or V in the sera from immunized animals were measured as follows.

Figure 5:
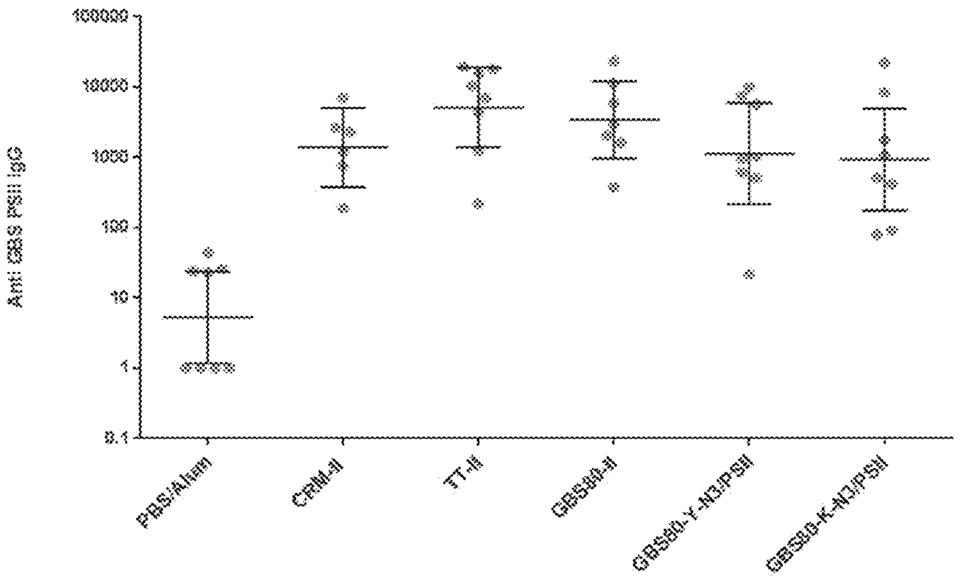
FIG. 5 shows ELISA immunoassay results for determination of Ig titers against GBS II polysaccharide antigen, wherein ELISA anti PSII IgG and survival results at 1.0 ug dose of PS.
Figure 6:
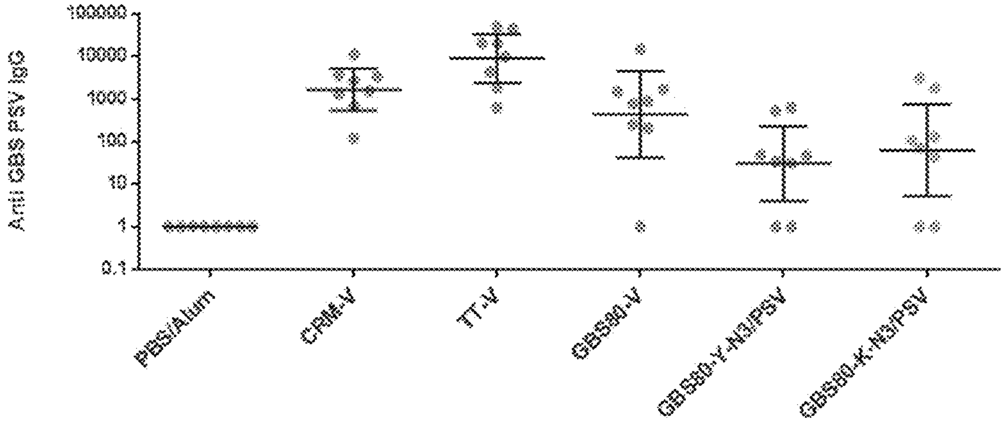
FIG. 6 shows ELISA immunoassay results for determination of Ig titers against GBS V polysaccharide antigen, wherein ELISA anti PSV IgG and survival results at 1.0 ug dose of PS.

Microtiter plates (Nunc Maxisorp) were coated with 100 μl of 1.0 μg/mL HSA-adh (Human Serum Albumin-adipic acid dihydrazide) conjugated polysaccharides II or V in Phosphate Buffered Saline (PBS). The plate was incubated overnight at room temperature and then washed three times in washing buffer (0.05% Tween 20 in PBS). After dispensing 250 μl of PBS, 2% BSA, 0.05% Tween 20 per well, plates were incubated 90 minutes at 37° C. and then aspirated to remove the post-coating solution. Test sera were diluted 1:400 in PBS, 2% BSA, 0.05% Tween 20. Standard serum was prepared by pooling hyper immune sera and initial dilutions of standard pools were chosen to obtain an optical density (OD) of about 2.000 at 405 nm. The plates were incubated for 1 hour at 37° C. and then washed with washing buffer and 100 μL of Alkaline Phosphatase-Conjugated anti-mouse IgG 1:1000 in dilution buffer were dispensed in each well. The plates were incubated 90 minutes at 37° C. and then washed with washing buffer. 100 μL of a solution of p-NitroPhenylPhosphate (p-NPP) 4.0 mg/mL in substrate buffer were dispensed in each well. The plates were incubated 30 minutes at room temperature and then 100 μL of a solution of EDTA 7% (w/v) disodium salt plus $Na_2HPO_4$ 3.5% pH 8.0, were added to each well to stop the enzymatic reaction. The optical density (OD) at 405 nm was measured. Total IgG titres against GBS polysaccharide antigens (II or V) were calculated by using the Reference Line Assay Method and results were expressed as arbitrary ELISA Units/mL (EU/mL). For each of the three antigens, the standard serum IgG titer was arbitrarily assigned a value of 1.0 EU/mL. The IgG titer of each serum was estimated by interpolating the obtained ODs with the titration curve (bias and slope) of the standard pool. Results are displayed in FIGS. 5 and 6.

Mouse Active Maternal Immunization Model

Groups of eight CD-1 female mice (age, 6-8 weeks) were immunized on days 1, 21, and 35 with 20 mg of antigen or buffer (PBS) formulated in alum adjuvant. Mice were then mated, and their offspring were challenged intraperitoneally with a GBS dose calculated to induce dead in 90% of the pups.

Protection values were calculated as [(% dead in control−% dead in vaccine)/% dead in control]×100. Mice were monitored on a daily basis and killed when they exhibited defined humane endpoints that had been pre-established for the study in agreement with Novartis Animal Welfare Policies. Statistical analysis was performed using Fisher's exact test. Results are displayed in Tables 4 and 5 below.

TABLE 4

| Antigens | Protected\Treated | % Protection |
|---|---|---|
| PBS | 18/60 | 30 |
| CRM-II | 32/50 | 64 |
| TT-II | 19/30 | 63 |
| GBS80-II | 37/70 | 53 |
| GBS59-1523-II | 59/70 | 84 |
| GBS80-K-N3/PSII | 58/69 | 84 |

challenge strain type II 5401

TABLE 5

| Antigens | Protected\Treated | % Protection |
|---|---|---|
| PBS | 19/40 | 47 |
| CRM-V | 61/70 | 87 |
| TT-V | — | — |
| GBS80-V | 54/57 | 95 |

TABLE 5-continued

| Antigens | Protected\Treated | % Protection |
|---|---|---|
| GBS59-1523-V | 69/79 | 87 |
| GBS80-K-N3/PSV | 53/60 | 88 |

challenge strain type V CJB111

Opsonophagocytosis Assay

The opsonophagocytosis assay was performed using GBS strains as target cells and HL-60 cell line (ATCC; CCL-240), differentiated into granulocyte-like cells, by adding 100 mM N, N dimethylformamide (Sigma) to the growth medium for 4 d. Mid-exponential bacterial cells were incubated at 37° C. for 1 h in the presence of phagocytic cells, 10% baby rabbit complement (Cedarlane), and heat-inactivated mouse antisera. Negative controls consisted of reactions either with preimmune sera, or without HL-60, or with heat-inactivated complement. The amount of opsonophagocytic killing was determined by subtracting the log of the number of colonies surviving the 1-h assay from the log of the number of CFU at the zero time point.

Figure 7:
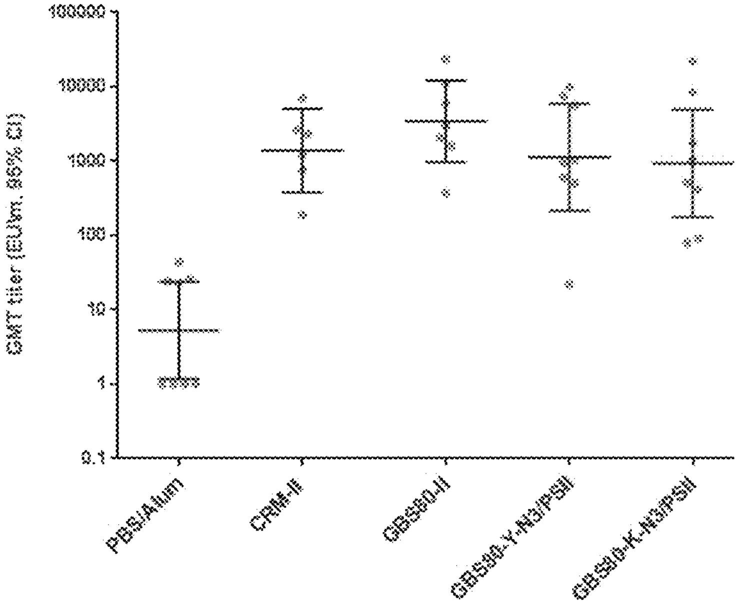
FIG. 7 shows opsonophagocytosis assay results for using GBS strains.

Results of the experiments are shown in FIG. 7. GBS80-K-$N_3$/PSII OPKA and IgG titers are statistically comparable to GBS80-II conjugate made by random K conjugation. OPKA and IgG titers show good correlation with % of survival in challenge animal model.

Ac-L-Q-G-NH—$(CH_2)_2$—C(O)—$(CH_2)_2$—$SO_2$-Tol

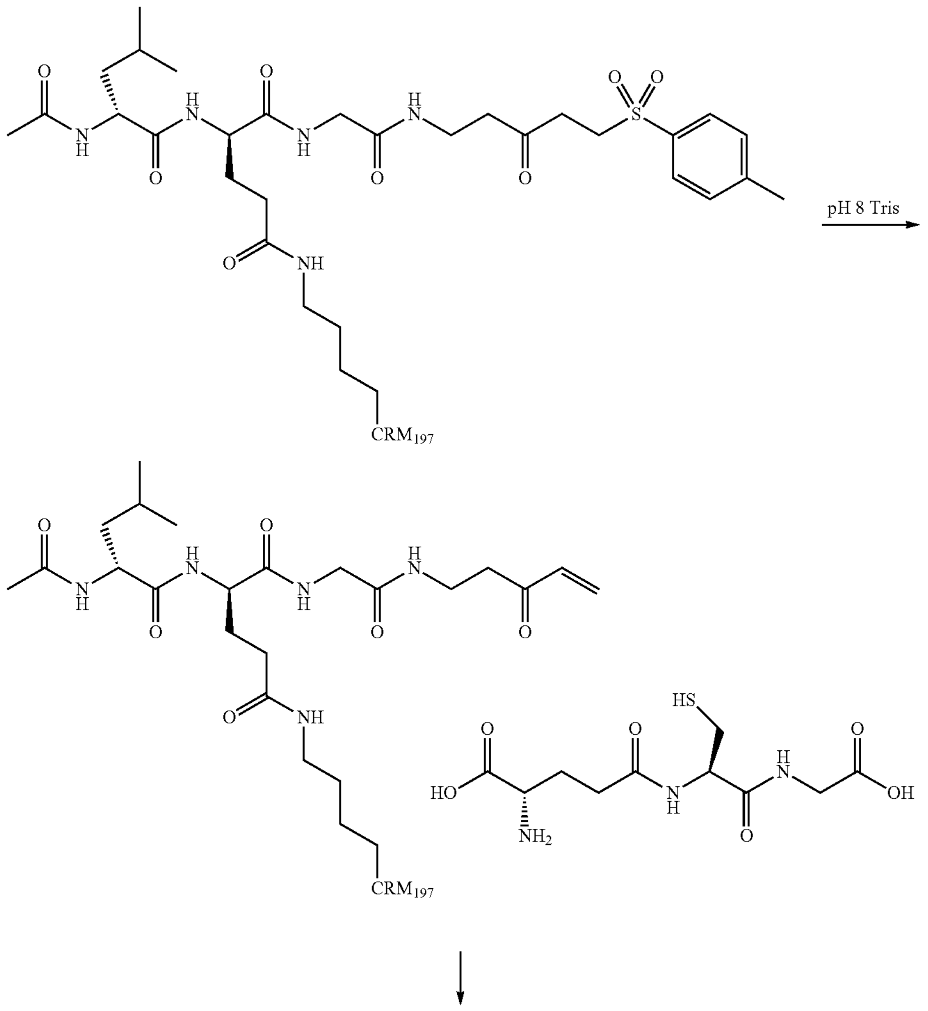

-continued

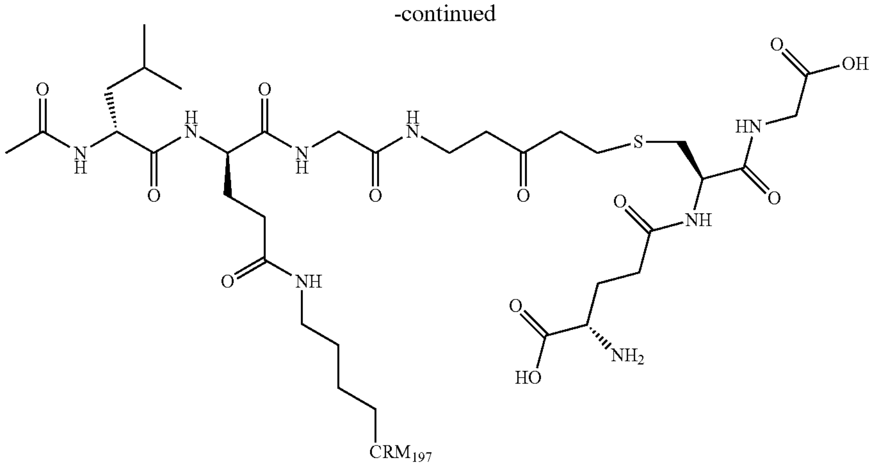

L-Glutathione (5 μL, 0.813 umol) was added followed by 50 μL of 250 mM Tris HCl buffer pH 8, raising the reaction pH to 8. After 4 hours, all of CRM was labeled with one linker as confirmed by mass spectrometry characterization. After another 16 hours at 25° C., all of CRM was labeled with L-Glutathione. Addition of the L-Glutathione: Expected Mass: 59138, Observed Mass: 59139.

Peptide Mapping Experimental Summary:

Peptide Mapping Digestion: 5 μg modified CRM197 and positive control CRM197 samples were reduced with 20 mM DTT and digested with 1/30 (w/w) enzyme/protein at 26° C. overnight with trypsin. An aliquot of trypsin digested protein was further digested with GluC enzyme at 1/20 enzyme/protein ratio for 4 hr at 26° C.; note all enzymes purchased from Roche Diagnostics (Gmbh, Germany).

Reverse Phase LC-MS/MS Analysis: Resulting digested peptides were analyzed by liquid chromatography electrospray tandem mass spectrometry (LC-ESI MS/MS) on a Thermo LTQ Orbitrap Discovery (Thermo Fisher Scientific Inc., Waltham, Mass.) coupled to Agilent CapLC (Santa Clara, Calif.). Loaded ~10-15 pmole of CRM control and modified CRM197 digests on column at 40° C. (Waters Acuity BEH C18, 1.7 μm, 1×100 mm column) Ran 80 min total gradient at 10 μL/min stating at 0-1 min, 4% B, increased to 7% B at 1.1 min, 45% B at 55 min, then 95% B at 63 min, followed by washing and column equilibration. Mass spectrometer parameters included a full scan event using the FTMS analyzer at 30000 resolution from m/z 300-2000 for 30 ms. Collision Induced Dissociation MS/MS was conducted on the top seven intense ions (excluding 1+ ions) in the ion trap analyzer, activated at 500 (for all events) signal intensity threshold counts for 30 ms.

Data Analysis and Database Searching: All mass spectra were processed in Qual Browser V 2.0.7 (Thermo Scientific). Mascot generic files (mgf) were generated with MS DeconTools (R.D. Smith Lab, PPNL) and searched using Mascot V2.3.01 (Matrix Science Inc., Boston, Mass.) database search against the provided protein sequence added to an in-house custom database and the SwissProt database (V57 with 513, 877 sequences) for contaminating proteins. Search parameters included: enzyme: semitrypsin or trypsin/Glu-C, allowed up to three missed cleavage; variable modifications: added expected masses of small molecules (362.147787 Da and 463.206698 Da) to database called "CRM Tgase+alkyne 362 Da mod (CKR), CRM Tgase+alkyne 362 Da mod (N-term), CRM Tgase+azide 463 Da mod (CKR), CRM Tgase+azide 463 Da mod (N-term)"; peptide tolerance: ±20 ppm; MS/MS tolerance: ±0.6 Da. Sequence coverage and small molecule modification assessments were done on ions scores with >95% confidence. High-scoring peptide ions were then selected for manual MS/MS analysis using Qual Browser.

Results for CRM+Cyclooctyne-Cyclopropyl-$CH_2$—OC(O)NH-Q-G

Trypsin digest: 83% sequence coverage; No modification detected at this ion score threshold. Trypsin/GluC digest: 97% sequence coverage; Modification detected on Lys37 or Lys39.

CRM Exp095 Trypsin/GluC Digestion
Sequence Coverage: 91%, Matched peptides shown in Bold Text K37 or K39 Modified with CRM Tgase + azide 463 Da mod (CKR)

SEQ ID NO: 1

1 GADDVVDSSKSFVMENFSSYHGTKPGYVDSIQKGIQKPKSGTQG NYDDDW

51 KEFYSTDNKYDAAGYSVDNENPLSGKAGGVVKVTYPGLTKVLALKV DNAE

101 TIKKELGLSLTEPLMEQVGTEEFIKRFGDGASRVVLSLPFAEGSSS VEYI

151 NNWEQAKALSVELEINFETRGKRGQDAMYEYMAQACAGNRVRRSVG SSLS

201 CINLDWDVIRDKTKTKIESLKEHGPIKNKMSESPNKTVSEEKAKQY LEEF

251 HQTALEHPELSELKTVTGTNPVFAGANYAAWAVNVAQVIDSETADN LEKT

301 TAALSILPGIGSVMGIADGAVHHNTEEIVAQSIALSSLMVAQAIPL VGEL

351 VDIGFAAYNFVESIINLFQVVHNSYNRPAYSPGHKTQPFLHDGYAV SWNT

401 VEDSIIRTGFQGESGHDIKITAENTPLPIAGVLLPTIPGKLDVNKS KTHI

451 SVNGRKIRMRCRAIDGDVTFCRPKSPVYVGNGVHANLHVAFHRSSS EKIH

501 SNEISSDSIGVLGYQKTVDHTKVNSKLSLFFEIKS

Results for CRM+ZQ-NH-$(PEG)_3N_3$

Trypsin digest: 69% sequence coverage; No modification detected at this ion score threshold. Trypsin/GluC digest: 91% sequence coverage; Modification detected on Lys37 or Lys39.

```
CRM Exp083 Trypsin/GluC Digestion
Sequence Coverage: 97%, Matched peptides shown in
Bold Text K37 or K39 Modified with CRM Tgase +
alkyne 362 Da mod (CKR)
                                      SEQ ID NO: 2
```

1 GADDVVDSSKSFVMENFSSYHGTKPGYVDSIQKGIQKPKSGTQG NYDDDW

51 KEFYSTDNKYDAAGYSVDNENPLSGKAGGVVKVTYPGLTKVLALKV DNAE

101 TIKKELGLSLTEPLMEQVGTEEFIKRFGDGASRVVLSLPFAEGSSS VEYI

151 NNWEQAKALSVELEINFETRGKRGQDAMYEYMAQACAGNRVRRSVG SSLS

201 CINLDWDVIRDKTKTKIESLKEHGPIKNKMSESPNKTVSEEKAKQY LEEF

251 HQTALEHPELSELKTVTGTNPVFAGANYAAWAVNVAQVIDSETADN LEKT

-continued

301 TAALSILPGIGSVMGIADGAVHHNTEEIVAQSIALSSLMVAQAIPL VGEL

351 VDIGFAAYNFVESIINLFQVVHNSYNRPAYSPGHKTQPFLHDGYAV SWNT

401 VEDSIIRTGFQGESGHDIKITAENTPLPIAGVLLPTIPGKLDVNKS KTHI

451 SVNGRKIRMRCRAIDGDVTFCRPKSPVYVGNGVHANLHVAFHRSSS EKIH

501 SNEISSDSIGVLGYQKTVDHTKVNSKLSLFFEIKS

CRM Control

Trypsin digest: 85% sequence coverage.

Trypsin/GluC digest: 79% sequence coverage.

It is understood that the invention is not limited to the embodiments set forth herein for illustration, but embraces all such forms thereof as come within the scope of the above disclosure.

PROPHETIC EXAMPLES

Benzyl (17-amino-1-(4-azido2-nitrophenyl)-2,13,17-trioxo-6,9-dioxa-3,12-diazaheptadecan-14-yl)carbamate

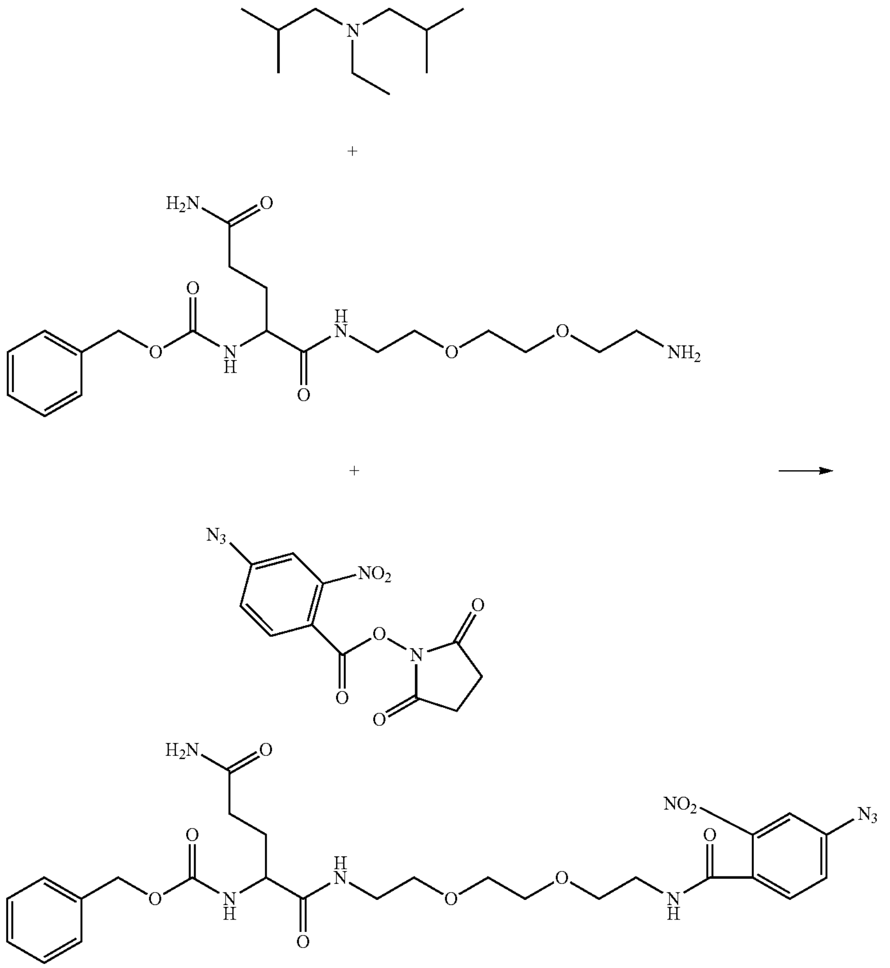

4-azido-2-nitrophenylacetic acid N-succinimido ester (0.073 mmol) is dissolved in DMF (1 mL) and combined with a solution of benzyl (5-amino-1-((2-(2-(2-aminoethoxy)ethoxy)ethyl)amino)-1,5-dioxopentan-2-yl)carbamate (20 mg, 0.049 mmol) in DMF (2.3 mL). DIPEA (0.121 mL, 0.585 mmol) is added and the reaction is mixed at r.t. for 4 hours. The solution is purified via MS-triggered HPLC (100-Prep3; Acid_Method 3; Sunfire 30×50 mm Sum column ACN/$H_2O$ w/0.1% TFA 75 ml/min, 1.5 ml injection; Tube Trigger M=570). Fractions with desired product are pooled and lyophilized.

ZQ-(PEG2) phenyl trifluoromethyldiazirine

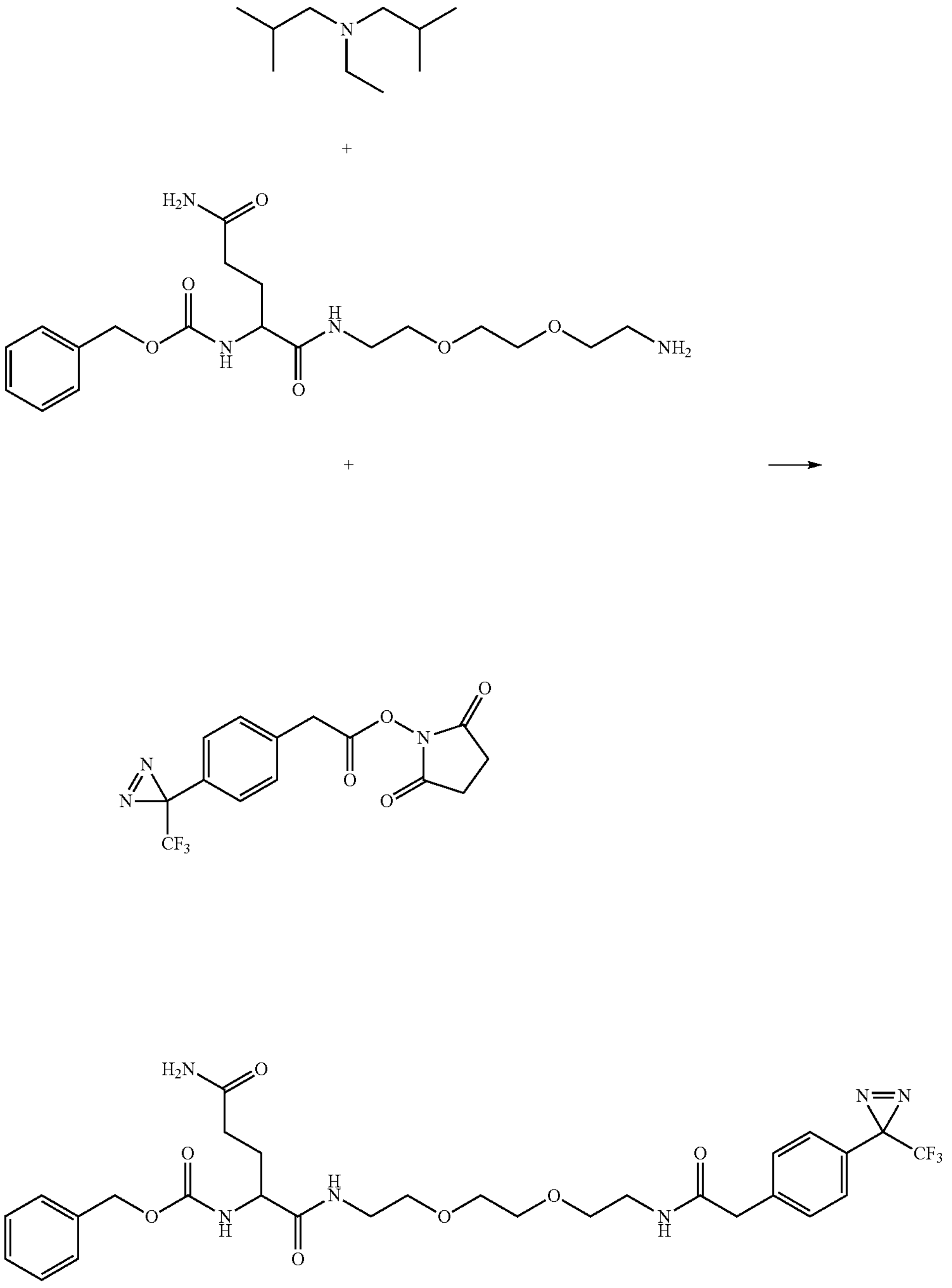

4-trifluoromethyl diazirine phenylacetic acid N-succinimido ester (0.073 mmol) is dissolved in DMF (1 mL) and combined with a solution of benzyl (5-amino-1-((2-(2-(2-aminoethoxy)ethoxy)ethyl)amino)-1,5-dioxopentan-2-yl) carbamate (20 mg, 0.049 mmol) in DMF (2.3 mL). DIPEA (0.121 mL, 0.585 mmol) is added and the reaction is mixed at r.t. for 4 hours. The solution is purified via MS-triggered HPLC (100-Prep3; Acid_Method 3; Sunfire 30×50 mm 5um column ACN/$H_2O$ w/0.1% TFA 75 ml/min, 1.5 ml injection; Tube Trigger M=570). Fractions with desired product are pooled and lyophilized.

ZQ-(PEG2)-tetrazine

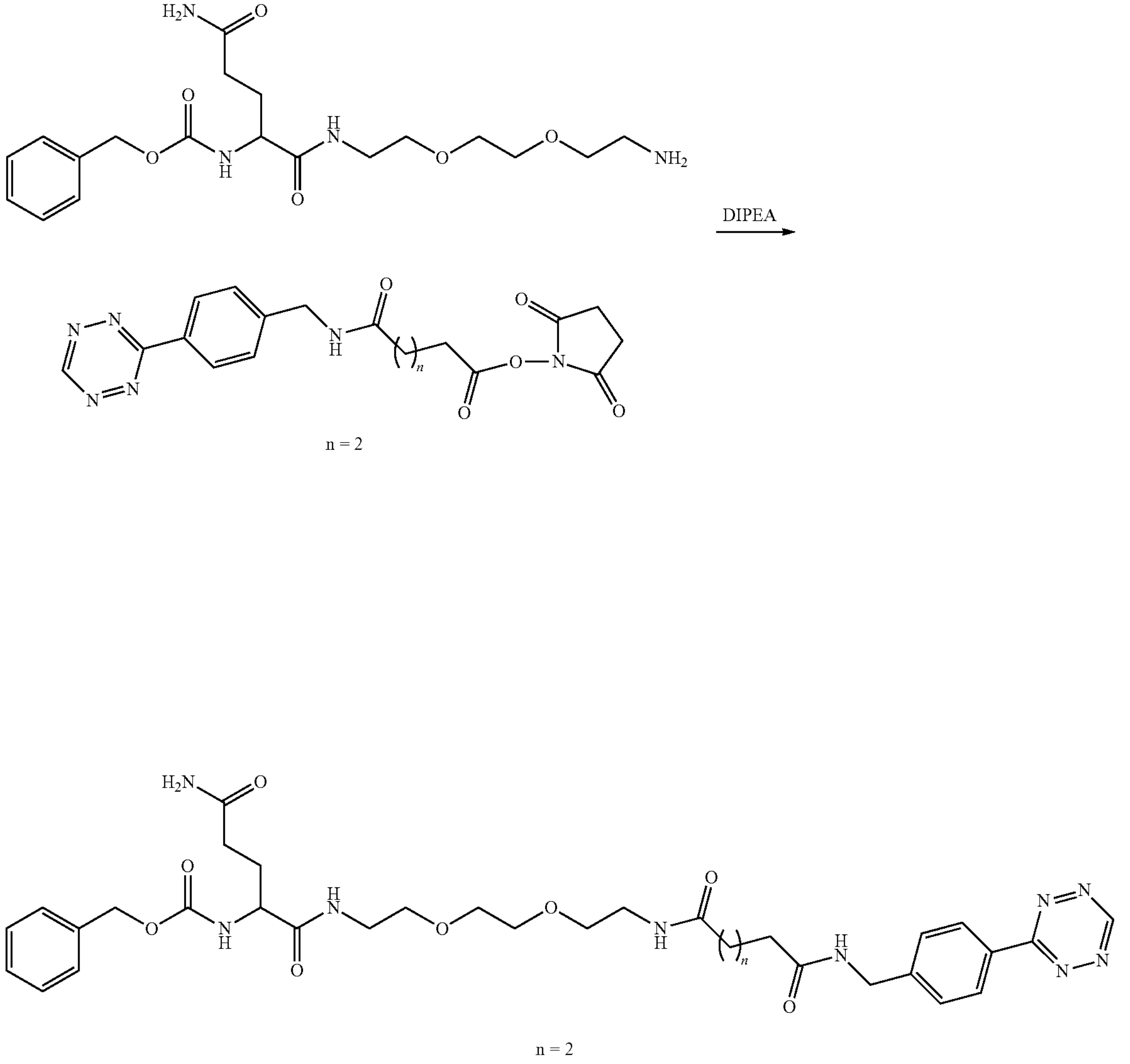

Diazirine N-succinimido ester (0.073 mmol) is dissolved in DMF (1 mL) and combined with a solution of benzyl (5-amino-1-((2-(2-(2-aminoethoxy)ethoxy) ethyl)amino)-1, 5-dioxopentan-2-yl)carbamate (20 mg, 0.049 mmol) in DMF (2.3 mL). DIPEA (0.121 mL, 0.585 mmol) is added and the reaction is mixed at r.t. for 4 hours. The solution is purified via MS-triggered HPLC (100-Prep3; Acid_Method 3; Sunfire 30×50 mm Sum column ACN/$H_2O$ w/0.1% TFA 75 ml/min, 1.5 ml injection; Tube Trigger M=570). Fractions with desired product are pooled and lyophilized.

ZQ-(PEG2)-tetrazine

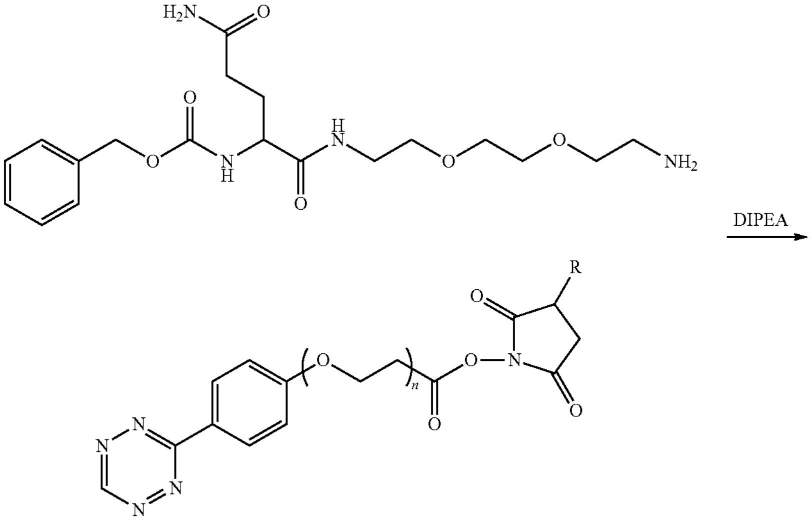

n = 4-6
R = $SO_3Na$

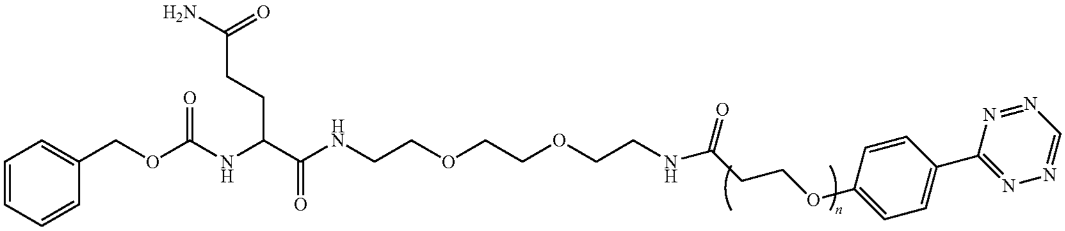

n = 4-6

Tetrazine (PEG)N-succinimido ester (0.073 mmol) is dissolved in DMF (1 mL) and combined with a solution of benzyl (5-amino-1-((2-(2-(2-aminoethoxy)ethoxy)ethyl) amino)-1,5-dioxopentan-2-yl)carbamate (20 mg, 0.049 mmol) in DMF (2.3 mL). DIPEA (0.121 mL, 0.585 mmol) is added and the reaction is mixed at r.t. for 4 hours. The solution is purified via MS-triggered HPLC (100-Prep3; Acid_Method 3; Sunfire 30×50 mm Sum column ACN/$H_2O$ w/0.1% TFA 75 ml/min, 1.5 ml injection; Tube Trigger M=570). Fractions with desired product are pooled and lyophilized.

ZQ(PEG2)-(3aR,4S,7R)-3a,4,7,7a-tetrahydro-4,7-methanoisobenzofuran-1,3-dione

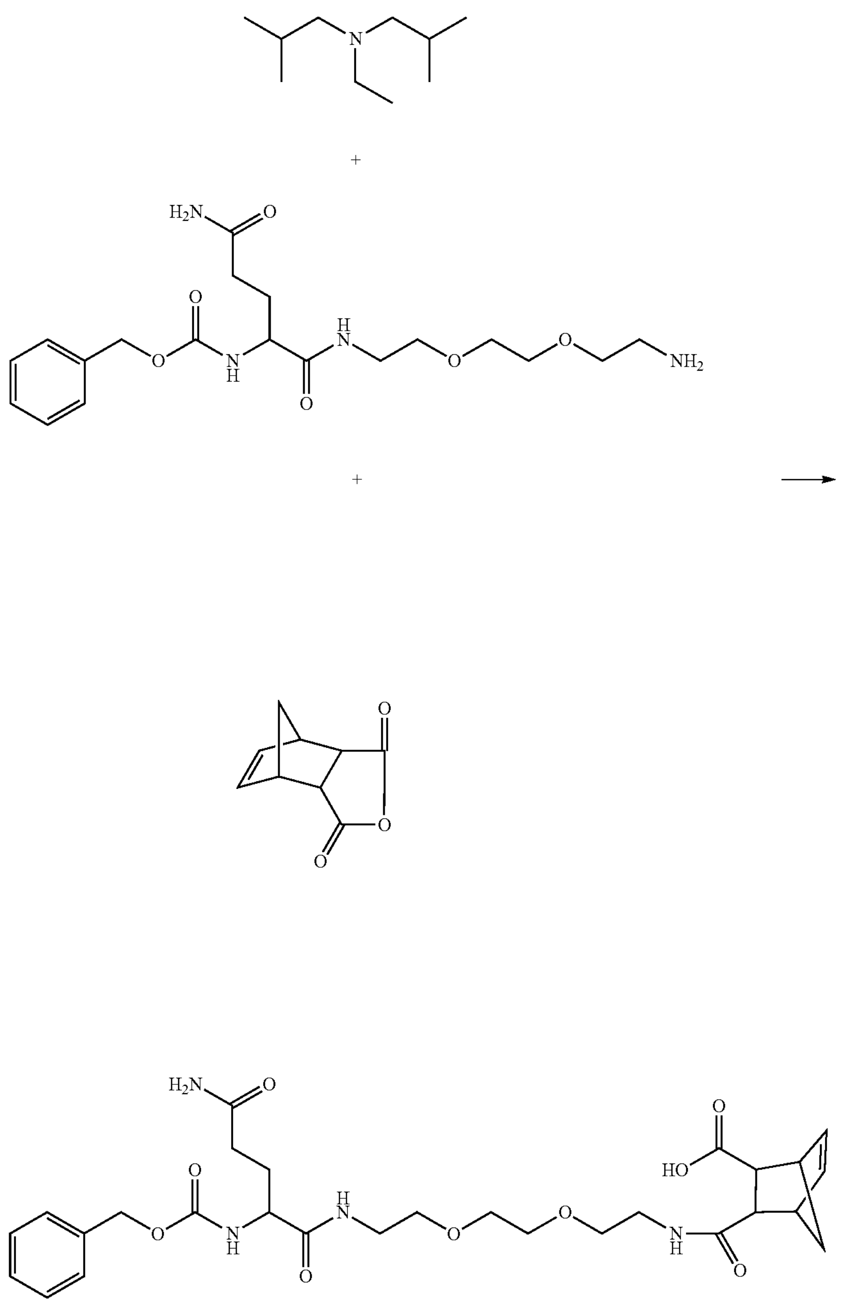

(3aR,4S,7R)-3a,4,7,7a-Tetrahydro-4,7-methanoisobenzofuran-1,3-dione (0.162 mmol) (0.073 mmol) is dissolved in DMF (1 mL) and combined with a solution of benzyl (5-amino-1-((2-(2-(2-aminoethoxy)ethoxy)ethyl)amino)-1,5-dioxopentan-2-yl)carbamate (0.049 mmol) in DMF (2.3 mL). DIPEA (0.585 mmol) is added and the reaction is mixed at r.t. for 4 hours. The solution is purified via MS-triggered HPLC (100-Prep3; Acid_Method 3; Sunfire 30×50 mm Sum column ACN/$H_2O$ w/0.1% TFA 75 ml/min, 1.5 ml injection; Tube Trigger M=570). Fractions with desired product are pooled and lyophilized.

Tetrazine-QG

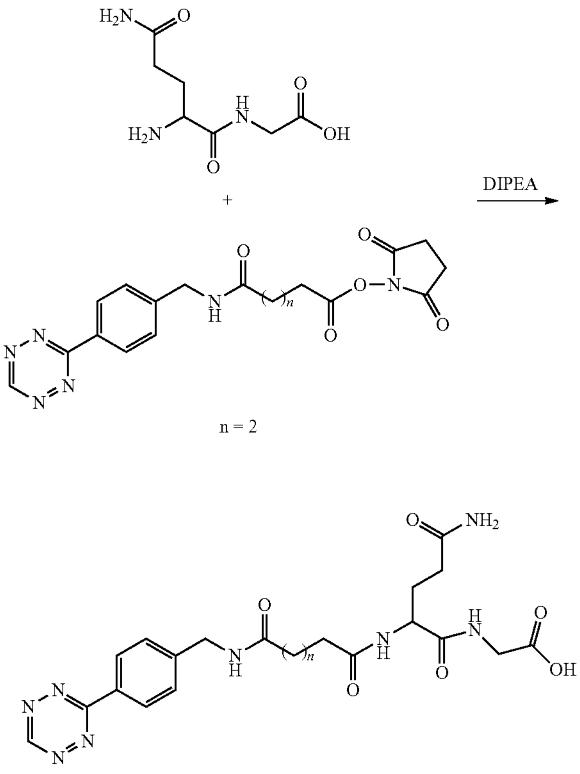

n = 2 n = 2

QG (30 mg, 0.148 mmol) is dissolved in DMF (Volume: 1 mL, Ratio: 1.000) and NHS tetrazine (0.148 mmol) is added in $H_2O$ (Volume: 1.000 mL, Ratio: 1.000) followed by addition of DIPEA (0.177 mmol). The reaction stirs for 16 hours at which time the product is purified by HPLC (Sunfire 30×50 mm 5 um column ACN/H2O w/0.1% TFA 75 ml/min 1.5 ml injection) to give the desired product. Fractions are pooled and lyophilized.

Tetrazine(PEG)-QG

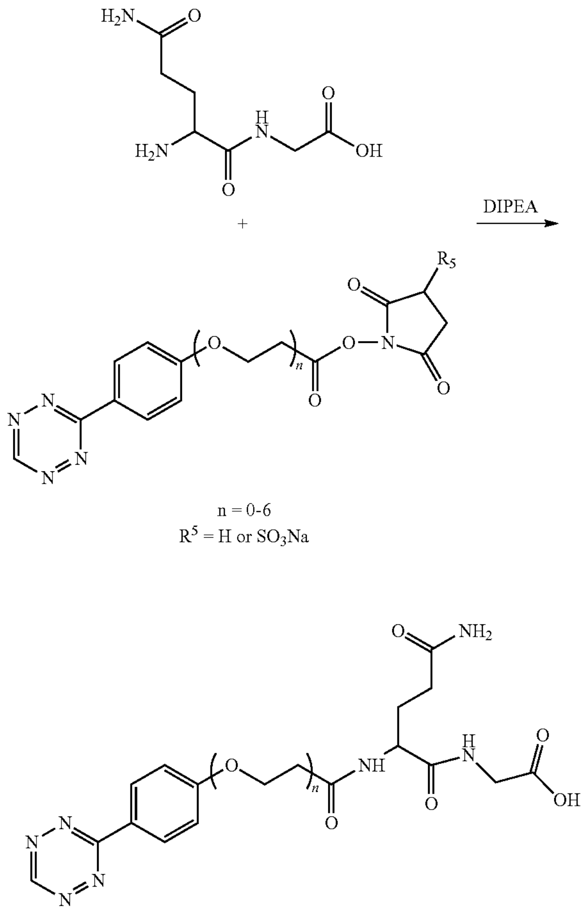

n = 0-6

$R^5$ = H or $SO_3Na$ n = 0-6

QG (30 mg, 0.148 mmol) is dissolved in DMF (Volume: 1 mL, Ratio: 1.000) and NHS $PEG_n$, tetrazine (0.148 mmol) is added in $H_2O$ (Volume: 1.000 mL, Ratio: 1.000) followed by addition of DIPEA (0.177 mmol). The reaction stirs for 16 hours at which time the product is purified by HPLC (Sunfire 30×50 mm 5 um column ACN/H2O w/0.1% TFA 75 ml/min 1.5 ml injection) to give the desired product. Fractions are pooled and lyophilized.

QG (30 mg, 0.148 mmol) is dissolved in DMF (Volume: 1 mL, Ratio: 1.000) and NHS tetrazine (0.148 mmol) is added in $H_2O$ (Volume: 1.000 mL, Ratio: 1.000) followed by addition of DIPEA (0.177 mmol). The reaction stirs for 16 hours at which time the product is purified by HPLC (Sunfire 30×50 mm Sum column ACN/H2O w/0.1% TFA 75 ml/min 1.5 ml injection) to give the desired product. Fractions are pooled and lyophilized.

4-Azido-phenyl-glutamine-glycine

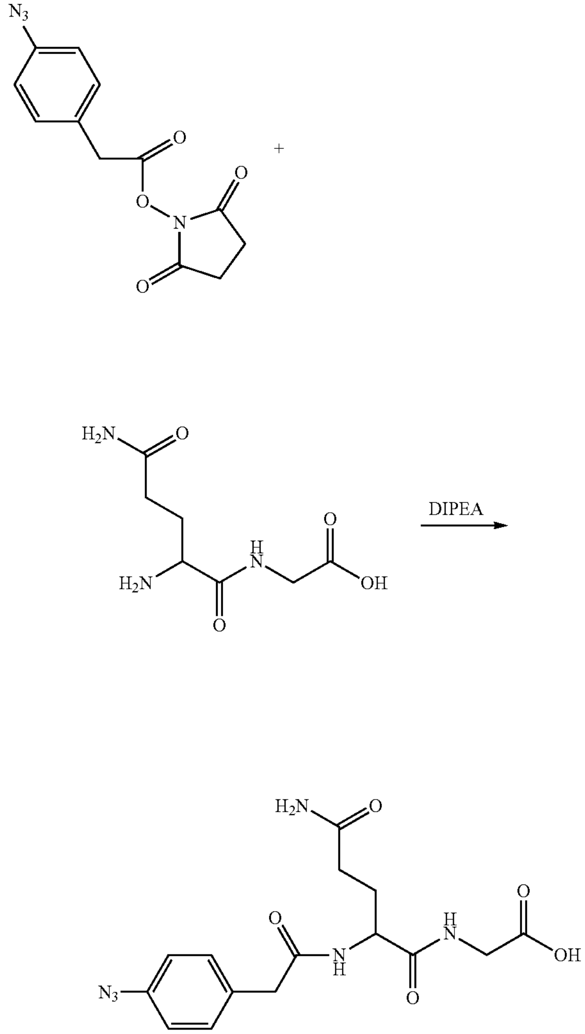

QG (30 mg, 0.148 mmol) is dissolved in DMF (Volume: 1 mL, Ratio: 1.000) and 4-azido-phenylacetic acid N-succinimido ester (0.148 mmol) is added in $H_2O$ (Volume: 1.000 mL, Ratio: 1.000) followed by addition of DIPEA (0.177 mmol). The reaction stirs for 16 hours at which time the product is purified by HPLC (Sunfire 30×50 mm Sum column ACN/H2O w/0.1% TFA 75 ml/min 1.5 ml injection) to give the desired product. Desired fractions are pooled and lyophilized.

Trifluoromethyldiazirine-benzyl-glutamine-glycine

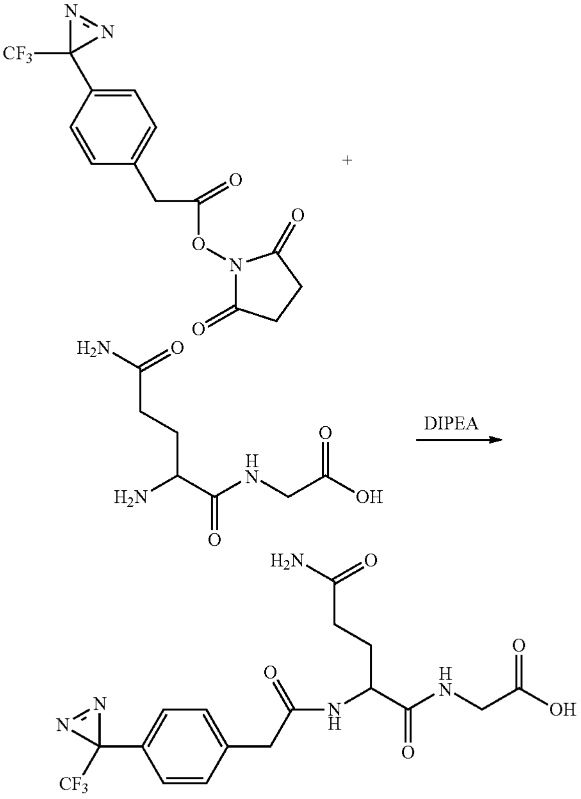

QG (30 mg, 0.148 mmol) is dissolved in DMF (Volume: 1 mL, Ratio: 1.000) and 4-trifluoromethyl-diazirine-phenylacetic acid N-succinimido ester (0.148 mmol) is added in $H_2O$ (Volume: 1.000 mL, Ratio: 1.000) followed by addition of DIPEA (0.177 mmol). The reaction stirs for 16 hours at which time the product is purified by HPLC (Sunfire 30×50 mm Sum column ACN/H2O w/0.1% TFA 75 ml/min 1.5 ml injection) to give the desired product. Desired fractions are pooled and lyophilized.

General Procedure for mTGase-Mediated Labelling of CRM197

To a solution of linker in tris buffer pH 8 (3.5 mg/mL, 0.527 μmol or other amount and relative micromolar concentration depending on the linker identified above) is added CRM197 (33 mg/mL, 7.55 μL, 0.0043 μmol) followed by a solution of transglutaminase enzyme in PBS (50 mg/mL, 7.61 μL, 0.0100 μmol). The reaction is stirred at rt or 37° C. for 16 hours.

Having thus described exemplary embodiments of the present invention, it should be noted by those of ordinary skill in the art that the within disclosures are exemplary only and that various other alternatives, adaptations, and modifications may be made within the scope of the present invention. Accordingly, the present invention is not limited to the specific embodiments as illustrated therein.

What is claimed is:

1. A compound of the formula $R^1$-(Leu)$_x$-Gln-(Gly)$_y$-(A-W-B-$R^2$)$_z$ wherein x is 0 or 1; y is 0 or 1; z is 0 or 1;

$R^1$ is selected from the group consisting of:

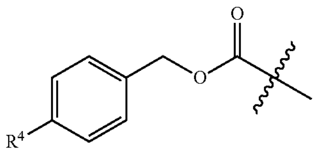

-continued

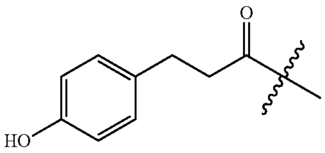

-continued

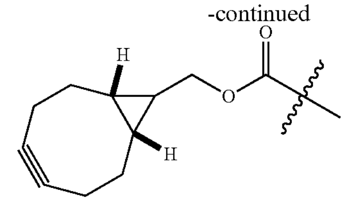

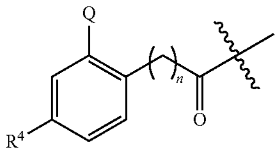

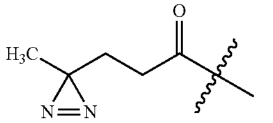

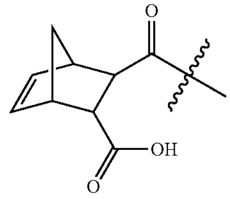

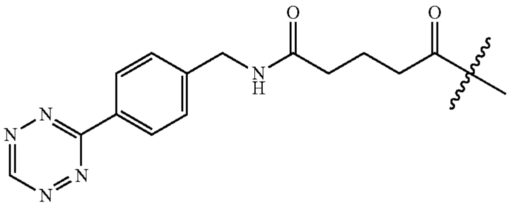

and

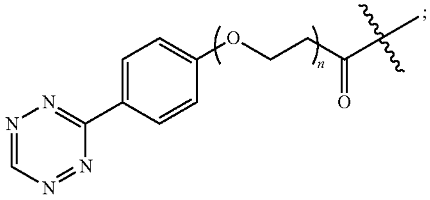

wherein $R^4$ is selected from —H, —$N_3$, and

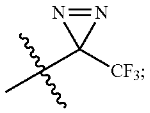 [SMILES: *C1(C(F)(F)F)N=N1]

W is selected from: $C_1$-$C_6$ linear or branches alkyl or polyethylene glycol having a molecular weight of between about 40 and about 80,000 amu;

A is absent or selected from —O—, —NH—, and —S—;

B is absent or selected from —O—, —C(O)—, —NH—, —C(O)NH—, —NHC(O)—, —NHC(O)O—, —OC(O)NH—, —OC(O)O—, —C═N(OH)—, —S(O2)—, —NHS($O_2$)—, —S($O_2$)NH—, —S(O)—, —NHS(O)—, —S(O)NH—; —C(O)O—, —OC(O)—, —S—, ═NH—O—, ═NH—NH— and ═NH—N($C_1$-$C_{20}$alkyl)-;

$R^2$ is selected from the group consisting of: a fatty acid, linear or branched $C_1$-$C_3$ alkyl-$N_3$, cyclooctynyl, polysaccharide, —CH($OCH_3$)$_2$,

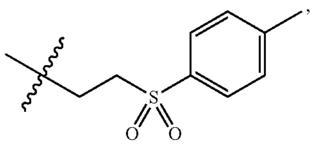

-continued

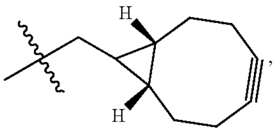

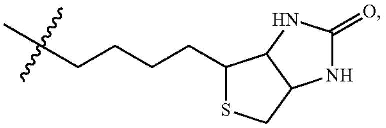

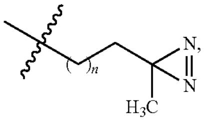

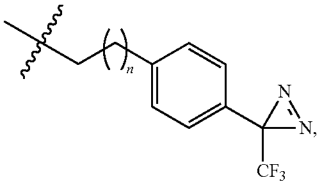

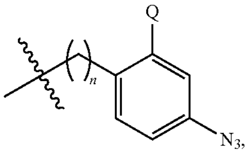

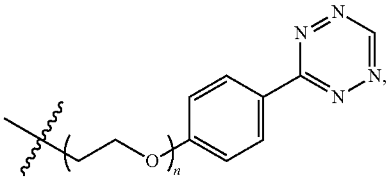

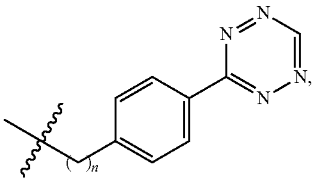

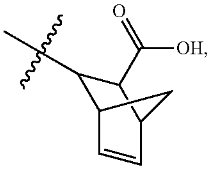

and

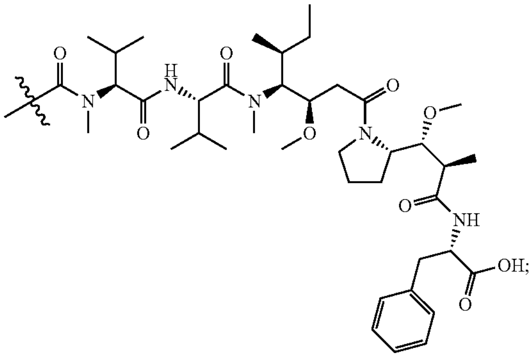

each n is an integer independently selected from 0 to 6; and each Q is selected from H and —$NO_2$.

2. A compound selected from the group consisting of:
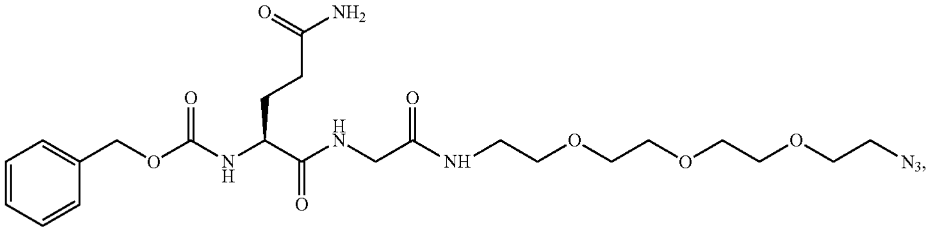
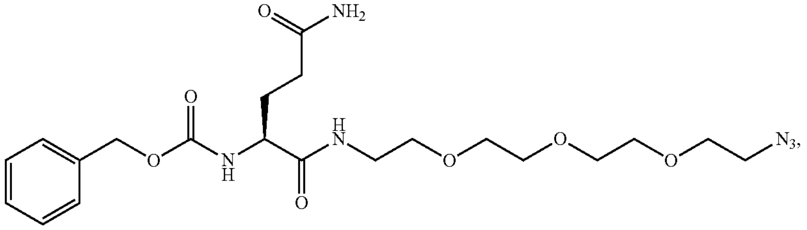
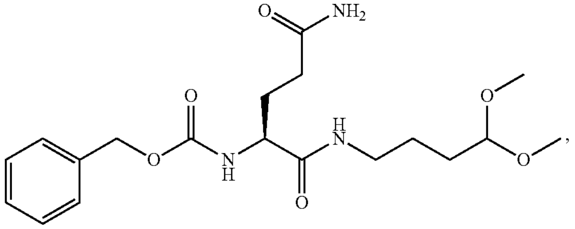
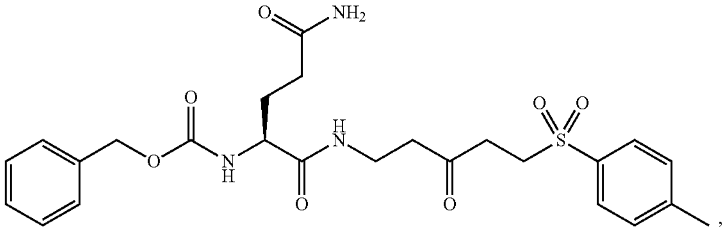
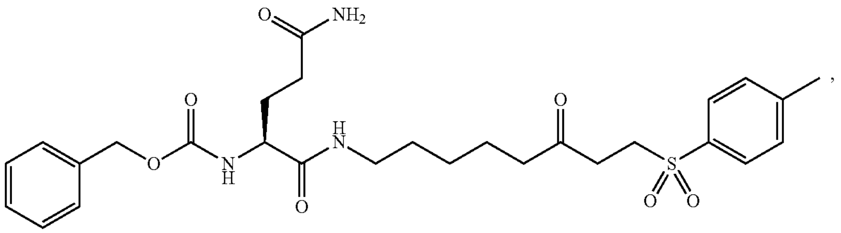
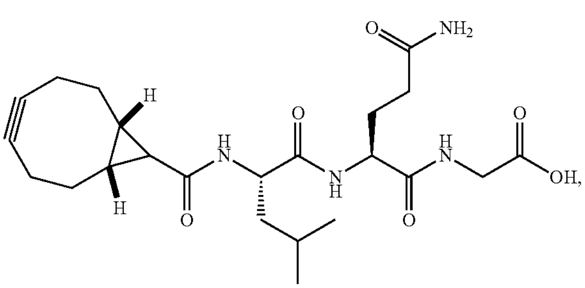
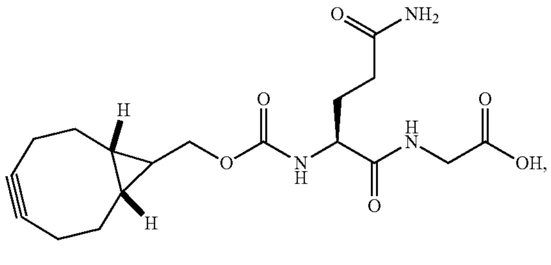

-continued
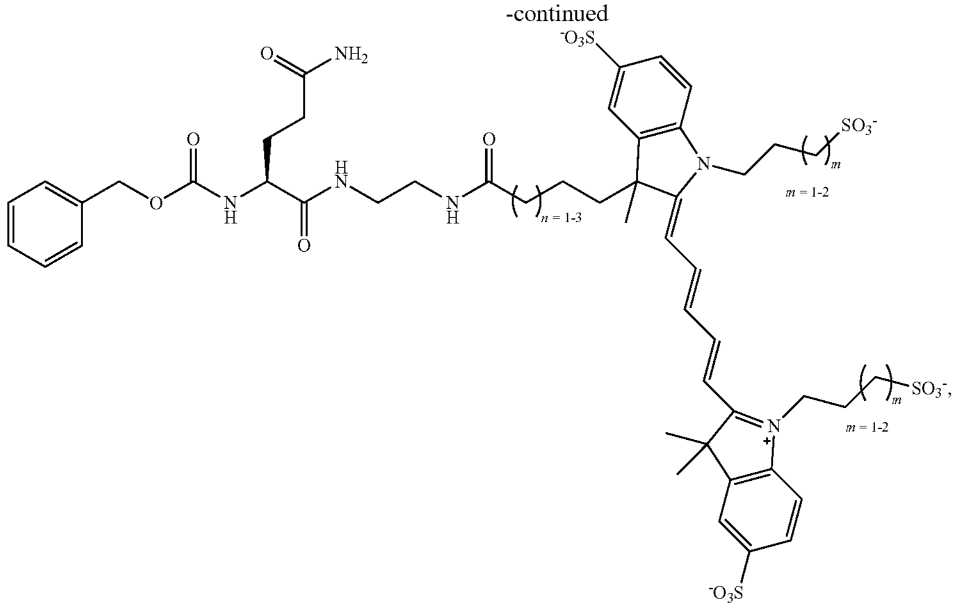
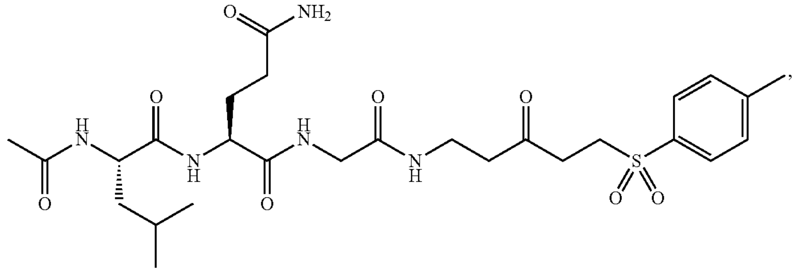
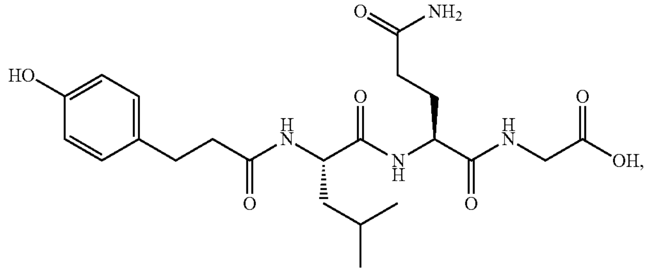
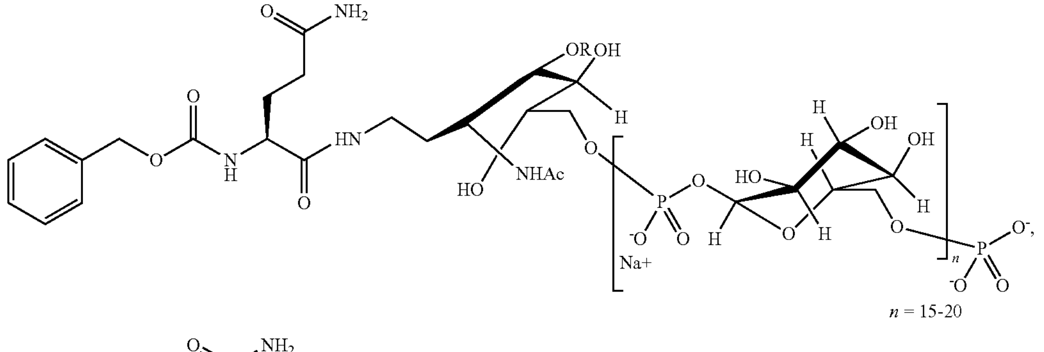
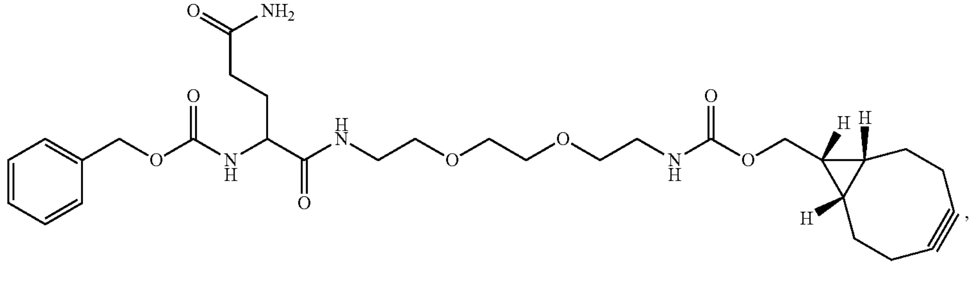

-continued
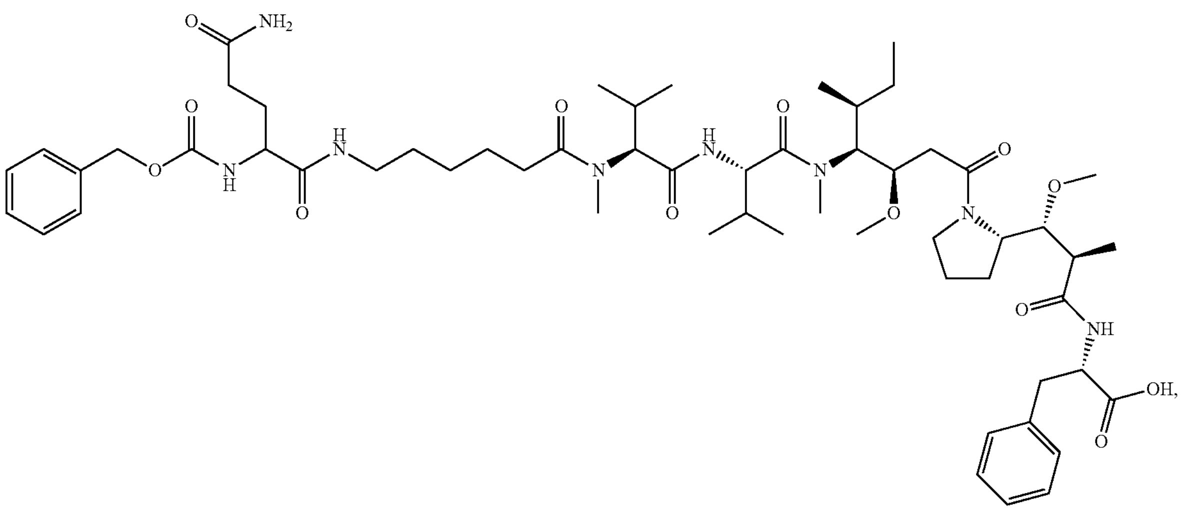
,
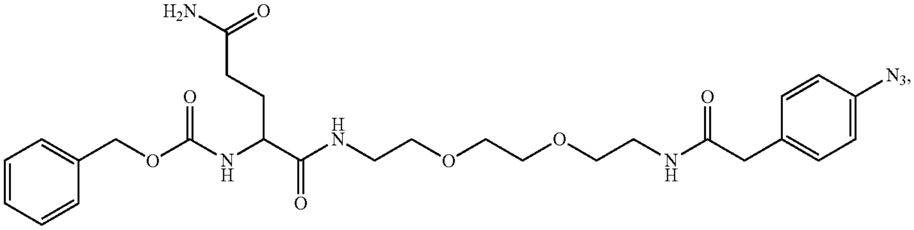
,
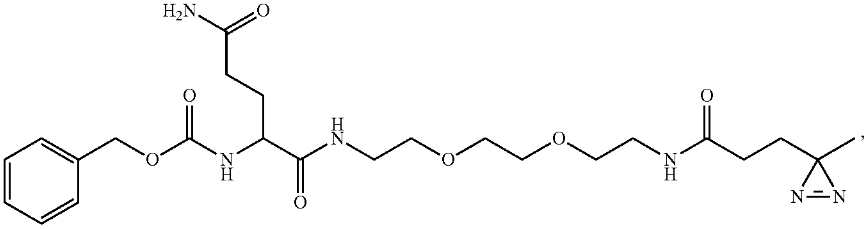
,
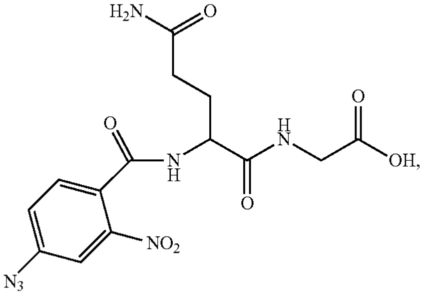
,
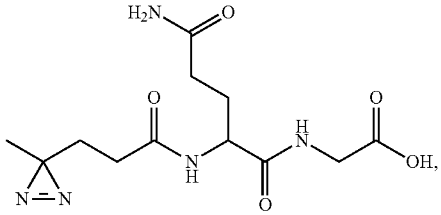
,
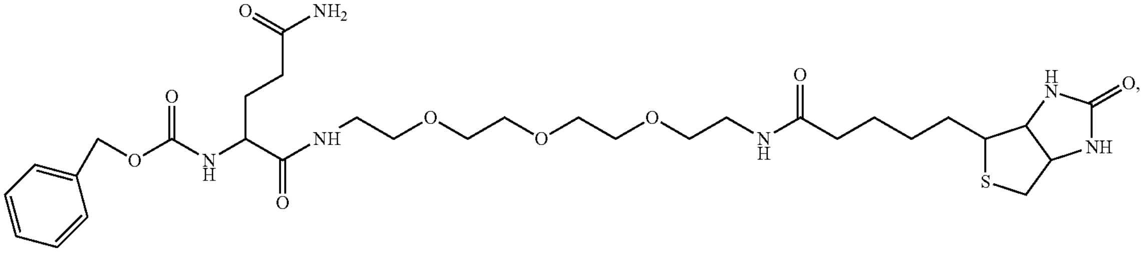
, and -continued

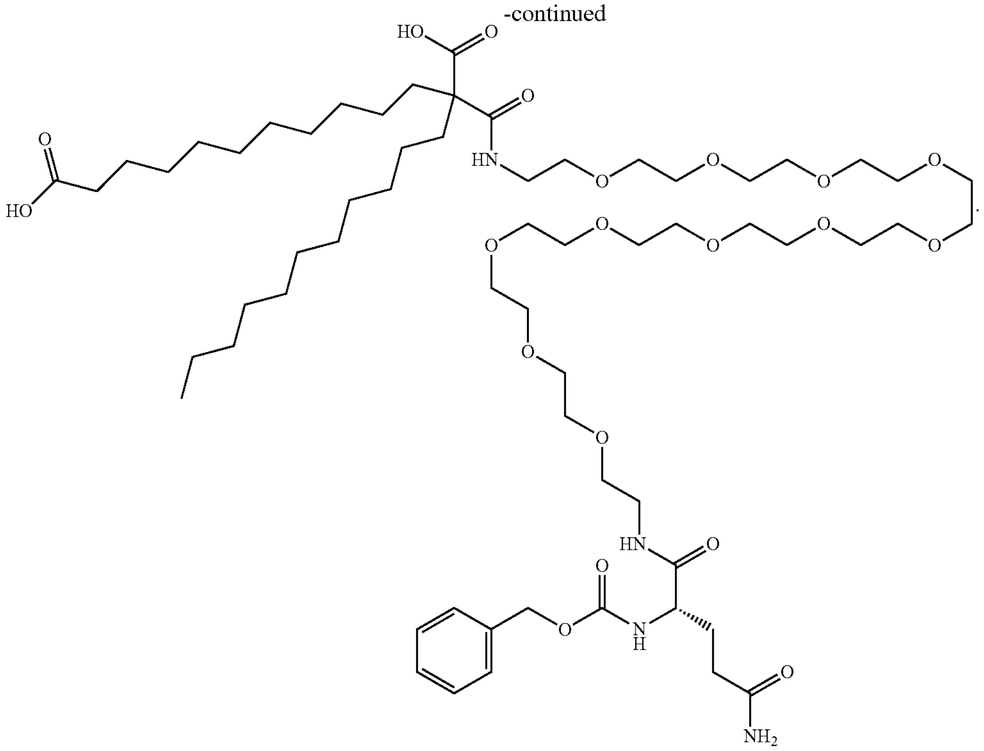

3. The compound of claim 1, wherein W is polyethylene glycol having a molecular weight of between about 40 and about 80,000 amu.

4. The compound of claim 1, wherein $R^1$ is

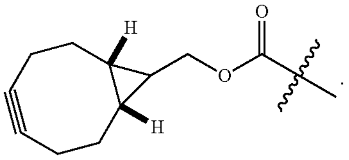 [SMILES: *C(=O)OCC1[C@H]2CCC#CCC[C@@H]12]

5. The compound of claim 1, wherein $R^2$ is selected from cyclooctynyl and

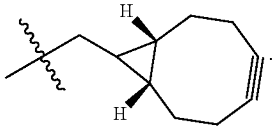 [SMILES: *CC1[C@H]2CCC#CCC[C@@H]12]

6. The compound of claim 1, wherein $R^2$ is a fatty acid.

7. A compound of the formula $R^1$-(Leu)$_x$-Gln-(Gly)$_y$-(A-W-B-$R^2$)$_z$ wherein x is 0 or 1; y is 0 or 1; z is 0 or 1;

$R^1$ is selected from the group consisting of:

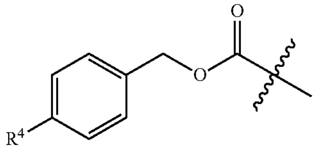

-continued

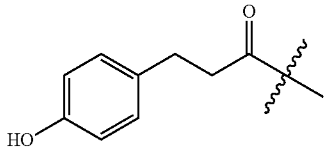

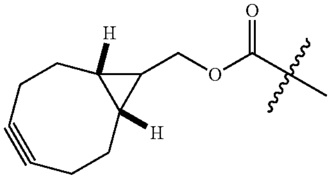

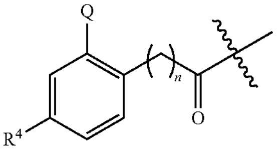

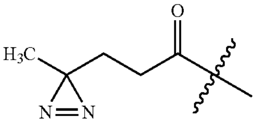

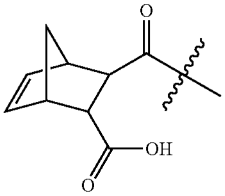

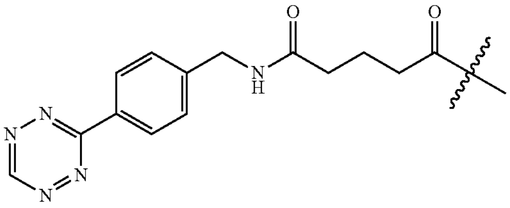

and

-continued

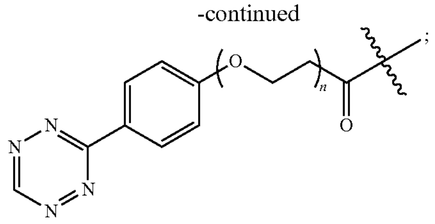

wherein $R^4$ is selected from —H, —$N_3$, and

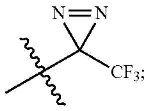 [SMILES: *C1(C(F)(F)F)N=N1]

W is a polyethylene glycol having a molecular weight of between about 40 and about 80,000 amu;

A is absent or selected from —O—, —NH—, and —S—;

B is absent or selected from —O—, —C(O)—, —NH—, —C(O)NH—, —NHC(O)—, —NHC(O)O—, —OC(O)NH—, —OC(O)O—, —C═N(OH)—, —S(O2)—, —$NHS(O_2)$—, —$S(O_2)NH$—, —S(O)—, —NHS(O)—, —S(O)NH—; —C(O)O—, —OC(O)—, —S—, ═NH—O—, ═NH—NH— and ═NH—N($C_1$-$C_{20}$alkyl)-;

$R^2$ is a fluorophore; and each Q is selected from H and —$NO_2$.

8. The compound of claim 7, wherein the fluorophore is selected from the group consisting of a fluorescein, rhodamine, a Cy dye, an Alexa dye, and a coumarin.

9. The compound of claim 7, wherein $R^1$ is

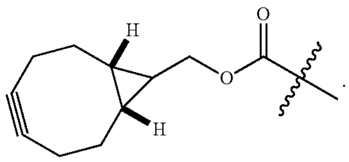 [SMILES: *C(=O)OCC1[C@H]2CCC#CCC[C@@H]12]

* * * * *